US012703750B2

(12) United States Patent
Balyasnikova

(10) Patent No.: US 12,703,750 B2
(45) Date of Patent: Aug. 11, 2026

(54) HUMANIZED ANTIBODY TARGETING THE TUMOR ASSOCIATED ANTIGEN IL13RA2

(71) Applicant: Northwestern University, Evanston, IL (US)

(72) Inventor: Irina V. Balyasnikova, Chicago, IL (US)

(73) Assignee: Northwestern University, Evanston, IL (US)

( * ) Notice: Subject to any disclaimer, the term of this patent is extended or adjusted under 35 U.S.C. 154(b) by 965 days.

(21) Appl. No.: 17/995,966

(22) PCT Filed: Apr. 12, 2021

(86) PCT No.: PCT/US2021/070377

§ 371 (c)(1),
(2) Date: Oct. 11, 2022

(87) PCT Pub. No.: WO2021/207770

PCT Pub. Date: Oct. 14, 2021

(65) Prior Publication Data

US 2023/0312731 A1 Oct. 5, 2023

Related U.S. Application Data

(60) Provisional application No. 63/008,681, filed on Apr. 11, 2020.

(51) Int. Cl.
*C07K 16/28* (2006.01)
*C07K 16/30* (2006.01)

(52) U.S. Cl.
CPC ...... *C07K 16/2866* (2013.01); *C07K 16/2809* (2013.01); *C07K 16/3053* (2013.01); *C07K 2317/24* (2013.01); *C07K 2317/31* (2013.01); *C07K 2317/622* (2013.01); *C07K 2317/92* (2013.01); *C07K 2317/94* (2013.01)

(58) Field of Classification Search
CPC ............ C07K 16/2866; C07K 16/2809; C07K 16/3053; C07K 2317/24; C07K 2317/31; C07K 2317/622; C07K 2317/92; C07K 2317/94; C07K 2317/21; C07K 2317/33; C07K 2317/14; C07K 2317/40; C07K 2317/70; A61K 39/395; A61P 35/00
See application file for complete search history.

(56) References Cited

U.S. PATENT DOCUMENTS 4,342,776 A 8/1982 Cragoe, Jr. et al.
4,399,276 A 8/1983 Miyasaka et al.
4,472,509 A 9/1984 Gansow et al.
4,473,692 A 9/1984 Miyasaka et al.
4,513,138 A 4/1985 Miyasaka et al.
4,526,988 A 7/1985 Hertel
4,545,880 A 10/1985 Miyasaka et al.
4,604,463 A 8/1986 Miyasaka et al.
4,808,614 A 2/1989 Hertel
4,965,392 A 10/1990 Fritzberg et al.
5,004,758 A 4/1991 Boehm et al.
5,021,236 A 6/1991 Gries et al.
5,037,630 A 8/1991 Fritzberg et al.
5,223,608 A 6/1993 Chou
5,530,101 A * 6/1996 Queen ................. C07K 16/089 424/143.1
5,585,089 A * 12/1996 Queen .................... C07K 16/00 424/143.1
5,620,985 A 4/1997 Jacquesy et al.
6,630,124 B1 10/2003 Gozes et al.
7,355,008 B2 4/2008 Stavenhagen et al.
7,381,408 B2 6/2008 Mezo
7,728,114 B2 6/2010 Mach et al.
8,234,784 B2 8/2012 Younger
10,308,719 B2 6/2019 Balyasnikova et al.
2005/0042664 A1* 2/2005 Wu ......................... A61P 43/00 435/6.16
2006/0177896 A1 8/2006 Mach et al.
2014/0271582 A1 9/2014 Forman
2014/0271635 A1 9/2014 Brogdon et al.
2014/0274909 A1 9/2014 Orentas et al.
2014/0286973 A1 9/2014 Powell, Jr.
2014/0301993 A1 10/2014 Powell, Jr.
(Continued)

FOREIGN PATENT DOCUMENTS

EP 0056692 A1 7/1982
EP 0074256 A1 3/1983
(Continued)

OTHER PUBLICATIONS

Uniprot P0DOX5 “Immunoglobulin gamma-1 heavy chain—*Homo sapiens* (Human) _ UniProtKB _ UniProt”, accessed by the examiner Sep. 30, 2025 (Year: 2025).*
Almagro et. al., Front. Immunol. 2018; 8:1751(Year: 2018).*
Chiu ML et al. Antibodies 2019 8, 55, 1-80 (Year: 2019).*
Kashmiri, S.V., et al., 2005. SDR grafting—a new approach to antibody humanization. Methods, 36(1), pp. 25-34 (Year: 2005).*
Margreitter, Christian et al. “Antibody Humanization by Molecular Dynamics Simulations-in-Silico Guided Selection of Critical Backmutations.” Journal of Molecular Recognition 29.6 (2016): 266-275 (Year: 2016).*
(Continued)

*Primary Examiner* — Gregory S Emch
*Assistant Examiner* — Kathleen Cunningchen
(74) *Attorney, Agent, or Firm* — Quarles & Brady LLP

(57) ABSTRACT

The present invention provides humanized antibodies that bind to IL13Rα2, an interleukin-13 receptor that is overexpressed by the majority of glioblastoma tumors and not expressed at significant levels in normal brain tissue. Also provided are bispecific T cell engagers that bind to both IL13Rα2 and to the T cell co-receptor CD3 as well as methods for treating cancer, in which these humanized antibodies are used to target tumors.

20 Claims, 35 Drawing Sheets
(32 of 35 Drawing Sheet(s) Filed in Color)
Specification includes a Sequence Listing.

(56) References Cited

U.S. PATENT DOCUMENTS

| | | | |
|---|---|---|---|
| 2014/0322183 A1 | 10/2014 | Milone et al. | |
| 2014/0322212 A1 | 10/2014 | Brogdon et al. | |
| 2014/0322275 A1 | 10/2014 | Brogdon et al. | |
| 2014/0369977 A1 | 12/2014 | Zhang | |
| 2015/0125468 A1 | 5/2015 | Schmidt et al. | |
| 2016/0017058 A1 | 1/2016 | Kim et al. | |
| 2018/0134796 A1* | 5/2018 | Balyasnikova | A61K 40/31 |
| 2019/0300616 A1 | 10/2019 | Balyasnikova et al. | |
| 2019/0359723 A1 | 11/2019 | Wang et al. | |

FOREIGN PATENT DOCUMENTS

| | | |
|---|---|---|
| EP | 0074770 A1 | 3/1983 |
| EP | 0088642 A2 | 9/1983 |
| EP | 0137145 A1 | 4/1985 |
| EP | 184365 A2 | 6/1986 |
| EP | 0321122 A2 | 6/1989 |
| EP | 0418099 A2 | 3/1991 |
| EP | 2814846 A1 | 12/2014 |
| WO | 2002060950 A2 | 8/2002 |
| WO | 2014100490 A1 | 6/2014 |
| WO | 2014153270 A1 | 9/2014 |
| WO | 2014179759 A1 | 11/2014 |
| WO | 2014180306 A1 | 11/2014 |
| WO | 2014184143 A1 | 11/2014 |
| WO | 2014186469 A2 | 11/2014 |
| WO | 2014190273 A1 | 11/2014 |
| WO | 2014208760 A1 | 12/2014 |
| WO | 2017214092 A1 | 12/2017 |

OTHER PUBLICATIONS

Godbersen, Claire, et al. "NKG2D Ligand-Targeted Bispecific T-Cell Engagers Lead to Robust Antitumor Activity against Diverse Human Tumors." Molecular cancer therapeutics 16.7 (2017): 1335-1346 (Year: 2017).*

Knudson, Karin M., et al. "Recent advances in IL-13Rα2-directed cancer immunotherapy." Frontiers in Immunology 13 (2022): 878365 (Year: 2022).*

Krenciute, Giedre, et al. "Characterization and functional analysis of scFv-based chimeric antigen receptors to redirect T cells to IL 13Rα2-positive glioma." Molecular Therapy 24.2 (2016): 354-363 (Year: 2016).*

Lian, X., et al. Design considerations of an IL13Rα2 antibody-drug conjugate for diffuse intrinsic pontine glioma. acta neuropathol commun 9, 88 (2021). https://doi.org/10.1186/s40478-021-01184-9 (Year: 2021).*

Rillema, Jill, et al. "Development of an IL13Ralpha2 x CD3 bispecific DART® protein for redirected T-cell killing of solid tumors." Cancer Research 76.14_Supplement (2016): 1498-1498. (Year: 2016).*

Rudikoff S et al: "Single amino acid substitution altering antige••binding specificity", Proceedings of the National Academy of Sciences, National Academy of Sciences, vol. 79, No. 6, Mar. 1, 1982 (Mar. 1, 1982), pp. 1979-1983.

Winkler Ket al: "Changing the antigen binding specificity by single point mutations of an anti-p24 (HIV-1) antibody", The Journal of Immunology, Williams & Wilkins Co, US, vol. 165, No. 8, Oct. 15, 2000 (Oct. 15, 2000), pp. 4505-4514.

European Search Report, corresponding to EP21785420.7, dated Mar. 13, 2024.

Hageman et al. "Impact of Tryptophan oxidation in complementarity-determining regions of two monoclonal antibodies on structure-function characterized by hydrogen-deuterium exchange mass spectrometry and surface plasmon resonance", Pharm Res (2019) 36:24.

Jones et al., "Replacing the complementarity-determining regions in a human antibody with those from a mouse", Nature 321:522-525 (1986).

Reichmann et al., "Reshaping human antibodies for therapy", Nature 332:323-329 (1988).

Presta, "Antibody engineering", Curr. Op. Struct. Biol. 2:593-596 (1992).

Van de Broek et al., "Specific cell targeting with nanobody conjugated branched gold nanoparticles for photothermal therapy", ACS Nano, vol. 5, No. 6, 4319-4328, 2011.

Sukhanova et al. "Oriented conjugates of single-domain antibodies and quantum dots: toward a new generation of ultrasmall diagnostic nanoprobes", Nanomedicine, 8 (2012) 516-525.

Wu and Senter, "Arming antibodies: prospects and challenges for immunoconjugates", Nat Biotechnol. (2005) 23 (9):1137-46.

Trail et al., "Monoclonal antibody drug immunoconjugates for targeted treatment of cancer", Cancer Immunol Immunother. (2003) 52(5):328-37.

Saito et al., "Drug delivery strategy utilizing conjugation via reversible disulfide linkages: role and site of cellular reducing activities", Adv Drug Deliv Rev. (2003) 55(2):199-215.

Jones and Shusta, "Blood-Brain Barrier Transport of Therapeutics via Receptor-Mediation", Pharmaceutical Research (2007) 24(9): p. 1759-1771.

Wong, Chemistry of protein conjugation and cross-linking, CRC Press (1991) (relevant passages).

Kindt et al, Kuby Immunology, 6th ed., W.H. Freeman and Co., p. 91 (2007).

Kabat et al, U.S. Dept. of Health and Human Services, Sequences of Proteins of Immunological Interest (1983) (relevant passages).

Chothia et al, "Canonical structures for the hypervariable regions of immunoglobulins", J Mol Biol 196:901-917 (1987).

Balyasnikova et al., "Characterization and immunotherapeutic implications for a novel antibody targeting interleukin (IL)-13 receptor α2", J Biol Chem. Aug. 31, 2012;287(36):30215-27.

Pituch et al. "Neural stem cells secreting bispecific T cell engager to induce selective antiglioma activity", Proc Natl Acad Sci U S A. Mar. 2, 2021;118(9).

Liljeblad et al, "Analysis of agalacto-IgG in rheumatoid arthritis using surface plasmon resonance", Glyco J 17, 323-329 (2000).

Heeley et al., "Mutations flanking the polyglutamine repeat in the modulatory domain of rat glucocorticoid receptor lead to an increase in affinity for hormone", Endocr Res 28, 217-229 (2002).

Sugano et al., "Antibody Targeting of Doxorubicin-loaded Liposomes Suppresses the Growth and Metastatic Spread of Established Human Lung Tumor Xenografts in Severe Combined Immunodeficient Mice", Cancer Research (2000) 60, 6942-6949.

Martin and Mitchell, "Peer Reviewed: Nanomaterials in Analytical Chemistry", Analytical Chemistry News & Features (1998) pp. 322A-327A.

Department of Molecular Biomedicine et al. "Protein Tyrosine Phosphatase-1B Inhibition Disrupts IL13Rα2-Promoted Invasion and Metastasis in Cancer Cells", Cancers 2020, 12(2), 500.

Sawhney et al. "Bioerodible hydrogels based on photopolymerized poly(ethylene glycol)-co-poly(.alpha.-hydroxy acid) diacrylate macromers", Macromolecules, 1993, 26, 581-587.

Kim et al., "Nonthrombogenic bioactive surfaces", Ann. N.Y. Acad. Sci. 516: 116-30 1987.

Jacobs et al., "Surface modification for improved blood compatibility", Artif. Organs 12: 500-501, 1988.

Park et al., "Synthesis and characterization of SPUU-PEO-heparin graft copolymers", J. Poly. Sci, Part A 29:1725-37, 1991.

Park et al., "Blood compatibility of SUUU-PEO-heparin graft copolymers", J. Biomed. Mat. Res. 26:739-45, 1992.

Wani et al., "Plant antitumor agents. 23. Synthesis and antileukemic activity of camptothecin analogs", J. Med. Chem., 29, 2358-2363 (1986).

Lu, Xiaojun, et al. "Deamidation and isomerization liability analysis of 131 clinical-stage antibodies." MAbs. vol. 11. No. 1. Taylor & Francis, 2019.

Wani et al, "Plant antitumor agents. 18. Synthesis and biological activity of camptothecin analogs", J. Med. Chem., 23, 554 (1980).

Wani et. al., "Plant antitumor agents. 25. Total synthesis and antileukemic activity of ring A substituted camptothecin analogs. Structure-activity correlations", J. Med. Chem., 30, 1774 (1987).

Van Tellingen et al, "Pharmacology, bio-analysis and pharmacokinetics of the vinca alkaloids and semi-synthetic derivatives (review)", Anticancer Research, 12, 1699-1716 (1992).

(56) References Cited

OTHER PUBLICATIONS

Henry, et al., "Participation of the N-Terminal Region of Cεε3 in the Binding of Human IgE to Its High-Affinity Receptor FcεRI", Biochemistry 36, 15568-15578, 1997.
Lewis et al "Structural requirements for the interaction of human IgA with the human polymeric Ig receptor", J Immunol. 175:6694-701, 2005.
Sayers et al. "The importance of Lys-352 of human immunoglobulin E in FcepsilonRII/CD23 recognition", J Biol Chem. 279(34):35320-5, 2004.
Shields et al. 2001, "High Resolution Mapping of the Binding Site on Human IgG1 for FcγRI, FcγRII, FcγRIII, and FcRn and Design of IgG1 Variants with Improved Binding to the FcγR", J. Biol. Chem. 276:6591.
Routledge et al. "The effect of aglycosylation on the immunogenicity of a humanized therapeutic CD3 monoclonal antibody", 1995, Transplantation 60:847.
Friend et al. "Phase I Study of an Engineered Aglycosylated Humanized CD3 Antibody in Renal Transplant Rejection", 1999, Transplantation 68:1632.
Ward and Ghetie, "The effector functions of immunoglobulins: implications for therapy", 1995, Therapeutic Immunology 2:77.
Armour et al. "Recombinant human IgG molecules lacking Fcγ receptor I binding and monocyte triggering activities", 1999, Eur. J. Immunol. 29:2613.
Karlin and Altschul, "Methods for assessing the statistical significance of molecular sequence features by using general scoring schemes", 1990, Proc. Natl. Acad. Sci. USA 87: 2267-2268.
Altschul et al., "Gapped BLAST and PSI-BLAST: a new generation of protein database search programs", 1997, Nucl. Acids Res. 25: 3389-3402.
Schaller et al. "Pharmacokinetic Analysis of a Novel Human EGFRvIII:CD3 Bispecific Antibody in Plasma and Whole Blood Using a High-Resolution Targeted Mass Spectrometry Approach", J Proteome Res. Aug. 2, 2019;18(8):3032-3041.
Gedeon, Patrick C., et al. "A rationally designed fully human EGFRvIII: CD3-targeted bispecific antibody redirects human T cells to treat patient-derived intracerebral malignant glioma." Clinical Cancer Research 24.15 (2018): 3611-3631.
Choi, Bryan D., et al. "Rational design and generation of recombinant control reagents for bispecific antibodies through CDR mutagenesis." Journal of immunological methods 395.1-2 (2013): 14-20.
International Search Report and Written Opinion, corresponding to PCT/US2021/070377, dated Jul. 15, 2021.
Rillema, Jill, et al. "Development of an IL13Ralpha2 x CD3 bispecific DART® protein for redirected T-cell killing of solid tumors." Cancer Research 76.14_Supplement (2016): 1498-1498.

* cited by examiner

Chimeric

```
- ATGGGCTGGTCATGCATTATTCTGTTTCTGGTCGCAACTGCTACAGGCGTGCATAGTCAG - 60
   1 - M  G  W  S  C  I  I  L  F  L  V  A  T  A  T  G  V  H  S  Q   - 20

  61 - GTGCAGCTGGTGGAGTCCGGGGGAGGCGTGGTCCAGCCTGGGAGGTCCCTGAGACTCTCC - 120
  21 - V  Q  L  V  E  S  G  G  G  V  V  Q  P  G  R  S  L  R  L  S   - 40

 121 - TGTGCAGCGTCTGGATTCAAGTTCAGTGGCTATGGCATGCACTGGGTCCGCCAGGCTCCA - 180
  41 - C  A  A  S  G  F  K  F  S  G  Y  G  M  H  W  V  R  Q  A  P   - 60

 181 - GGCAAGGGGCTGGAGTGGGTGGCAGTTATATGGTATGATGGAAGTAAGAAATACTATGTA - 240
  61 - G  K  G  L  E  W  V  A  V  I  W  Y  D  G  S  K  K  Y  Y  V   - 80

 241 - GACTCCGTGAAGGGCCGCTTCACCATCTCCAGAGACAATTCCAAGAACACGCTGTATCTG - 300
  81 - D  S  V  K  G  R  F  T  I  S  R  D  N  S  K  N  T  L  Y  L   - 100

 301 - CAAATGAACAGCCTGAGAGCCGAGGACACGGCTGTGTATTACTGTGCGAGACAAATGGGC - 360
 101 - Q  M  N  S  L  R  A  E  D  T  A  V  Y  Y  C  A  R  Q  M  G   - 120

 361 - TACTGGCACTTCGATCTCTGGGGCCGTGGCACCCTGGTCACTGTCTCCTCAGGTGGCGGT - 420
 121 - Y  W  H  F  D  L  W  G  R  G  T  L  V  T  V  S  S  G  G  G   - 140

 421 - GGCTCCGGCGGTGGTGGGTCGGGTGGCGGCGGATCTGAAATTGTGTTGACACAGTCTCCA - 480
 141 - G  S  G  G  G  G  S  G  G  G  G  S  E  I  V  L  T  Q  S  P   - 160

 481 - GCCACCCTGTCTTTGTCTCCAGGGGAAAGAGCCACCCTCTCCTGCAGGGCCAGTCAGAGT - 540
 161 - A  T  L  S  L  S  P  G  E  R  A  T  L  S  C  R  A  S  Q  S   - 180

 541 - GTTAGCAGCTACTTAGCCTGGTACCAACAGAAACCTGGCCAGGCTCCCAGGCTCCTCATC - 600
 181 - V  S  S  Y  L  A  W  Y  Q  Q  K  P  G  Q  A  P  R  L  L  I   - 200

 601 - TATGATGCATCCAACAGGGCCACTGGCATCCCAGCCAGGTTCAGTGGCAGTGGGTCTGGG - 660
 201 - Y  D  A  S  N  R  A  T  G  I  P  A  R  F  S  G  S  G  S  G   - 220

 661 - ACAGACTTCACTCTCACCATCAGCAGCCTAGAGCCTGAAGATTTTGCAGTTTATTACTGT - 720
 221 - T  D  F  T  L  T  I  S  S  L  E  P  E  D  F  A  V  Y  Y  C   - 240

 721 - CAGCAGCGTAGCAACTGGCCTCCGCTCACTTTCGGCGGAGGGACCAAGGTGGAGATCAAA - 780
 241 - Q  Q  R  S  N  W  P  P  L  T  F  G  G  G  T  K  V  E  I  K   - 260

 781 - GGAGGCGGATCTGGCGGAGGCGGATCTGGCTCTGGAGGCGGATCTGGCGGAGGCGGATCT - 840
 261 - G  G  G  S  G  G  G  G  S  G  S  G  G  G  S  G  G  G  G  S   - 280

 841 - GGCGGAGGCGACATCGTGATGACCCAGTCCCCTGATTCTCTGGCCGTGTCTCTGGGAGAG - 900
 281 - G  G  G  D  I  V  M  T  Q  S  P  D  S  L  A  V  S  L  G  E   - 300

 901 - AGGGCAACAATCAACTGCAGAGCCTCTGAGAGCGTGGACAACTACGGCATCAGCTTCATG - 960
 301 - R  A  T  I  N  C  R  A  S  E  S  V  D  N  Y  G  I  S  F  M   - 320

 961 - AATTGGTATCAGCAGAAGCCAGGCCAGCCCCCTAAGCTGCTGATCTACGCAGCAAGCAGG - 1020
 321 - N  W  Y  Q  Q  K  P  G  Q  P  P  K  L  L  I  Y  A  A  S  R   - 340

1021 - CAGGGATCCGGAGTGCCCGACCGGTTCTCCGGATCTGGAAGCGGAACCGACTTCACCCTG - 1080
 341 - Q  G  S  G  V  P  D  R  F  S  G  S  G  S  G  T  D  F  T  L   - 360

1081 - ACAATCAGCTCCCTGCAGGCCGAGGATGTGGCCGTGTACTATTGTCAGCAGTCCAAGGAG - 1140
 361 - T  I  S  S  L  Q  A  E  D  V  A  V  Y  Y  C  Q  Q  S  K  E   - 380

1141 - GTGCCATGGACCTTTGGCGGAGGAACAAAGCTGGAGATCAAGGGTGGCGGTGGCTCCGGC - 1200
 381 - V  P  W  T  F  G  G  G  T  K  L  E  I  K  G  G  G  G  S  G   - 400

1201 - GGTGGTGGGTCGGGTGGCGGCGGATCTCAGGTGCAGCTGGTGCAGTCCGGAGCAGAGGTG - 1260
 401 - G  G  G  S  G  G  G  G  S  Q  V  Q  L  V  Q  S  G  A  E  V   - 420

1261 - AAGAAGCCAGGAAGCTCCGTGAAGGTGTCTTGCAAGGCCAGCGGCTATACCTTCTCTAAC - 1320
 421 - K  K  P  G  S  S  V  K  V  S  C  K  A  S  G  Y  T  F  S  N   - 440

1321 - TACCTGATGAATTGGGTGAGGCAGGCACCAGGACAGGGACTGGAGTGGATGGGCCGCATC - 1380
 441 - Y  L  M  N  W  V  R  Q  A  P  G  Q  G  L  E  W  M  G  R  I   - 460

1381 - GATCCTTATGACGGCGATATCGACTACAACCAGAACTTCAAGGATCGGGTGACCATCACA - 1440
 461 - D  P  Y  D  G  D  I  D  Y  N  Q  N  F  K  D  R  V  T  I  T   - 480

1441 - GCCGACAAGAGCACCTCCACAGCCTATATGGAGCTGTCTAGCCTGCGGAGCGAGGATACC - 1500
 481 - A  D  K  S  T  S  T  A  Y  M  E  L  S  S  L  R  S  E  D  T   - 500

1501 - GCCGTGTACTATTGTGCCAGAGGCTACGGCACAGCCTATGGAGTGGACTACTGGGGACAG - 1560
 501 - A  V  Y  Y  C  A  R  G  Y  G  T  A  Y  G  V  D  Y  W  G  Q   - 520

1561 - GGCACCCTGGTGACAGTGTCCTCTCATCATCATCATCATCATTGA - 1605 (SEQ ID NO: 47)
 521 - G  T  L  V  T  V  S  S  H  H  H  H  H  H  *  X              - 540 (SEQ ID NO: 48)
```

Bispecific T cell engager nucleotide/aa sequence

Figure 28 (continued)

SEQ ID NO:48- Leader 28F11VH $(Gly_4S)_3$ linker 28F11VL 23 aa linker humscFv47 VL1 $(Gly_4S)_3$ humscFv47 VH1 6HIS tag
Synthetic - Humanized antibody MGWSCIILFLVATATGVHSQVQLVESGGGVVQPGRSLRLSCAASGFKFSGYGMHWVRQAPGKGLEW
VAVIWYDGSKKYYVDSVKGRFTISRDNSKNTLYLQMNSLRAEDTAVYYCARQMGYWHFDLWGRGT
LVTVSSGGGGSGGGGSGGGGSEIVLTQSPATLSLSPGERATLSCRASQSVSSYLAWYQQKPGQAPRLLI
YDASNRATGIPARFSGSGSGTDFTLTISSLEPEDFAVYYCQQRSNWPPLTFGGGTKVEIKGGGSGGGGS
GSGGGSGGGGSGGGDIVMTQSPDSLAVSLGERATINCRASESVDNYGISFMNWYQQKPGQPPKLLIYA
ASRQGSGVPDRFSGSGSGTDFTLTISSLQAEDVAVYYCQQSKEVPWTFGGGTKLEIKGGGGSGGGGSG
GGGSQVQLVQSGAEVKKPGSSVKVSCKASGYTFSNYLMNWVRQAPGQGLEWMGRIDPYDGDIDYNQ
NFKDRVTITADKSTSTAYMELSSLRSEDTAVYYCARGYGTAYGVDYWGQGTLVTVSSHHHHHH*

SEQ ID NO:49- Leader 28F11VH (Gly4S)3 linker 28F11VL $(Gly_4S)_3$ aa linker humscFv47 VL1 (Gly4S)3 humscFv47 VH1 6HIS tag
Synthetic - Humanized antibody - mutants MGWSCIILFLVATATGVHSQVQLVESGGGVVQPGRSLRLSCAASGFKFSGYGMHWVRQAPGKGLEW
VAVIWYDGSKKYYVDSVKGRFTISRDNSKNTLYLQMNSLRAEDTAVYYCARQMGYWHFDLWGRGT
LVTVSSGGGGSGGGGSGGGGSEIVLTQSPATLSLSPGERATLSCRASQSVSSYLAWYQQKPGQAPRLLI
YDASNRATGIPARFSGSGSGTDFTLTISSLEPEDFAVYYCQQRSNWPPLTFGGGTKVEIKGGGSGGGGS
GSGGGSGGGGSGGGDIVMTQSPDSLAVSLGERATINCRASESVDNYGISFMNWYQQKPGQPPKLLIYA
ASRQGSGVPDRFSGSGSGTDFTLTISSLQAEDVAVYYCQQSKEVP$X_1$TFGGGTKLEIKGGGGSGGGGSG
GGGSQVQLVQSGAEVKKPGSSVKVSCKASGYTFSNYLMNWVRQAPGQGLEWMGRIDPY$X_2X_3$DIDYN
QNFKDRVTITADKSTSTAYMELSSLRSEDTAVYYCARGYGTAYGVDYWGQGTLVTVSSHHHHHH*

Wherein $X_1$-(100) is W or F $X_2$-(55) D or E $X_3$- (56) G or A

SEQUENCE LISTING

```
<160> NUMBER OF SEQ ID NOS: 62

<210> SEQ ID NO 1
<211> LENGTH: 449
<212> TYPE: PRT
<213> ORGANISM: Artificial Sequence
<220> FEATURE:
<223> OTHER INFORMATION: Synthetic - pCDNA3.4-IgG1-VH1

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asn Tyr
            20                  25                  30

Leu Met Asn Trp Val Arg Gln Ala Pro Gly Gln Gly Leu Glu Trp Met
        35                  40                  45
```

-continued

```
Gly Arg Ile Asp Pro Tyr Asp Gly Asp Ile Asp Tyr Asn Gln Asn Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Gly Thr Ala Tyr Gly Val Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

-continued

```
<210> SEQ ID NO 2
<211> LENGTH: 449
<212> TYPE: PRT
<213> ORGANISM: Artificial Sequence
<220> FEATURE:
<223> OTHER INFORMATION: Synthetic - pCDNA3.4-IgG1-VH2

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
            20                  25                  30

Leu Met Asn Trp Val Arg Gln Ala Pro Gly Gln Arg Leu Glu Trp Met
        35                  40                  45

Gly Arg Ile Asp Pro Tyr Asp Gly Asp Ile Asp Tyr Asn Gln Asn Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Gly Thr Ala Tyr Gly Val Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
```

-continued

```
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 3
<211> LENGTH: 449
<212> TYPE: PRT
<213> ORGANISM: Artificial Sequence
<220> FEATURE:
<223> OTHER INFORMATION: Synthetic - pCDNA3.4-IgG1-VH3

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
            20                  25                  30

Leu Met Asn Trp Val Arg Gln Ala Pro Gly Gln Gly Leu Glu Trp Met
        35                  40                  45

Gly Arg Ile Asp Pro Tyr Asp Gly Asp Ile Asp Tyr Asn Gln Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Tyr Gly Thr Ala Tyr Gly Val Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 4
<211> LENGTH: 449
<212> TYPE: PRT
<213> ORGANISM: Artificial Sequence
<220> FEATURE:
<223> OTHER INFORMATION: Synthetic - pCDNA3.4-IgG1-VH4

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
            20                  25                  30

Leu Met Asn Trp Val Arg Gln Ala Thr Gly Gln Gly Leu Glu Trp Met
        35                  40                  45

Gly Arg Ile Asp Pro Tyr Asp Gly Asp Ile Asp Tyr Asn Gln Asn Phe
    50                  55                  60

Lys Asp Arg Val Thr Ile Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Gly Thr Ala Tyr Gly Val Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

-continued

```
Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 5
<211> LENGTH: 218
<212> TYPE: PRT
<213> ORGANISM: Artificial Sequence
<220> FEATURE:
<223> OTHER INFORMATION: Synthetic - pCDNA3.4-IgG1-VL1

<400> SEQUENCE: 5

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Ile Ser Phe Met Asn Trp Tyr Gln Gln Lys Pro Gly Gln Pro Pro
        35                  40                  45

Lys Leu Leu Ile Tyr Ala Ala Ser Arg Gln Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Val Pro Trp Thr Phe Gly Gly Gly Thr Lys Leu Glu Ile Lys Arg
```

-continued

```
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 6
<211> LENGTH: 218
<212> TYPE: PRT
<213> ORGANISM: Artificial Sequence
<220> FEATURE:
<223> OTHER INFORMATION: Synthetic - pCDNA3.4-IgG1-VL2

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Tyr Gln Gln Lys Pro Gly Lys Ala Pro
        35                  40                  45

Lys Leu Leu Ile Tyr Ala Ala Ser Arg Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Lys
                85                  90                  95

Glu Val Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 7
<211> LENGTH: 218
<212> TYPE: PRT
```

-continued

```
<213> ORGANISM: Artificial Sequence
<220> FEATURE:
<223> OTHER INFORMATION: Synthetic - pCDNA3.4-IgG1-VL3

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Ile Ser Phe Met Asn Trp Tyr Gln Gln Lys Pro Gly Gln Ala Pro
        35                  40                  45

Arg Leu Leu Ile Tyr Ala Ala Ser Arg Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Val Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 8
<211> LENGTH: 218
<212> TYPE: PRT
<213> ORGANISM: Artificial Sequence
<220> FEATURE:
<223> OTHER INFORMATION: Synthetic - pCDNA3.4-IgG1-VL4

<400> SEQUENCE: 8

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Asp Asn Tyr
            20                  25                  30

Gly Ile Ser Phe Met Asn Trp Tyr Gln Gln Lys Pro Gly Gln Ala Pro
        35                  40                  45

Arg Leu Leu Ile Tyr Ala Ala Ser Arg Gln Gly Ser Gly Ile Pro Ala
    50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Gln Gln Ser Lys
                85                  90                  95

Glu Val Pro Trp Thr Phe Gly Gly Gly Thr Lys Leu Glu Ile Lys Arg
            100                 105                 110
```

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 9
<211> LENGTH: 449
<212> TYPE: PRT
<213> ORGANISM: Artificial Sequence
<220> FEATURE:
<223> OTHER INFORMATION: Synthetic - Modified pCDNA3.4-IgG1-VH1
<220> FEATURE:
<221> NAME/KEY: MISC_FEATURE
<222> LOCATION: (34)..(34)
<223> OTHER INFORMATION: X1 is M, L, A, I, or V
<220> FEATURE:
<221> NAME/KEY: MISC_FEATURE
<222> LOCATION: (52)..(52)
<223> OTHER INFORMATION: X2 is D or E
<220> FEATURE:
<221> NAME/KEY: MISC_FEATURE
<222> LOCATION: (53)..(53)
<223> OTHER INFORMATION: X3 is P or A
<220> FEATURE:
<221> NAME/KEY: MISC_FEATURE
<222> LOCATION: (55)..(55)
<223> OTHER INFORMATION: X4 is D or E
<220> FEATURE:
<221> NAME/KEY: MISC_FEATURE
<222> LOCATION: (56)..(56)
<223> OTHER INFORMATION: X5 is G or A

<400> SEQUENCE: 9

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Ser Asn Tyr
20 25 30

Leu Xaa Asn Trp Val Arg Gln Ala Pro Gly Gln Gly Leu Glu Trp Met
35 40 45

Gly Arg Ile Xaa Xaa Tyr Xaa Xaa Asp Ile Asp Tyr Asn Gln Asn Phe
50 55 60

Lys Asp Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Tyr Gly Thr Ala Tyr Gly Val Asp Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp

-continued

```
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 10
<211> LENGTH: 449
<212> TYPE: PRT
<213> ORGANISM: Artificial Sequence
<220> FEATURE:
<223> OTHER INFORMATION: Synthetic - Modified pCDNA3.4-IgG1-VH2
<220> FEATURE:
<221> NAME/KEY: MISC_FEATURE
<222> LOCATION: (34)..(34)
<223> OTHER INFORMATION: X1 is M, L, A, I, or V
<220> FEATURE:
<221> NAME/KEY: MISC_FEATURE
<222> LOCATION: (52)..(52)
<223> OTHER INFORMATION: X2 is D or E
<220> FEATURE:
<221> NAME/KEY: MISC_FEATURE
<222> LOCATION: (53)..(53)
<223> OTHER INFORMATION: X3 is P or A
<220> FEATURE:
<221> NAME/KEY: MISC_FEATURE
<222> LOCATION: (55)..(55)
<223> OTHER INFORMATION: X4 is D or E
<220> FEATURE:
<221> NAME/KEY: MISC_FEATURE
<222> LOCATION: (56)..(56)
<223> OTHER INFORMATION: X5 is G or A

<400> SEQUENCE: 10

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
            20                  25                  30

Leu Xaa Asn Trp Val Arg Gln Ala Pro Gly Gln Arg Leu Glu Trp Met
        35                  40                  45

Gly Arg Ile Xaa Xaa Tyr Xaa Xaa Asp Ile Asp Tyr Asn Gln Asn Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Gly Thr Ala Tyr Gly Val Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
```

-continued

```
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 11
<211> LENGTH: 449
<212> TYPE: PRT
<213> ORGANISM: Artificial Sequence
<220> FEATURE:
<223> OTHER INFORMATION: Synthetic - Modified  pCDNA3.4-IgG1-VH3
<220> FEATURE:
<221> NAME/KEY: MISC_FEATURE
<222> LOCATION: (34)..(34)
<223> OTHER INFORMATION: X1 is M, L, A, I, or V
<220> FEATURE:
<221> NAME/KEY: MISC_FEATURE
<222> LOCATION: (52)..(52)
<223> OTHER INFORMATION: X2 is D or E
<220> FEATURE:
<221> NAME/KEY: MISC_FEATURE
<222> LOCATION: (53)..(53)
<223> OTHER INFORMATION: X3 is P or A
<220> FEATURE:
<221> NAME/KEY: MISC_FEATURE
<222> LOCATION: (55)..(55)
<223> OTHER INFORMATION: X4 is D or E
<220> FEATURE:
<221> NAME/KEY: MISC_FEATURE
<222> LOCATION: (56)..(56)
<223> OTHER INFORMATION: X5 is G or A

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
            20                  25                  30

Leu Xaa Asn Trp Val Arg Gln Ala Pro Gly Gln Gly Leu Glu Trp Met
        35                  40                  45

Gly Arg Ile Xaa Xaa Tyr Xaa Xaa Asp Ile Asp Tyr Asn Gln Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Tyr Gly Thr Ala Tyr Gly Val Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

-continued

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 12
<211> LENGTH: 449
<212> TYPE: PRT
<213> ORGANISM: Artificial Sequence
<220> FEATURE:
<223> OTHER INFORMATION: Synthetic - Modified pCDNA3.4-IgG1-VH4
<220> FEATURE:
<221> NAME/KEY: MISC_FEATURE
<222> LOCATION: (34)..(34)
<223> OTHER INFORMATION: X1 is M, L, A, I, or V
<220> FEATURE:
<221> NAME/KEY: MISC_FEATURE
<222> LOCATION: (52)..(52)
<223> OTHER INFORMATION: X2 is D or E
<220> FEATURE:
<221> NAME/KEY: MISC_FEATURE
<222> LOCATION: (53)..(53)
<223> OTHER INFORMATION: X3 is P or A
<220> FEATURE:
<221> NAME/KEY: MISC_FEATURE
<222> LOCATION: (55)..(55)
<223> OTHER INFORMATION: X4 is D or E
<220> FEATURE:
<221> NAME/KEY: MISC_FEATURE
<222> LOCATION: (56)..(56)
```

-continued

<223> OTHER INFORMATION: X5 is G or A

<400> SEQUENCE: 12

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Ser Asn Tyr
20 25 30

Leu Xaa Asn Trp Val Arg Gln Ala Thr Gly Gln Gly Leu Glu Trp Met
35 40 45

Gly Arg Ile Xaa Xaa Tyr Xaa Xaa Asp Ile Asp Tyr Asn Gln Asn Phe
50 55 60

Lys Asp Arg Val Thr Ile Thr Arg Asn Thr Ser Ile Ser Thr Ala Tyr
65 70 75 80

Met Glu Leu Ser Ser Leu Arg Ser Glu Asp Thr Ala Val Tyr Tyr Cys
85 90 95

Ala Arg Gly Tyr Gly Thr Ala Tyr Gly Val Asp Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 13
<211> LENGTH: 218
<212> TYPE: PRT
<213> ORGANISM: Artificial Sequence
<220> FEATURE:
<223> OTHER INFORMATION: Synthetic - Modified pCDNA3.4-IgG1-VL1
<220> FEATURE:
<221> NAME/KEY: MISC_FEATURE
<222> LOCATION: (37)..(37)
<223> OTHER INFORMATION: X1 is M, L, A, I, or V
<220> FEATURE:
<221> NAME/KEY: MISC_FEATURE
<222> LOCATION: (58)..(58)
<223> OTHER INFORMATION: X2 is Q, E, R, or A
<220> FEATURE:
<221> NAME/KEY: MISC_FEATURE
<222> LOCATION: (94)..(94)
<223> OTHER INFORMATION: X3 is Q, E, R, or A
<220> FEATURE:
<221> NAME/KEY: MISC_FEATURE
<222> LOCATION: (100)..(100)
<223> OTHER INFORMATION: X4 is W, F, or Y

<400> SEQUENCE: 13

Asp Ile Val Met Thr Gln Ser Pro Asp Ser Leu Ala Val Ser Leu Gly
1 5 10 15

Glu Arg Ala Thr Ile Asn Cys Arg Ala Ser Glu Ser Val Asp Asn Tyr
20 25 30

Gly Ile Ser Phe Xaa Asn Trp Tyr Gln Gln Lys Pro Gly Gln Pro Pro
35 40 45

Lys Leu Leu Ile Tyr Ala Ala Ser Arg Xaa Gly Ser Gly Val Pro Asp
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln Xaa Ser Lys
85 90 95

Glu Val Pro Xaa Thr Phe Gly Gly Gly Thr Lys Leu Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 14
<211> LENGTH: 218
<212> TYPE: PRT
<213> ORGANISM: Artificial Sequence
<220> FEATURE:
<223> OTHER INFORMATION: Synthetic - Modified pCDNA3.4-IgG1-VL2
<220> FEATURE:
<221> NAME/KEY: MISC_FEATURE
<222> LOCATION: (37)..(37)
<223> OTHER INFORMATION: X1 is M, L, A, I, or V
<220> FEATURE:
<221> NAME/KEY: MISC_FEATURE
<222> LOCATION: (58)..(58)
<223> OTHER INFORMATION: X2 is Q, E, R, or A
<220> FEATURE:
<221> NAME/KEY: MISC_FEATURE
<222> LOCATION: (94)..(94)
<223> OTHER INFORMATION: X3 is Q, E, R, or A
<220> FEATURE:
<221> NAME/KEY: MISC_FEATURE
<222> LOCATION: (100)..(100)
<223> OTHER INFORMATION: X4 is W, F, or Y

<400> SEQUENCE: 14

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Xaa Asn Trp Tyr Gln Gln Lys Pro Gly Lys Ala Pro
        35                  40                  45

Lys Leu Leu Ile Tyr Ala Ala Ser Arg Xaa Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Xaa Ser Lys
                85                  90                  95

Glu Val Pro Xaa Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 15
<211> LENGTH: 218
<212> TYPE: PRT
<213> ORGANISM: Artificial Sequence
<220> FEATURE:
<223> OTHER INFORMATION: Synthetic - Modified pCDNA3.4-IgG1-VL3
<220> FEATURE:
<221> NAME/KEY: MISC_FEATURE
<222> LOCATION: (37)..(37)
<223> OTHER INFORMATION: X1 is M, L, A, I, or V
<220> FEATURE:
<221> NAME/KEY: MISC_FEATURE
<222> LOCATION: (58)..(58)
<223> OTHER INFORMATION: X2 is Q, E, R, or A
<220> FEATURE:
<221> NAME/KEY: MISC_FEATURE
<222> LOCATION: (94)..(94)
<223> OTHER INFORMATION: X3 is Q, E, R, or A
<220> FEATURE:
<221> NAME/KEY: MISC_FEATURE
<222> LOCATION: (100)..(100)
<223> OTHER INFORMATION: X4 is W, F, or Y

<400> SEQUENCE: 15

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Ile Ser Phe Xaa Asn Trp Tyr Gln Gln Lys Pro Gly Gln Ala Pro
        35                  40                  45

Arg Leu Leu Ile Tyr Ala Ala Ser Arg Xaa Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Xaa Ser Lys
                85                  90                  95

Glu Val Pro Xaa Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 16
<211> LENGTH: 218
<212> TYPE: PRT
<213> ORGANISM: Artificial Sequence
<220> FEATURE:
<223> OTHER INFORMATION: Synthetic - Modified pCDNA3.4-IgG1-VL4
<220> FEATURE:
<221> NAME/KEY: MISC_FEATURE
<222> LOCATION: (37)..(37)
<223> OTHER INFORMATION: X1 is M, L, A, I, or V
<220> FEATURE:
<221> NAME/KEY: MISC_FEATURE
<222> LOCATION: (58)..(58)
<223> OTHER INFORMATION: X2 is Q, E, R, or A
<220> FEATURE:
<221> NAME/KEY: MISC_FEATURE
<222> LOCATION: (94)..(94)
<223> OTHER INFORMATION: X3 is Q, E, R, or A
<220> FEATURE:
<221> NAME/KEY: MISC_FEATURE
<222> LOCATION: (100)..(100)

-continued

<223> OTHER INFORMATION: X4 is W, F, or Y

<400> SEQUENCE: 16

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Asp Asn Tyr
            20                  25                  30

Gly Ile Ser Phe Xaa Asn Trp Tyr Gln Gln Lys Pro Gly Gln Ala Pro
        35                  40                  45

Arg Leu Leu Ile Tyr Ala Ala Ser Arg Xaa Gly Ser Gly Ile Pro Ala
    50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Gln Xaa Ser Lys
                85                  90                  95

Glu Val Pro Xaa Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 17
<211> LENGTH: 1350
<212> TYPE: DNA
<213> ORGANISM: Artificial Sequence
<220> FEATURE:
<223> OTHER INFORMATION: Synthetic - pCDNA3.4-IgG1-VH1

<400> SEQUENCE: 17

```
caggtgcagc tggtgcagtc cggagcagag gtgaagaagc caggaagctc cgtgaaggtg     60

tcttgcaagg ccagcggcta taccttctct aactacctga tgaattgggt gaggcaggca    120

ccaggacagg gactggagtg gatgggccgc atcgatcctt atgacggcga tatcgactac    180

aaccagaact tcaaggatcg ggtgaccatc acagccgaca agagcacctc cacagcctat    240

atggagctgt ctagcctgcg gagcgaggat accgccgtgt actattgtgc cagaggctac    300

ggcacagcct atggagtgga ctactgggga cagggcaccc tggtgacagt gtcctctgcc    360

agcaccaagg gcccttccgt gtttccactg gccccctcct ctaaatccac atctggcggc    420

accgccgccc tgggctgtct ggtgaaggac tacttcccag agcctgtgac agtgtcctgg    480

aactctggcg ccctgacatc cggcgtgcac acatttccag ccgtgctgca gagctccggc    540

ctgtacagcc tgtctagcgt ggtgacagtg ccctcctcta gcctgggcac acagacctat    600

atctgcaacg tgaatcacaa gccaagcaat accaaggtgg acaagaaggt ggagcccaag    660

tcctgtgata agacacacac ctgccccccct tgtcctgctc ccgagctgct gggcggccct    720
```

agcgtgttcc tgtttccacc caagcctaag gacaccctga tgatctcccg gacacccgag 780
gtgacctgcg tggtggtgga cgtgtctcac gaggatcctg aggtgaagtt caactggtat 840
gtggatggcg tggaggtgca caatgccaag accaagccca gagaggagca gtacaactct 900
acatataggg tggtgagcgt gctgaccgtg ctgcaccagg actggctgaa cggcaaggag 960
tataagtgca aggtgtccaa taaggccctg cccgccccca tcgagaagac aatcagcaag 1020
gccaagggcc agcctcggga gccacaggtg tacaccctgc ctccatccag agacgagctg 1080
acaaagaacc aggtgtctct gacatgtctg gtgaagggct tctatcctag cgatatcgcc 1140
gtggagtggg agtccaatgg ccagccagag aacaattaca agaccacacc ccctgtgctg 1200
gactccgatg gctccttctt tctgtattcc aagctgaccg tggataagtc tcggtggcag 1260
cagggcaacg tgttcagctg ttccgtgatg cacgaagccc tgcataatca ctatactcag 1320
aaatccctgt ccctgtcacc tggaaagtga 1350

<210> SEQ ID NO 18
<211> LENGTH: 1350
<212> TYPE: DNA
<213> ORGANISM: Artificial Sequence
<220> FEATURE:
<223> OTHER INFORMATION: Synthetic - pCDNA3.4-IgG1-VH2

<400> SEQUENCE: 18
caggtgcagc tggtgcagag cggagcagag gtgaagaagc caggagccag cgtgaaggtg 60
tcctgcaagg cctctggcta taccttctcc aactacctga tgaattgggt gaggcaggca 120
ccaggacagc gcctggagtg gatgggccgg atcgatcctt atgacggcga tatcgactac 180
aaccagaact tcaaggatcg ggtgaccatc acaagagaca cctccgcctc tacagcctat 240
atggagctga gctccctgag gtctgaggat accgccgtgt actattgtgc aaggggatac 300
ggaacagcat atggagtgga ctactgggga cagggcaccc tggtgacagt gtctagcgcc 360
agcaccaagg gcccttccgt gtttccactg gccccctcct ctaaatccac atctggcggc 420
accgccgccc tgggctgtct ggtgaaggac tacttcccag agcctgtgac agtgtcctgg 480
aactctggcg ccctgacatc cggcgtgcac acatttccag ccgtgctgca gagctccggc 540
ctgtacagcc tgtctagcgt ggtgacagtg ccctcctcta gcctgggcac acagacctat 600
atctgcaacg tgaatcacaa gccaagcaat accaaggtgg acaagaaggt ggagcccaag 660
tcctgtgata agacacacac ctgcccccct tgtcctgctc ccgagctgct gggcggccct 720
agcgtgttcc tgtttccacc caagcctaag gacaccctga tgatctcccg gacacccgag 780
gtgacctgcg tggtggtgga cgtgtctcac gaggatcctg aggtgaagtt caactggtat 840
gtggatggcg tggaggtgca caatgccaag accaagccca gagaggagca gtacaactct 900
acatataggg tggtgagcgt gctgaccgtg ctgcaccagg actggctgaa cggcaaggag 960
tataagtgca aggtgtccaa taaggccctg cccgccccca tcgagaagac aatcagcaag 1020
gccaagggcc agcctcggga gccacaggtg tacaccctgc ctccatccag agacgagctg 1080
acaaagaacc aggtgtctct gacatgtctg gtgaagggct tctatcctag cgatatcgcc 1140
gtggagtggg agtccaatgg ccagccagag aacaattaca agaccacacc ccctgtgctg 1200
gactccgatg gctccttctt tctgtattcc aagctgaccg tggataagtc tcggtggcag 1260
cagggcaacg tgttcagctg ttccgtgatg cacgaagccc tgcataatca ctatactcag 1320
aaatccctgt ccctgtcacc tggaaagtga 1350

<210> SEQ ID NO 19
<211> LENGTH: 1350
<212> TYPE: DNA
<213> ORGANISM: Artificial Sequence
<220> FEATURE:
<223> OTHER INFORMATION: Synthetic - pCDNA3.4-IgG1-VH3

<400> SEQUENCE: 19
caggtgcagc tggtgcagag cggagcagag gtgaagaagc caggagccag cgtgaaggtg 60
tcctgcaagg cctctggcta tacattctcc aactacctga tgaattgggt gcggcaggca 120
ccaggacagg gactggagtg gatgggcagg atcgatcctt atgacggcga tatcgactac 180
aaccagaact tcaaggatcg ggtgaccatg acaagagaca cctccacatc taccgtgtat 240
atggagctga gctccctgag gtctgaggat acagccgtgt actattgtgc aaggggatac 300
ggaaccgcat atggagtgga ctactggggc cagggcacac tggtgaccgt gtctagcgcc 360
agcaccaagg gcccttccgt gtttccactg gccccctcct ctaaatccac atctggcggc 420
accgccgccc tgggctgtct ggtgaaggac tacttcccag agcctgtgac agtgtcctgg 480
aactctggcg ccctgacatc cggcgtgcac acatttccag ccgtgctgca gagctccggc 540
ctgtacagcc tgtctagcgt ggtgacagtg ccctcctcta gcctgggcac acagacctat 600
atctgcaacg tgaatcacaa gccaagcaat accaaggtgg acaagaaggt ggagcccaag 660
tcctgtgata agacacacac ctgccccccct tgtcctgctc ccgagctgct gggcggccct 720
agcgtgttcc tgtttccacc caagcctaag gacaccctga tgatctcccg gacacccgag 780
gtgacctgcg tggtggtgga cgtgtctcac gaggatcctg aggtgaagtt caactggtat 840
gtggatggcg tggaggtgca caatgccaag accaagccca gagaggagca gtacaactct 900
acatataggg tggtgagcgt gctgaccgtg ctgcaccagg actggctgaa cggcaaggag 960
tataagtgca aggtgtccaa taaggccctg cccgccccca tcgagaagac aatcagcaag 1020
gccaagggcc agcctcggga gccacaggtg tacaccctgc ctccatccag agacgagctg 1080
acaaagaacc aggtgtctct gacatgtctg gtgaagggct tctatcctag cgatatcgcc 1140
gtggagtggg agtccaatgg ccagccagag aacaattaca agaccacacc ccctgtgctg 1200
gactccgatg gctccttctt tctgtattcc aagctgaccg tggataagtc tcggtggcag 1260
cagggcaacg tgttcagctg ttccgtgatg cacgaagccc tgcataatca ctatactcag 1320
aaatccctgt ccctgtcacc tggaaagtga 1350

<210> SEQ ID NO 20
<211> LENGTH: 1350
<212> TYPE: DNA
<213> ORGANISM: Artificial Sequence
<220> FEATURE:
<223> OTHER INFORMATION: Synthetic - pCDNA3.4-IgG1-VH4

<400> SEQUENCE: 20
caggtgcagc tggtgcagag cggagcagag gtgaagaagc caggagccag cgtgaaggtg 60
tcctgcaagg cctctggcta taccttctcc aactacctga tgaattgggt gcggcaggca 120
acaggacagg gactggagtg gatgggcagg atcgatcctt atgacggcga tatcgactac 180
aaccagaact tcaaggaccg ggtgaccatc acaagaaaca cctccatctc tacagcctat 240
atggagctga gctccctgag gtctgaggat accgccgtgt actattgtgc aaggggatac 300
ggaacagcat atggagtgga ctactgggga cagggcaccc tggtgacagt gtctagcgcc 360
agcaccaagg gcccttccgt gtttccactg gccccctcct ctaaatccac atctggcggc 420
accgccgccc tgggctgtct ggtgaaggac tacttcccag agcctgtgac agtgtcctgg 480
aactctggcg ccctgacatc cggcgtgcac acatttccag ccgtgctgca gagctccggc 540
ctgtacagcc tgtctagcgt ggtgacagtg ccctcctcta gcctgggcac acagacctat 600
atctgcaacg tgaatcacaa gccaagcaat accaaggtgg acaagaaggt ggagcccaag 660
tcctgtgata agacacacac ctgccccccct tgtcctgctc ccgagctgct gggcggccct 720
agcgtgttcc tgtttccacc caagcctaag gacaccctga tgatctcccg gacacccgag 780
gtgacctgcg tggtggtgga cgtgtctcac gaggatcctg aggtgaagtt caactggtat 840
gtggatggcg tggaggtgca caatgccaag accaagccca gagaggagca gtacaactct 900
acatataggg tggtgagcgt gctgaccgtg ctgcaccagg actggctgaa cggcaaggag 960
tataagtgca aggtgtccaa taaggccctg cccgccccca tcgagaagac aatcagcaag 1020
gccaagggcc agcctcggga gccacaggtg tacaccctgc ctccatccag agacgagctg 1080
acaaagaacc aggtgtctct gacatgtctg gtgaagggct tctatcctag cgatatcgcc 1140
gtggagtggg agtccaatgg ccagccagag aacaattaca agaccacacc ccctgtgctg 1200
gactccgatg gctccttctt tctgtattcc aagctgaccg tggataagtc tcggtggcag 1260
cagggcaacg tgttcagctg ttccgtgatg cacgaagccc tgcataatca ctatactcag 1320
aaatccctgt ccctgtcacc tggaaagtga 1350

<210> SEQ ID NO 21
<211> LENGTH: 657
<212> TYPE: DNA
<213> ORGANISM: Artificial Sequence
<220> FEATURE:
<223> OTHER INFORMATION: Synthetic - pCDNA3.4-IgG1-VL1

<400> SEQUENCE: 21
gacatcgtga tgacccagtc ccctgattct ctggccgtgt ctctgggaga gagggcaaca 60
atcaactgca gagcctctga gagcgtggac aactacggca tcagcttcat gaattggtat 120
cagcagaagc caggccagcc ccctaagctg ctgatctacg cagcaagcag gcagggatcc 180
ggagtgcccg accggttctc cggatctgga agcggaaccg acttcaccct gacaatcagc 240
tccctgcagg ccgaggatgt ggccgtgtac tattgtcagc agtccaagga ggtgccatgg 300
acctttggcg gaggaacaaa gctggagatc aagaggacag tggccgcccc aagcgtgttc 360
atctttcccc cttccgacga gcagctgaag tctggcaccg ccagcgtggt gtgcctgctg 420
aacaacttct accctcggga ggccaaggtc cagtggaagg tggataacgc cctgcagtct 480
ggcaatagcc aggagtccgt gaccgagcag gactctaagg atagcacata ttccctgtct 540
agcaccctga cactgagcaa ggccgattac gagaagcaca aggtgtatgc ctgtgaagtc 600
acccatcagg gcctgtcatc acccgtcact aagtcattca atcgcggaga atgctga 657

<210> SEQ ID NO 22
<211> LENGTH: 657
<212> TYPE: DNA
<213> ORGANISM: Artificial Sequence
<220> FEATURE:
<223> OTHER INFORMATION: Synthetic - pCDNA3.4-IgG1-VL2

<400> SEQUENCE: 22
gacatccaga tgacccagtc tcctagctcc ctgtccgcct ctgtgggcga cagggtgacc 60
atcacatgca gagccagcga gtccgtggat aactacggca tctccttcat gaattggtat 120

```
cagcagaagc ccggcaaggc ccctaagctg ctgatctacg cagcatctag gcagggaagc    180

ggagtgccct cccggttctc tggcagcggc tccggcaccg actttaccct gacaatctct    240

agcctgcagc cagaggattt cgccacatac tattgtcagc agagcaagga ggtgccatgg    300

acctttggcg gaggaacaaa gctggagatc aagaggacag tggccgcccc aagcgtgttc    360

atctttcccc cttccgacga gcagctgaag tctggcaccg ccagcgtggt gtgcctgctg    420

aacaacttct accctcggga ggccaaggtc cagtggaagg tggataacgc cctgcagtct    480

ggcaatagcc aggagtccgt gaccgagcag gactctaagg atagcacata ttccctgtct    540

agcaccctga cactgagcaa ggccgattac gagaagcaca aggtgtatgc ctgtgaagtc    600

acccatcagg ggctgtcatc acccgtcact aagtcattca atcgcggaga atgctga       657
```

```
<210> SEQ ID NO 23
<211> LENGTH: 657
<212> TYPE: DNA
<213> ORGANISM: Artificial Sequence
<220> FEATURE:
<223> OTHER INFORMATION: Synthetic - pCDNA3.4-IgG1-VL3

<400> SEQUENCE: 23

gagatcgtgc tgacccagtc cccagccaca ctgtctctga gcccaggaga gagggccacc     60

ctgtcttgca gagcctccga gtctgtggac aactacggca tcagcttcat gaattggtat    120

cagcagaagc caggacaggc acctaggctg ctgatctacg cagcaagcag gcagggatcc    180

ggaatccccg cccggttcag cggctccggc tctggcacag actttaccct gacaatcagc    240

tccctggagc ctgaggattt cgccgtgtac tattgtcagc agtctaagga ggtgccatgg    300

acctttggcg gcggcacaaa gctggagatc aagaggacag tggccgcccc aagcgtgttc    360

atctttcccc cttccgacga gcagctgaag tctggcaccg ccagcgtggt gtgcctgctg    420

aacaacttct accctcggga ggccaaggtc cagtggaagg tggataacgc cctgcagtct    480

ggcaatagcc aggagtccgt gaccgagcag gactctaagg atagcacata ttccctgtct    540

agcaccctga cactgagcaa ggccgattac gagaagcaca aggtgtatgc ctgtgaagtc    600

acccatcagg ggctgtcatc acccgtcact aagtcattca atcgcggaga atgctga       657
```

```
<210> SEQ ID NO 24
<211> LENGTH: 657
<212> TYPE: DNA
<213> ORGANISM: Artificial Sequence
<220> FEATURE:
<223> OTHER INFORMATION: Synthetic - pCDNA3.4-IgG1-VL4

<400> SEQUENCE: 24

gagatcgtga tgacccagtc cccagccaca ctgtctgtga gcccaggaga gagggccacc     60

ctgtcctgca gagcctccga gtctgtggac aactacggca tctctttcat gaattggtat    120

cagcagaagc caggacaggc acctaggctg ctgatctacg cagcaagcag gcagggatcc    180

ggaatccctg cacggttcag cggatccgga tctggcacag agtttaccct gacaatcagc    240

tccctgcagt ctgaggattt cgccgtgtac tattgtcagc agagcaagga ggtgccatgg    300

acctttggcg gaggaacaaa gctggagatc aagaggacag tggccgcccc aagcgtgttc    360

atctttcccc cttccgacga gcagctgaag tctggcaccg ccagcgtggt gtgcctgctg    420

aacaacttct accctcggga ggccaaggtc cagtggaagg tggataacgc cctgcagtct    480

ggcaatagcc aggagtccgt gaccgagcag gactctaagg atagcacata ttccctgtct    540

agcaccctga cactgagcaa ggccgattac gagaagcaca aggtgtatgc ctgtgaagtc    600
```

acccatcagg ggctgtcatc acccgtcact aagtcattca atcgcggaga atgctga 657

<210> SEQ ID NO 25
<211> LENGTH: 119
<212> TYPE: PRT
<213> ORGANISM: Artificial Sequence
<220> FEATURE:
<223> OTHER INFORMATION: Synthetic - VH region from the original mouse monoclonal antibody (mAb)

<400> SEQUENCE: 25

Gln Val Gln Leu Gln Gln Pro Gly Ala Glu Leu Val Arg Pro Gly Ala
1 5 10 15

Ser Val Lys Leu Ser Cys Lys Ala Ser Gly Tyr Thr Phe Ser Asn Tyr
20 25 30

Leu Met Asn Trp Val Lys Gln Arg Pro Glu Gln Asp Leu Asp Trp Ile
35 40 45

Gly Arg Ile Asp Pro Tyr Asp Gly Asp Ile Asp Tyr Asn Gln Asn Phe
50 55 60

Lys Asp Lys Ala Ile Leu Thr Val Asp Lys Ser Ser Ser Thr Ala Tyr
65 70 75 80

Met Gln Leu Ser Ser Leu Thr Ser Glu Asp Ser Ala Val Tyr Tyr Cys
85 90 95

Ala Arg Gly Tyr Gly Thr Ala Tyr Gly Val Asp Tyr Trp Gly Gln Gly
100 105 110

Thr Ser Val Thr Val Ser Ser
115

<210> SEQ ID NO 26
<211> LENGTH: 111
<212> TYPE: PRT
<213> ORGANISM: Artificial Sequence
<220> FEATURE:
<223> OTHER INFORMATION: Synthetic - VL region from the original mouse monoclonal antibody (mAb)

<400> SEQUENCE: 26

Asp Ile Val Leu Thr Gln Ser Pro Ala Ser Leu Ala Val Ser Leu Gly
1 5 10 15

Gln Arg Ala Thr Ile Ser Cys Arg Ala Ser Glu Ser Val Asp Asn Tyr
20 25 30

Gly Ile Ser Phe Met Asn Trp Phe Gln Gln Lys Pro Gly Gln Pro Pro
35 40 45

Lys Leu Leu Ile Tyr Ala Ala Ser Arg Gln Gly Ser Gly Val Pro Ala
50 55 60

Arg Phe Ser Gly Ser Gly Ser Gly Thr Asp Phe Ser Leu Asn Ile His
65 70 75 80

Pro Met Glu Glu Asp Asp Thr Ala Met Tyr Phe Cys Gln Gln Ser Lys
85 90 95

Glu Val Pro Trp Thr Phe Gly Gly Gly Thr Lys Leu Glu Ile Lys
100 105 110

<210> SEQ ID NO 27
<211> LENGTH: 449
<212> TYPE: PRT
<213> ORGANISM: Artificial Sequence
<220> FEATURE:
<223> OTHER INFORMATION: Synthetic - pCDNA3.4-IgG1-VH1 with D55E mutation -continued

<400> SEQUENCE: 27

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asn Tyr
            20                  25                  30

Leu Met Asn Trp Val Arg Gln Ala Pro Gly Gln Gly Leu Glu Trp Met
        35                  40                  45

Gly Arg Ile Asp Pro Tyr Asp Gly Glu Ile Asp Tyr Asn Gln Asn Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Gly Thr Ala Tyr Gly Val Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 28
<211> LENGTH: 449
<212> TYPE: PRT
<213> ORGANISM: Artificial Sequence
<220> FEATURE:
<223> OTHER INFORMATION: Synthetic - pCDNA3.4-IgG1-VH1 with G56A mutation

<400> SEQUENCE: 28

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Ser Asn Tyr
20 25 30

Leu Met Asn Trp Val Arg Gln Ala Pro Gly Gln Gly Leu Glu Trp Met
35 40 45

Gly Arg Ile Asp Pro Tyr Asp Ala Asp Ile Asp Tyr Asn Gln Asn Phe
50 55 60

Lys Asp Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Tyr Gly Thr Ala Tyr Gly Val Asp Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 29
<211> LENGTH: 19
<212> TYPE: PRT
<213> ORGANISM: Artificial Sequence
<220> FEATURE:
<223> OTHER INFORMATION: Synthetic - Signal sequence from mouse Ig heavy chain V region 102

<400> SEQUENCE: 29

Met Gly Trp Ser Cys Ile Ile Leu Phe Leu Val Ala Thr Ala Thr Gly
1 5 10 15

Val His Ser

<210> SEQ ID NO 30
<211> LENGTH: 468
<212> TYPE: PRT
<213> ORGANISM: Artificial Sequence
<220> FEATURE:
<223> OTHER INFORMATION: Synthetic - pCDNA3.4-IgG1-VH1 with signal sequence

<400> SEQUENCE: 30

Met Gly Trp Ser Cys Ile Ile Leu Phe Leu Val Ala Thr Ala Thr Gly
1 5 10 15

Val His Ser Gln Val Gln Leu Val Gln Ser Gly Ala Glu Val Lys Lys
20 25 30

Pro Gly Ser Ser Val Lys Val Ser Cys Lys Ala Ser Gly Tyr Thr Phe
35 40 45

Ser Asn Tyr Leu Met Asn Trp Val Arg Gln Ala Pro Gly Gln Gly Leu
50 55 60

Glu Trp Met Gly Arg Ile Asp Pro Tyr Asp Gly Asp Ile Asp Tyr Asn
65 70 75 80

Gln Asn Phe Lys Asp Arg Val Thr Ile Thr Ala Asp Lys Ser Thr Ser
85 90 95

Thr Ala Tyr Met Glu Leu Ser Ser Leu Arg Ser Glu Asp Thr Ala Val
100 105 110

Tyr Tyr Cys Ala Arg Gly Tyr Gly Thr Ala Tyr Gly Val Asp Tyr Trp
115 120 125

Gly Gln Gly Thr Leu Val Thr Val Ser Ser Ala Ser Thr Lys Gly Pro

-continued

```
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465


<210> SEQ ID NO 31
<211> LENGTH: 468
<212> TYPE: PRT
<213> ORGANISM: Artificial Sequence
<220> FEATURE:
<223> OTHER INFORMATION: Synthetic - pCDNA3.4-IgG1-VH2 with signal
      sequence

<400> SEQUENCE: 31

Met Gly Trp Ser Cys Ile Ile Leu Phe Leu Val Ala Thr Ala Thr Gly
1               5                   10                  15
```

-continued

```
Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Ser Asn Tyr Leu Met Asn Trp Val Arg Gln Ala Pro Gly Gln Arg Leu
    50                  55                  60

Glu Trp Met Gly Arg Ile Asp Pro Tyr Asp Gly Asp Ile Asp Tyr Asn
65                  70                  75                  80

Gln Asn Phe Lys Asp Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Tyr Gly Thr Ala Tyr Gly Val Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
```

```
        435                 440                 445

Met His Glu Ala Leu His Asn His Tyr Thr Gln Lys Ser Leu Ser Leu
    450                 455                 460

Ser Pro Gly Lys
465


<210> SEQ ID NO 32
<211> LENGTH: 468
<212> TYPE: PRT
<213> ORGANISM: Artificial Sequence
<220> FEATURE:
<223> OTHER INFORMATION: Synthetic - pCDNA3.4-IgG1-VH3 with signal
      sequence

<400> SEQUENCE: 32

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Ser Asn Tyr Leu Met Asn Trp Val Arg Gln Ala Pro Gly Gln Gly Leu
    50                  55                  60

Glu Trp Met Gly Arg Ile Asp Pro Tyr Asp Gly Asp Ile Asp Tyr Asn
65                  70                  75                  80

Gln Asn Phe Lys Asp Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Gly Tyr Gly Thr Ala Tyr Gly Val Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320
```

```
Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465


<210> SEQ ID NO 33
<211> LENGTH: 468
<212> TYPE: PRT
<213> ORGANISM: Artificial Sequence
<220> FEATURE:
<223> OTHER INFORMATION: Synthetic - pCDNA3.4-IgG1-VH4 with signal
      sequence

<400> SEQUENCE: 33

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Ser Asn Tyr Leu Met Asn Trp Val Arg Gln Ala Thr Gly Gln Gly Leu
    50                  55                  60

Glu Trp Met Gly Arg Ile Asp Pro Tyr Asp Gly Asp Ile Asp Tyr Asn
65                  70                  75                  80

Gln Asn Phe Lys Asp Arg Val Thr Ile Thr Arg Asn Thr Ser Ile Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Tyr Gly Thr Ala Tyr Gly Val Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205
```

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 34
<211> LENGTH: 237
<212> TYPE: PRT
<213> ORGANISM: Artificial Sequence
<220> FEATURE:
<223> OTHER INFORMATION: Synthetic - pCDNA3.4-IgG1-VL1 with signal
      sequence

<400> SEQUENCE: 34

Met Gly Trp Ser Cys Ile Ile Leu Phe Leu Val Ala Thr Ala Thr Gly
1               5                   10                  15

Val His Ser Asp Ile Val Met Thr Gln Ser Pro Asp Ser Leu Ala Val
            20                  25                  30

Ser Leu Gly Glu Arg Ala Thr Ile Asn Cys Arg Ala Ser Glu Ser Val
        35                  40                  45

Asp Asn Tyr Gly Ile Ser Phe Met Asn Trp Tyr Gln Gln Lys Pro Gly
    50                  55                  60

Gln Pro Pro Lys Leu Leu Ile Tyr Ala Ala Ser Arg Gln Gly Ser Gly
65                  70                  75                  80

Val Pro Asp Arg Phe Ser Gly Ser Gly Ser Gly Thr Asp Phe Thr Leu

-continued

```
                85                  90                  95

Thr Ile Ser Ser Leu Gln Ala Glu Asp Val Ala Val Tyr Tyr Cys Gln
            100                 105                 110

Gln Ser Lys Glu Val Pro Trp Thr Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235


<210> SEQ ID NO 35
<211> LENGTH: 237
<212> TYPE: PRT
<213> ORGANISM: Artificial Sequence
<220> FEATURE:
<223> OTHER INFORMATION: Synthetic - pCDNA3.4-IgG1-VL2 with signal
      sequence

<400> SEQUENCE: 35

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Glu Ser Val
        35                  40                  45

Asp Asn Tyr Gly Ile Ser Phe Met Asn Trp Tyr Gln Gln Lys Pro Gly
    50                  55                  60

Lys Ala Pro Lys Leu Leu Ile Tyr Ala Ala Ser Arg Gln Gly Ser Gly
65                  70                  75                  80

Val Pro Ser Arg Phe Ser Gly Ser Gly Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln Ser Lys Glu Val Pro Trp Thr Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205
```

```
Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235


<210> SEQ ID NO 36
<211> LENGTH: 237
<212> TYPE: PRT
<213> ORGANISM: Artificial Sequence
<220> FEATURE:
<223> OTHER INFORMATION: Synthetic - pCDNA3.4-IgG1-VL3 with signal
      sequence

<400> SEQUENCE: 36

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Glu Ser Val
        35                  40                  45

Asp Asn Tyr Gly Ile Ser Phe Met Asn Trp Tyr Gln Gln Lys Pro Gly
    50                  55                  60

Gln Ala Pro Arg Leu Leu Ile Tyr Ala Ala Ser Arg Gln Gly Ser Gly
65                  70                  75                  80

Ile Pro Ala Arg Phe Ser Gly Ser Gly Ser Gly Thr Asp Phe Thr Leu
                85                  90                  95

Thr Ile Ser Ser Leu Glu Pro Glu Asp Phe Ala Val Tyr Tyr Cys Gln
            100                 105                 110

Gln Ser Lys Glu Val Pro Trp Thr Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235


<210> SEQ ID NO 37
<211> LENGTH: 237
<212> TYPE: PRT
<213> ORGANISM: Artificial Sequence
<220> FEATURE:
<223> OTHER INFORMATION: Synthetic - pCDNA3.4-IgG1-VL4 with signal
      sequence

<400> SEQUENCE: 37

Met Gly Trp Ser Cys Ile Ile Leu Phe Leu Val Ala Thr Ala Thr Gly
1               5                   10                  15

Val His Ser Glu Ile Val Met Thr Gln Ser Pro Ala Thr Leu Ser Val
            20                  25                  30
```

-continued

```
Ser Pro Gly Glu Arg Ala Thr Leu Ser Cys Arg Ala Ser Glu Ser Val
        35                  40                  45

Asp Asn Tyr Gly Ile Ser Phe Met Asn Trp Tyr Gln Gln Lys Pro Gly
    50                  55                  60

Gln Ala Pro Arg Leu Leu Ile Tyr Ala Ala Ser Arg Gln Gly Ser Gly
65                  70                  75                  80

Ile Pro Ala Arg Phe Ser Gly Ser Gly Ser Gly Thr Glu Phe Thr Leu
                85                  90                  95

Thr Ile Ser Ser Leu Gln Ser Glu Asp Phe Ala Val Tyr Tyr Cys Gln
            100                 105                 110

Gln Ser Lys Glu Val Pro Trp Thr Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235


<210> SEQ ID NO 38
<211> LENGTH: 468
<212> TYPE: PRT
<213> ORGANISM: Artificial Sequence
<220> FEATURE:
<223> OTHER INFORMATION: Synthetic - Generic pCDNA3.4-IgG1-VH1 with
      signal sequence
<220> FEATURE:
<221> NAME/KEY: MISC_FEATURE
<222> LOCATION: (53)..(53)
<223> OTHER INFORMATION: X1 is M, L, A, I, or V
<220> FEATURE:
<221> NAME/KEY: MISC_FEATURE
<222> LOCATION: (71)..(71)
<223> OTHER INFORMATION: X2 is D or E
<220> FEATURE:
<221> NAME/KEY: MISC_FEATURE
<222> LOCATION: (72)..(72)
<223> OTHER INFORMATION: X3 is P or A
<220> FEATURE:
<221> NAME/KEY: MISC_FEATURE
<222> LOCATION: (74)..(74)
<223> OTHER INFORMATION: X4 is D or E
<220> FEATURE:
<221> NAME/KEY: MISC_FEATURE
<222> LOCATION: (75)..(75)
<223> OTHER INFORMATION: X5 is G or A

<400> SEQUENCE: 38

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45
```

-continued

```
Ser Asn Tyr Leu Xaa Asn Trp Val Arg Gln Ala Pro Gly Gln Gly Leu
    50                  55                  60

Glu Trp Met Gly Arg Ile Xaa Xaa Tyr Xaa Xaa Asp Ile Asp Tyr Asn
65                  70                  75                  80

Gln Asn Phe Lys Asp Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Tyr Gly Thr Ala Tyr Gly Val Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
```

465

<210> SEQ ID NO 39
<211> LENGTH: 468
<212> TYPE: PRT
<213> ORGANISM: Artificial Sequence
<220> FEATURE:
<223> OTHER INFORMATION: Synthetic - Generic pCDNA3.4-IgG1-VH2 with signal sequence
<220> FEATURE:
<221> NAME/KEY: MISC_FEATURE
<222> LOCATION: (53)..(53)
<223> OTHER INFORMATION: X1 is M, L, A, I, or V
<220> FEATURE:
<221> NAME/KEY: MISC_FEATURE
<222> LOCATION: (71)..(71)
<223> OTHER INFORMATION: X2 is D or E
<220> FEATURE:
<221> NAME/KEY: MISC_FEATURE
<222> LOCATION: (72)..(72)
<223> OTHER INFORMATION: X3 is P or A
<220> FEATURE:
<221> NAME/KEY: MISC_FEATURE
<222> LOCATION: (74)..(74)
<223> OTHER INFORMATION: X4 is D or E
<220> FEATURE:
<221> NAME/KEY: MISC_FEATURE
<222> LOCATION: (75)..(75)
<223> OTHER INFORMATION: X5 is G or A

<400> SEQUENCE: 39

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Ser Asn Tyr Leu Xaa Asn Trp Val Arg Gln Ala Pro Gly Gln Arg Leu
    50                  55                  60

Glu Trp Met Gly Arg Ile Xaa Xaa Tyr Xaa Xaa Asp Ile Asp Tyr Asn
65                  70                  75                  80

Gln Asn Phe Lys Asp Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Tyr Gly Thr Ala Tyr Gly Val Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
```

```
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465


<210> SEQ ID NO 40
<211> LENGTH: 468
<212> TYPE: PRT
<213> ORGANISM: Artificial Sequence
<220> FEATURE:
<223> OTHER INFORMATION: Synthetic - Generic pCDNA3.4-IgG1-VH3 with
      signal sequence
<220> FEATURE:
<221> NAME/KEY: MISC_FEATURE
<222> LOCATION: (53)..(53)
<223> OTHER INFORMATION: X1 is M, L, A, I, or V
<220> FEATURE:
<221> NAME/KEY: MISC_FEATURE
<222> LOCATION: (71)..(71)
<223> OTHER INFORMATION: X2 is D or E
<220> FEATURE:
<221> NAME/KEY: MISC_FEATURE
<222> LOCATION: (72)..(72)
<223> OTHER INFORMATION: X3 is P or A
<220> FEATURE:
<221> NAME/KEY: MISC_FEATURE
<222> LOCATION: (74)..(74)
<223> OTHER INFORMATION: X4 is D or E
<220> FEATURE:
<221> NAME/KEY: MISC_FEATURE
<222> LOCATION: (75)..(75)
<223> OTHER INFORMATION: X5 is G or A

<400> SEQUENCE: 40

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
```

-continued

```
            20                  25                  30

Pro Gly Ala Ser Val Lys Val Ser Cys Lys Ala Ser Gly Tyr Thr Phe
        35                  40                  45

Ser Asn Tyr Leu Xaa Asn Trp Val Arg Gln Ala Pro Gly Gln Gly Leu
    50                  55                  60

Glu Trp Met Gly Arg Ile Xaa Xaa Tyr Xaa Xaa Asp Ile Asp Tyr Asn
65                  70                  75                  80

Gln Asn Phe Lys Asp Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Gly Tyr Gly Thr Ala Tyr Gly Val Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445
```

```
Met His Glu Ala Leu His Asn His Tyr Thr Gln Lys Ser Leu Ser Leu
    450                 455                 460

Ser Pro Gly Lys
465


<210> SEQ ID NO 41
<211> LENGTH: 468
<212> TYPE: PRT
<213> ORGANISM: Artificial Sequence
<220> FEATURE:
<223> OTHER INFORMATION: Synthetic - Generic pCDNA3.4-IgG1-VH4 with
      signal sequence
<220> FEATURE:
<221> NAME/KEY: MISC_FEATURE
<222> LOCATION: (53)..(53)
<223> OTHER INFORMATION: X1 is M, L, A, I, or V
<220> FEATURE:
<221> NAME/KEY: MISC_FEATURE
<222> LOCATION: (71)..(71)
<223> OTHER INFORMATION: X2 is D or E
<220> FEATURE:
<221> NAME/KEY: MISC_FEATURE
<222> LOCATION: (72)..(72)
<223> OTHER INFORMATION: X3 is P or A
<220> FEATURE:
<221> NAME/KEY: MISC_FEATURE
<222> LOCATION: (74)..(74)
<223> OTHER INFORMATION: X4 is D or E
<220> FEATURE:
<221> NAME/KEY: MISC_FEATURE
<222> LOCATION: (75)..(75)
<223> OTHER INFORMATION: X5 is G or A

<400> SEQUENCE: 41

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Ser Asn Tyr Leu Xaa Asn Trp Val Arg Gln Ala Thr Gly Gln Gly Leu
    50                  55                  60

Glu Trp Met Gly Arg Ile Xaa Xaa Tyr Xaa Xaa Asp Ile Asp Tyr Asn
65                  70                  75                  80

Gln Asn Phe Lys Asp Arg Val Thr Ile Thr Arg Asn Thr Ser Ile Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Tyr Gly Thr Ala Tyr Gly Val Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220
```

-continued

```
His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465


<210> SEQ ID NO 42
<211> LENGTH: 237
<212> TYPE: PRT
<213> ORGANISM: Artificial Sequence
<220> FEATURE:
<223> OTHER INFORMATION: Synthetic - Generic pCDNA3.4-IgG1-VL1 with
      signal sequence
<220> FEATURE:
<221> NAME/KEY: MISC_FEATURE
<222> LOCATION: (56)..(56)
<223> OTHER INFORMATION: X1 is M, L, A, I, or V
<220> FEATURE:
<221> NAME/KEY: MISC_FEATURE
<222> LOCATION: (77)..(77)
<223> OTHER INFORMATION: X2 is Q, E, R, or A
<220> FEATURE:
<221> NAME/KEY: MISC_FEATURE
<222> LOCATION: (113)..(113)
<223> OTHER INFORMATION: X3 is Q, E, R, or A
<220> FEATURE:
<221> NAME/KEY: MISC_FEATURE
<222> LOCATION: (119)..(119)
<223> OTHER INFORMATION: X4 is W, F, or Y

<400> SEQUENCE: 42

Met Gly Trp Ser Cys Ile Ile Leu Phe Leu Val Ala Thr Ala Thr Gly
1               5                   10                  15
```

Val His Ser Asp Ile Val Met Thr Gln Ser Pro Asp Ser Leu Ala Val
20 25 30

Ser Leu Gly Glu Arg Ala Thr Ile Asn Cys Arg Ala Ser Glu Ser Val
35 40 45

Asp Asn Tyr Gly Ile Ser Phe Xaa Asn Trp Tyr Gln Gln Lys Pro Gly
50 55 60

Gln Pro Pro Lys Leu Leu Ile Tyr Ala Ala Ser Arg Xaa Gly Ser Gly
65 70 75 80

Val Pro Asp Arg Phe Ser Gly Ser Gly Ser Gly Thr Asp Phe Thr Leu
85 90 95

Thr Ile Ser Ser Leu Gln Ala Glu Asp Val Ala Val Tyr Tyr Cys Gln
100 105 110

Xaa Ser Lys Glu Val Pro Xaa Thr Phe Gly Gly Gly Thr Lys Leu Glu
115 120 125

Ile Lys Arg Thr Val Ala Ala Pro Ser Val Phe Ile Phe Pro Pro Ser
130 135 140

Asp Glu Gln Leu Lys Ser Gly Thr Ala Ser Val Val Cys Leu Leu Asn
145 150 155 160

Asn Phe Tyr Pro Arg Glu Ala Lys Val Gln Trp Lys Val Asp Asn Ala
165 170 175

Leu Gln Ser Gly Asn Ser Gln Glu Ser Val Thr Glu Gln Asp Ser Lys
180 185 190

Asp Ser Thr Tyr Ser Leu Ser Ser Thr Leu Thr Leu Ser Lys Ala Asp
195 200 205

Tyr Glu Lys His Lys Val Tyr Ala Cys Glu Val Thr His Gln Gly Leu
210 215 220

Ser Ser Pro Val Thr Lys Ser Phe Asn Arg Gly Glu Cys
225 230 235

<210> SEQ ID NO 43
<211> LENGTH: 237
<212> TYPE: PRT
<213> ORGANISM: Artificial Sequence
<220> FEATURE:
<223> OTHER INFORMATION: Synthetic - Generic pCDNA3.4-IgG1-VL2 with signal sequence
<220> FEATURE:
<221> NAME/KEY: MISC_FEATURE
<222> LOCATION: (56)..(56)
<223> OTHER INFORMATION: X1 is M, L, A, I, or V
<220> FEATURE:
<221> NAME/KEY: MISC_FEATURE
<222> LOCATION: (77)..(77)
<223> OTHER INFORMATION: X2 is Q, E, R, or A
<220> FEATURE:
<221> NAME/KEY: MISC_FEATURE
<222> LOCATION: (113)..(113)
<223> OTHER INFORMATION: X3 is Q, E, R, or A
<220> FEATURE:
<221> NAME/KEY: MISC_FEATURE
<222> LOCATION: (119)..(119)
<223> OTHER INFORMATION: X4 is W, F, or Y

<400> SEQUENCE: 43

Met Gly Trp Ser Cys Ile Ile Leu Phe Leu Val Ala Thr Ala Thr Gly
1 5 10 15

Val His Ser Asp Ile Gln Met Thr Gln Ser Pro Ser Ser Leu Ser Ala
20 25 30

Ser Val Gly Asp Arg Val Thr Ile Thr Cys Arg Ala Ser Glu Ser Val
35 40 45

Asp Asn Tyr Gly Ile Ser Phe Xaa Asn Trp Tyr Gln Gln Lys Pro Gly

```
    50                  55                  60

Lys Ala Pro Lys Leu Leu Ile Tyr Ala Ala Ser Arg Xaa Gly Ser Gly
65                  70                  75                  80

Val Pro Ser Arg Phe Ser Gly Ser Gly Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Xaa Ser Lys Glu Val Pro Xaa Thr Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235


<210> SEQ ID NO 44
<211> LENGTH: 237
<212> TYPE: PRT
<213> ORGANISM: Artificial Sequence
<220> FEATURE:
<223> OTHER INFORMATION: Synthetic - Generic pCDNA3.4-IgG1-VL3 with
      signal sequence
<220> FEATURE:
<221> NAME/KEY: MISC_FEATURE
<222> LOCATION: (56)..(56)
<223> OTHER INFORMATION: X1 is M, L, A, I, or V
<220> FEATURE:
<221> NAME/KEY: MISC_FEATURE
<222> LOCATION: (77)..(77)
<223> OTHER INFORMATION: X2 is Q, E, R, or A
<220> FEATURE:
<221> NAME/KEY: MISC_FEATURE
<222> LOCATION: (113)..(113)
<223> OTHER INFORMATION: X3 is Q, E, R, or A
<220> FEATURE:
<221> NAME/KEY: MISC_FEATURE
<222> LOCATION: (119)..(119)
<223> OTHER INFORMATION: X4 is W, F, or Y

<400> SEQUENCE: 44

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Glu Ser Val
        35                  40                  45

Asp Asn Tyr Gly Ile Ser Phe Xaa Asn Trp Tyr Gln Gln Lys Pro Gly
    50                  55                  60

Gln Ala Pro Arg Leu Leu Ile Tyr Ala Ala Ser Arg Xaa Gly Ser Gly
65                  70                  75                  80

Ile Pro Ala Arg Phe Ser Gly Ser Gly Ser Gly Thr Asp Phe Thr Leu
                85                  90                  95
```

```
Thr Ile Ser Ser Leu Glu Pro Glu Asp Phe Ala Val Tyr Tyr Cys Gln
            100                 105                 110

Xaa Ser Lys Glu Val Pro Xaa Thr Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235


<210> SEQ ID NO 45
<211> LENGTH: 237
<212> TYPE: PRT
<213> ORGANISM: Artificial Sequence
<220> FEATURE:
<223> OTHER INFORMATION: Synthetic - Generic pCDNA3.4-IgG1-VL4 with
      signal sequence
<220> FEATURE:
<221> NAME/KEY: MISC_FEATURE
<222> LOCATION: (56)..(56)
<223> OTHER INFORMATION: X1 is M, L, A, I, or V
<220> FEATURE:
<221> NAME/KEY: MISC_FEATURE
<222> LOCATION: (77)..(77)
<223> OTHER INFORMATION: X2 is Q, E, R, or A
<220> FEATURE:
<221> NAME/KEY: MISC_FEATURE
<222> LOCATION: (113)..(113)
<223> OTHER INFORMATION: X3 is Q, E, R, or A
<220> FEATURE:
<221> NAME/KEY: MISC_FEATURE
<222> LOCATION: (119)..(119)
<223> OTHER INFORMATION: X4 is W, F, or Y

<400> SEQUENCE: 45

Met Gly Trp Ser Cys Ile Ile Leu Phe Leu Val Ala Thr Ala Thr Gly
1               5                   10                  15

Val His Ser Glu Ile Val Met Thr Gln Ser Pro Ala Thr Leu Ser Val
            20                  25                  30

Ser Pro Gly Glu Arg Ala Thr Leu Ser Cys Arg Ala Ser Glu Ser Val
        35                  40                  45

Asp Asn Tyr Gly Ile Ser Phe Xaa Asn Trp Tyr Gln Gln Lys Pro Gly
    50                  55                  60

Gln Ala Pro Arg Leu Leu Ile Tyr Ala Ala Ser Arg Xaa Gly Ser Gly
65                  70                  75                  80

Ile Pro Ala Arg Phe Ser Gly Ser Gly Ser Gly Thr Glu Phe Thr Leu
                85                  90                  95

Thr Ile Ser Ser Leu Gln Ser Glu Asp Phe Ala Val Tyr Tyr Cys Gln
            100                 105                 110

Xaa Ser Lys Glu Val Pro Xaa Thr Phe Gly Gly Gly Thr Lys Leu Glu
        115                 120                 125
```

-continued

```
Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 46
<211> LENGTH: 57
<212> TYPE: DNA
<213> ORGANISM: Artificial Sequence
<220> FEATURE:
<223> OTHER INFORMATION: Synthetic - Nucleotide sequence of signal sequence

<400> SEQUENCE: 46

```
atgggctggt catgcattat tctgtttctg gtcgcaactg ctacaggcgt gcatagt        57
```

<210> SEQ ID NO 47
<211> LENGTH: 1605
<212> TYPE: DNA
<213> ORGANISM: Artificial Sequence
<220> FEATURE:
<223> OTHER INFORMATION: Synthetic - Humanized BTE (scFv28F11-23 aa linker-scFv47)

<400> SEQUENCE: 47

```
atgggctggt catgcattat tctgtttctg gtcgcaactg ctacaggcgt gcatagtcag     60

gtgcagctgg tggagtccgg gggaggcgtg gtccagcctg ggaggtccct gagactctcc    120

tgtgcagcgt ctggattcaa gttcagtggc tatggcatgc actgggtccg ccaggctcca    180

ggcaaggggc tggagtgggt ggcagttata tggtatgatg gaagtaagaa atactatgta    240

gactccgtga agggccgctt caccatctcc agagacaatt ccaagaacac gctgtatctg    300

caaatgaaca gcctgagagc cgaggacacg gctgtgtatt actgtgcgag acaaatgggc    360

tactggcact tcgatctctg gggccgtggc accctggtca ctgtctcctc aggtggcggt    420

ggctccggcg gtggtgggtc gggtggcggc ggatctgaaa ttgtgttgac acagtctcca    480

gccaccctgt ctttgtctcc aggggaaaga gccaccctct cctgcagggc cagtcagagt    540

gttagcagct acttagcctg gtaccaacag aaacctggcc aggctcccag gctcctcatc    600

tatgatgcat ccaacagggc cactggcatc ccagccaggt tcagtggcag tgggtctggg    660

acagacttca ctctcaccat cagcagccta gagcctgaag attttgcagt ttattactgt    720

cagcagcgta gcaactggcc tccgctcact ttcggcggag ggaccaaggt ggagatcaaa    780

ggaggcggat ctggcggagg cggatctggc tctggaggcg gatctggcgg aggcggatct    840

ggcggaggcg acatcgtgat gacccagtcc cctgattctc tggccgtgtc tctgggagag    900

agggcaacaa tcaactgcag agcctctgag agcgtggaca actacggcat cagcttcatg    960

aattggtatc agcagaagcc aggccagccc cctaagctgc tgatctacgc agcaagcagg   1020
```

-continued

```
cagggatccg gagtgcccga ccggttctcc ggatctggaa gcggaaccga cttcaccctg   1080

acaatcagct ccctgcaggc cgaggatgtg gccgtgtact attgtcagca gtccaaggag   1140

gtgccatgga cctttggcgg aggaacaaag ctggagatca agggtggcgg tggctccggc   1200

ggtggtgggt cgggtggcgg cggatctcag gtgcagctgg tgcagtccgg agcagaggtg   1260

aagaagccag gaagctccgt gaaggtgtct tgcaaggcca gcggctatac cttctctaac   1320

tacctgatga attgggtgag gcaggcacca ggacagggac tggagtggat gggccgcatc   1380

gatccttatg acggcgatat cgactacaac cagaacttca aggatcgggt gaccatcaca   1440

gccgacaaga gcacctccac agcctatatg gagctgtcta gcctgcggag cgaggatacc   1500

gccgtgtact attgtgccag aggctacggc acagcctatg gagtggacta ctggggacag   1560

ggcaccctgg tgacagtgtc ctctcatcat catcatcatc attga                   1605
```

```
<210> SEQ ID NO 48
<211> LENGTH: 534
<212> TYPE: PRT
<213> ORGANISM: Artificial Sequence
<220> FEATURE:
<223> OTHER INFORMATION: Synthetic - Humanized BTE (scFv28F11-23 aa
      linker-scFv47)

<400> SEQUENCE: 48

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Lys Phe
        35                  40                  45

Ser Gly Tyr Gly Met His Trp Val Arg Gln Ala Pro Gly Lys Gly Leu
    50                  55                  60

Glu Trp Val Ala Val Ile Trp Tyr Asp Gly Ser Lys Lys Tyr Tyr Val
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gln Met Gly Tyr Trp His Phe Asp Leu Trp Gly
        115                 120                 125

Arg Gly Thr Leu Val Thr Val Ser Ser Gly Gly Gly Gly Ser Gly Gly
    130                 135                 140

Gly Gly Ser Gly Gly Gly Gly Ser Glu Ile Val Leu Thr Gln Ser Pro
145                 150                 155                 160

Ala Thr Leu Ser Leu Ser Pro Gly Glu Arg Ala Thr Leu Ser Cys Arg
                165                 170                 175

Ala Ser Gln Ser Val Ser Ser Tyr Leu Ala Trp Tyr Gln Gln Lys Pro
            180                 185                 190

Gly Gln Ala Pro Arg Leu Leu Ile Tyr Asp Ala Ser Asn Arg Ala Thr
        195                 200                 205

Gly Ile Pro Ala Arg Phe Ser Gly Ser Gly Ser Gly Thr Asp Phe Thr
    210                 215                 220

Leu Thr Ile Ser Ser Leu Glu Pro Glu Asp Phe Ala Val Tyr Tyr Cys
225                 230                 235                 240

Gln Gln Arg Ser Asn Trp Pro Pro Leu Thr Phe Gly Gly Gly Thr Lys
                245                 250                 255
```

```
Val Glu Ile Lys Gly Gly Gly Ser Gly Gly Gly Gly Ser Gly Ser Gly
            260                 265                 270

Gly Gly Ser Gly Gly Gly Gly Ser Gly Gly Gly Asp Ile Val Met Thr
        275                 280                 285

Gln Ser Pro Asp Ser Leu Ala Val Ser Leu Gly Glu Arg Ala Thr Ile
    290                 295                 300

Asn Cys Arg Ala Ser Glu Ser Val Asp Asn Tyr Gly Ile Ser Phe Met
305                 310                 315                 320

Asn Trp Tyr Gln Gln Lys Pro Gly Gln Pro Pro Lys Leu Leu Ile Tyr
                325                 330                 335

Ala Ala Ser Arg Gln Gly Ser Gly Val Pro Asp Arg Phe Ser Gly Ser
            340                 345                 350

Gly Ser Gly Thr Asp Phe Thr Leu Thr Ile Ser Ser Leu Gln Ala Glu
        355                 360                 365

Asp Val Ala Val Tyr Tyr Cys Gln Gln Ser Lys Glu Val Pro Trp Thr
    370                 375                 380

Phe Gly Gly Gly Thr Lys Leu Glu Ile Lys Gly Gly Gly Gly Ser Gly
385                 390                 395                 400

Gly Gly Gly Ser Gly Gly Gly Gly Ser Gln Val Gln Leu Val Gln Ser
                405                 410                 415

Gly Ala Glu Val Lys Lys Pro Gly Ser Ser Val Lys Val Ser Cys Lys
            420                 425                 430

Ala Ser Gly Tyr Thr Phe Ser Asn Tyr Leu Met Asn Trp Val Arg Gln
        435                 440                 445

Ala Pro Gly Gln Gly Leu Glu Trp Met Gly Arg Ile Asp Pro Tyr Asp
    450                 455                 460

Gly Asp Ile Asp Tyr Asn Gln Asn Phe Lys Asp Arg Val Thr Ile Thr
465                 470                 475                 480

Ala Asp Lys Ser Thr Ser Thr Ala Tyr Met Glu Leu Ser Ser Leu Arg
                485                 490                 495

Ser Glu Asp Thr Ala Val Tyr Tyr Cys Ala Arg Gly Tyr Gly Thr Ala
            500                 505                 510

Tyr Gly Val Asp Tyr Trp Gly Gln Gly Thr Leu Val Thr Val Ser Ser
        515                 520                 525

His His His His His His
    530
```

<210> SEQ ID NO 49
<211> LENGTH: 534
<212> TYPE: PRT
<213> ORGANISM: Artificial Sequence
<220> FEATURE:
<223> OTHER INFORMATION: Synthetic - Generic humanized BTE
<220> FEATURE:
<221> NAME/KEY: MISC_FEATURE
<222> LOCATION: (383)..(383)
<223> OTHER INFORMATION: X1 is W or F, preferably F
<220> FEATURE:
<221> NAME/KEY: MISC_FEATURE
<222> LOCATION: (464)..(464)
<223> OTHER INFORMATION: X2 is D or E
<220> FEATURE:
<221> NAME/KEY: MISC_FEATURE
<222> LOCATION: (465)..(465)
<223> OTHER INFORMATION: X3 G or A, preferably A

<400> SEQUENCE: 49

```
Met Gly Trp Ser Cys Ile Ile Leu Phe Leu Val Ala Thr Ala Thr Gly
1               5                   10                  15
```

-continued

Val His Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Lys Phe
        35                  40                  45

Ser Gly Tyr Gly Met His Trp Val Arg Gln Ala Pro Gly Lys Gly Leu
    50                  55                  60

Glu Trp Val Ala Val Ile Trp Tyr Asp Gly Ser Lys Lys Tyr Tyr Val
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gln Met Gly Tyr Trp His Phe Asp Leu Trp Gly
        115                 120                 125

Arg Gly Thr Leu Val Thr Val Ser Ser Gly Gly Gly Gly Ser Gly Gly
    130                 135                 140

Gly Gly Ser Gly Gly Gly Gly Ser Glu Ile Val Leu Thr Gln Ser Pro
145                 150                 155                 160

Ala Thr Leu Ser Leu Ser Pro Gly Glu Arg Ala Thr Leu Ser Cys Arg
                165                 170                 175

Ala Ser Gln Ser Val Ser Ser Tyr Leu Ala Trp Tyr Gln Gln Lys Pro
            180                 185                 190

Gly Gln Ala Pro Arg Leu Leu Ile Tyr Asp Ala Ser Asn Arg Ala Thr
        195                 200                 205

Gly Ile Pro Ala Arg Phe Ser Gly Ser Gly Ser Gly Thr Asp Phe Thr
    210                 215                 220

Leu Thr Ile Ser Ser Leu Glu Pro Glu Asp Phe Ala Val Tyr Tyr Cys
225                 230                 235                 240

Gln Gln Arg Ser Asn Trp Pro Pro Leu Thr Phe Gly Gly Gly Thr Lys
                245                 250                 255

Val Glu Ile Lys Gly Gly Gly Ser Gly Gly Gly Gly Ser Gly Ser Gly
            260                 265                 270

Gly Gly Ser Gly Gly Gly Gly Ser Gly Gly Gly Asp Ile Val Met Thr
        275                 280                 285

Gln Ser Pro Asp Ser Leu Ala Val Ser Leu Gly Glu Arg Ala Thr Ile
    290                 295                 300

Asn Cys Arg Ala Ser Glu Ser Val Asp Asn Tyr Gly Ile Ser Phe Met
305                 310                 315                 320

Asn Trp Tyr Gln Gln Lys Pro Gly Gln Pro Pro Lys Leu Leu Ile Tyr
                325                 330                 335

Ala Ala Ser Arg Gln Gly Ser Gly Val Pro Asp Arg Phe Ser Gly Ser
            340                 345                 350

Gly Ser Gly Thr Asp Phe Thr Leu Thr Ile Ser Ser Leu Gln Ala Glu
        355                 360                 365

Asp Val Ala Val Tyr Tyr Cys Gln Gln Ser Lys Glu Val Pro Xaa Thr
    370                 375                 380

Phe Gly Gly Gly Thr Lys Leu Glu Ile Lys Gly Gly Gly Gly Ser Gly
385                 390                 395                 400

Gly Gly Gly Ser Gly Gly Gly Gly Ser Gln Val Gln Leu Val Gln Ser
                405                 410                 415

Gly Ala Glu Val Lys Lys Pro Gly Ser Ser Val Lys Val Ser Cys Lys
            420                 425                 430

Ala Ser Gly Tyr Thr Phe Ser Asn Tyr Leu Met Asn Trp Val Arg Gln

```
        435                 440                 445

Ala Pro Gly Gln Gly Leu Glu Trp Met Gly Arg Ile Asp Pro Tyr Xaa
    450                 455                 460

Xaa Asp Ile Asp Tyr Asn Gln Asn Phe Lys Asp Arg Val Thr Ile Thr
465                 470                 475                 480

Ala Asp Lys Ser Thr Ser Thr Ala Tyr Met Glu Leu Ser Ser Leu Arg
                485                 490                 495

Ser Glu Asp Thr Ala Val Tyr Tyr Cys Ala Arg Gly Tyr Gly Thr Ala
            500                 505                 510

Tyr Gly Val Asp Tyr Trp Gly Gln Gly Thr Leu Val Thr Val Ser Ser
        515                 520                 525

His His His His His His
    530


<210> SEQ ID NO 50
<211> LENGTH: 19
<212> TYPE: PRT
<213> ORGANISM: Artificial Sequence
<220> FEATURE:
<223> OTHER INFORMATION: Synthetic - Leader peptide used in BTE

<400> SEQUENCE: 50

Met Gly Trp Ser Cys Ile Ile Leu Phe Leu Val Ala Thr Ala Thr Gly
1               5                   10                  15

Val His Ser


<210> SEQ ID NO 51
<211> LENGTH: 116
<212> TYPE: PRT
<213> ORGANISM: Artificial Sequence
<220> FEATURE:
<223> OTHER INFORMATION: Synthetic - Heavy chain of 28F11 used in BTE

<400> SEQUENCE: 51

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Lys Phe Ser Gly Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Met Gly Tyr Trp His Phe Asp Leu Trp Gly Arg Gly Thr
            100                 105                 110

Leu Val Thr Val
        115


<210> SEQ ID NO 52
<211> LENGTH: 108
<212> TYPE: PRT
<213> ORGANISM: Artificial Sequence
<220> FEATURE:
<223> OTHER INFORMATION: Synthetic - Light chain of 28F11 used in BTE

<400> SEQUENCE: 52
```

-continued

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Leu Thr Phe Gly Gly Gly Thr Lys Val Glu Ile Lys
            100                 105


<210> SEQ ID NO 53
<211> LENGTH: 111
<212> TYPE: PRT
<213> ORGANISM: Artificial Sequence
<220> FEATURE:
<223> OTHER INFORMATION: Synthetic - Humanized light chain of
      scFvIL13Ra2 used in BTE
<220> FEATURE:
<221> NAME/KEY: MISC_FEATURE
<222> LOCATION: (100)..(100)
<223> OTHER INFORMATION: X1 is W or F

<400> SEQUENCE: 53

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Ile Ser Phe Met Asn Trp Tyr Gln Gln Lys Pro Gly Gln Pro Pro
        35                  40                  45

Lys Leu Leu Ile Tyr Ala Ala Ser Arg Gln Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Val Pro Xaa Thr Phe Gly Gly Gly Thr Lys Leu Glu Ile Lys
            100                 105                 110


<210> SEQ ID NO 54
<211> LENGTH: 119
<212> TYPE: PRT
<213> ORGANISM: Artificial Sequence
<220> FEATURE:
<223> OTHER INFORMATION: Synthetic - Humanized heavy chain of
      scFvIL13Ra2 used in BTE
<220> FEATURE:
<221> NAME/KEY: MISC_FEATURE
<222> LOCATION: (55)..(55)
<223> OTHER INFORMATION: X2 is D or E
<220> FEATURE:
<221> NAME/KEY: MISC_FEATURE
<222> LOCATION: (56)..(56)
<223> OTHER INFORMATION: X3 is G or A

<400> SEQUENCE: 54

Gln Val Gln Leu Val Gln Ser Gly Ala Glu Val Lys Lys Pro Gly Ser
1               5                   10                  15
```

-continued

```
Ser Val Lys Val Ser Cys Lys Ala Ser Gly Tyr Thr Phe Ser Asn Tyr
            20                  25                  30

Leu Met Asn Trp Val Arg Gln Ala Pro Gly Gln Gly Leu Glu Trp Met
        35                  40                  45

Gly Arg Ile Asp Pro Tyr Xaa Xaa Asp Ile Asp Tyr Asn Gln Asn Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Gly Thr Ala Tyr Gly Val Asp Tyr Trp Gly Gln Gly
            100                 105                 110

Thr Leu Val Thr Val Ser Ser
        115


<210> SEQ ID NO 55
<211> LENGTH: 15
<212> TYPE: PRT
<213> ORGANISM: Artificial Sequence
<220> FEATURE:
<223> OTHER INFORMATION: Synthetic - Gly4 S linker used in BTE (linker 1
      or 3)

<400> SEQUENCE: 55

Gly Gly Gly Gly Ser Gly Gly Gly Gly Ser Gly Gly Gly Gly Ser
1               5                   10                  15


<210> SEQ ID NO 56
<211> LENGTH: 23
<212> TYPE: PRT
<213> ORGANISM: Artificial Sequence
<220> FEATURE:
<223> OTHER INFORMATION: Synthetic - Linker 2 used in BTE

<400> SEQUENCE: 56

Gly Gly Gly Ser Gly Gly Gly Gly Ser Gly Ser Gly Gly Gly Ser Gly
1               5                   10                  15

Gly Gly Gly Ser Gly Gly Gly
            20


<210> SEQ ID NO 57
<211> LENGTH: 534
<212> TYPE: PRT
<213> ORGANISM: Artificial Sequence
<220> FEATURE:
<223> OTHER INFORMATION: Synthetic - Humanized BTE with G56A mutation

<400> SEQUENCE: 57

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Lys Phe
        35                  40                  45

Ser Gly Tyr Gly Met His Trp Val Arg Gln Ala Pro Gly Lys Gly Leu
    50                  55                  60

Glu Trp Val Ala Val Ile Trp Tyr Asp Gly Ser Lys Lys Tyr Tyr Val
65                  70                  75                  80

Asp Ser Val Lys Gly Arg Phe Thr Ile Ser Arg Asp Asn Ser Lys Asn
                85                  90                  95
```

```
Thr Leu Tyr Leu Gln Met Asn Ser Leu Arg Ala Glu Asp Thr Ala Val
            100                 105                 110

Tyr Tyr Cys Ala Arg Gln Met Gly Tyr Trp His Phe Asp Leu Trp Gly
        115                 120                 125

Arg Gly Thr Leu Val Thr Val Ser Ser Gly Gly Gly Gly Ser Gly Gly
    130                 135                 140

Gly Gly Ser Gly Gly Gly Gly Ser Glu Ile Val Leu Thr Gln Ser Pro
145                 150                 155                 160

Ala Thr Leu Ser Leu Ser Pro Gly Glu Arg Ala Thr Leu Ser Cys Arg
                165                 170                 175

Ala Ser Gln Ser Val Ser Ser Tyr Leu Ala Trp Tyr Gln Gln Lys Pro
            180                 185                 190

Gly Gln Ala Pro Arg Leu Leu Ile Tyr Asp Ala Ser Asn Arg Ala Thr
        195                 200                 205

Gly Ile Pro Ala Arg Phe Ser Gly Ser Gly Ser Gly Thr Asp Phe Thr
    210                 215                 220

Leu Thr Ile Ser Ser Leu Glu Pro Glu Asp Phe Ala Val Tyr Tyr Cys
225                 230                 235                 240

Gln Gln Arg Ser Asn Trp Pro Pro Leu Thr Phe Gly Gly Gly Thr Lys
                245                 250                 255

Val Glu Ile Lys Gly Gly Gly Ser Gly Gly Gly Gly Ser Gly Ser Gly
            260                 265                 270

Gly Gly Ser Gly Gly Gly Gly Ser Gly Gly Gly Asp Ile Val Met Thr
        275                 280                 285

Gln Ser Pro Asp Ser Leu Ala Val Ser Leu Gly Glu Arg Ala Thr Ile
    290                 295                 300

Asn Cys Arg Ala Ser Glu Ser Val Asp Asn Tyr Gly Ile Ser Phe Met
305                 310                 315                 320

Asn Trp Tyr Gln Gln Lys Pro Gly Gln Pro Pro Lys Leu Leu Ile Tyr
                325                 330                 335

Ala Ala Ser Arg Gln Gly Ser Gly Val Pro Asp Arg Phe Ser Gly Ser
            340                 345                 350

Gly Ser Gly Thr Asp Phe Thr Leu Thr Ile Ser Ser Leu Gln Ala Glu
        355                 360                 365

Asp Val Ala Val Tyr Tyr Cys Gln Gln Ser Lys Glu Val Pro Trp Thr
    370                 375                 380

Phe Gly Gly Gly Thr Lys Leu Glu Ile Lys Gly Gly Gly Gly Ser Gly
385                 390                 395                 400

Gly Gly Gly Ser Gly Gly Gly Gly Ser Gln Val Gln Leu Val Gln Ser
                405                 410                 415

Gly Ala Glu Val Lys Lys Pro Gly Ser Ser Val Lys Val Ser Cys Lys
            420                 425                 430

Ala Ser Gly Tyr Thr Phe Ser Asn Tyr Leu Met Asn Trp Val Arg Gln
        435                 440                 445

Ala Pro Gly Gln Gly Leu Glu Trp Met Gly Arg Ile Asp Pro Tyr Asp
    450                 455                 460

Ala Asp Ile Asp Tyr Asn Gln Asn Phe Lys Asp Arg Val Thr Ile Thr
465                 470                 475                 480

Ala Asp Lys Ser Thr Ser Thr Ala Tyr Met Glu Leu Ser Ser Leu Arg
                485                 490                 495

Ser Glu Asp Thr Ala Val Tyr Tyr Cys Ala Arg Gly Tyr Gly Thr Ala
            500                 505                 510

Tyr Gly Val Asp Tyr Trp Gly Gln Gly Thr Leu Val Thr Val Ser Ser
```

```
        515                 520                 525

His His His His His His
    530


<210> SEQ ID NO 58
<211> LENGTH: 534
<212> TYPE: PRT
<213> ORGANISM: Artificial Sequence
<220> FEATURE:
<223> OTHER INFORMATION: Synthetic - Humanized BTE with W100F and G56A
      mutations

<400> SEQUENCE: 58

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Lys Phe
        35                  40                  45

Ser Gly Tyr Gly Met His Trp Val Arg Gln Ala Pro Gly Lys Gly Leu
    50                  55                  60

Glu Trp Val Ala Val Ile Trp Tyr Asp Gly Ser Lys Lys Tyr Tyr Val
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gln Met Gly Tyr Trp His Phe Asp Leu Trp Gly
        115                 120                 125

Arg Gly Thr Leu Val Thr Val Ser Ser Gly Gly Gly Gly Ser Gly Gly
    130                 135                 140

Gly Gly Ser Gly Gly Gly Gly Ser Glu Ile Val Leu Thr Gln Ser Pro
145                 150                 155                 160

Ala Thr Leu Ser Leu Ser Pro Gly Glu Arg Ala Thr Leu Ser Cys Arg
                165                 170                 175

Ala Ser Gln Ser Val Ser Ser Tyr Leu Ala Trp Tyr Gln Gln Lys Pro
            180                 185                 190

Gly Gln Ala Pro Arg Leu Leu Ile Tyr Asp Ala Ser Asn Arg Ala Thr
        195                 200                 205

Gly Ile Pro Ala Arg Phe Ser Gly Ser Gly Ser Gly Thr Asp Phe Thr
    210                 215                 220

Leu Thr Ile Ser Ser Leu Glu Pro Glu Asp Phe Ala Val Tyr Tyr Cys
225                 230                 235                 240

Gln Gln Arg Ser Asn Trp Pro Pro Leu Thr Phe Gly Gly Gly Thr Lys
                245                 250                 255

Val Glu Ile Lys Gly Gly Gly Ser Gly Gly Gly Gly Ser Gly Ser Gly
            260                 265                 270

Gly Gly Ser Gly Gly Gly Gly Ser Gly Gly Gly Asp Ile Val Met Thr
        275                 280                 285

Gln Ser Pro Asp Ser Leu Ala Val Ser Leu Gly Glu Arg Ala Thr Ile
    290                 295                 300

Asn Cys Arg Ala Ser Glu Ser Val Asp Asn Tyr Gly Ile Ser Phe Met
305                 310                 315                 320

Asn Trp Tyr Gln Gln Lys Pro Gly Gln Pro Pro Lys Leu Leu Ile Tyr
                325                 330                 335
```

```
Ala Ala Ser Arg Gln Gly Ser Gly Val Pro Asp Arg Phe Ser Gly Ser
            340                 345                 350

Gly Ser Gly Thr Asp Phe Thr Leu Thr Ile Ser Ser Leu Gln Ala Glu
        355                 360                 365

Asp Val Ala Val Tyr Tyr Cys Gln Gln Ser Lys Glu Val Pro Phe Thr
    370                 375                 380

Phe Gly Gly Gly Thr Lys Leu Glu Ile Lys Gly Gly Gly Gly Ser Gly
385                 390                 395                 400

Gly Gly Gly Ser Gly Gly Gly Gly Ser Gln Val Gln Leu Val Gln Ser
                405                 410                 415

Gly Ala Glu Val Lys Lys Pro Gly Ser Ser Val Lys Val Ser Cys Lys
            420                 425                 430

Ala Ser Gly Tyr Thr Phe Ser Asn Tyr Leu Met Asn Trp Val Arg Gln
        435                 440                 445

Ala Pro Gly Gln Gly Leu Glu Trp Met Gly Arg Ile Asp Pro Tyr Asp
    450                 455                 460

Ala Asp Ile Asp Tyr Asn Gln Asn Phe Lys Asp Arg Val Thr Ile Thr
465                 470                 475                 480

Ala Asp Lys Ser Thr Ser Thr Ala Tyr Met Glu Leu Ser Ser Leu Arg
                485                 490                 495

Ser Glu Asp Thr Ala Val Tyr Tyr Cys Ala Arg Gly Tyr Gly Thr Ala
            500                 505                 510

Tyr Gly Val Asp Tyr Trp Gly Gln Gly Thr Leu Val Thr Val Ser Ser
        515                 520                 525

His His His His His His
    530


<210> SEQ ID NO 59
<211> LENGTH: 534
<212> TYPE: PRT
<213> ORGANISM: Artificial Sequence
<220> FEATURE:
<223> OTHER INFORMATION: Synthetic - Humanized BTE with W100F and D55E
      mutations

<400> SEQUENCE: 59

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Lys Phe
        35                  40                  45

Ser Gly Tyr Gly Met His Trp Val Arg Gln Ala Pro Gly Lys Gly Leu
    50                  55                  60

Glu Trp Val Ala Val Ile Trp Tyr Asp Gly Ser Lys Lys Tyr Tyr Val
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gln Met Gly Tyr Trp His Phe Asp Leu Trp Gly
        115                 120                 125

Arg Gly Thr Leu Val Thr Val Ser Ser Gly Gly Gly Gly Ser Gly Gly
    130                 135                 140

Gly Gly Ser Gly Gly Gly Gly Ser Glu Ile Val Leu Thr Gln Ser Pro
145                 150                 155                 160
```

```
Ala Thr Leu Ser Leu Ser Pro Gly Glu Arg Ala Thr Leu Ser Cys Arg
                165                 170                 175

Ala Ser Gln Ser Val Ser Ser Tyr Leu Ala Trp Tyr Gln Gln Lys Pro
            180                 185                 190

Gly Gln Ala Pro Arg Leu Leu Ile Tyr Asp Ala Ser Asn Arg Ala Thr
        195                 200                 205

Gly Ile Pro Ala Arg Phe Ser Gly Ser Gly Ser Gly Thr Asp Phe Thr
    210                 215                 220

Leu Thr Ile Ser Ser Leu Glu Pro Glu Asp Phe Ala Val Tyr Tyr Cys
225                 230                 235                 240

Gln Gln Arg Ser Asn Trp Pro Pro Leu Thr Phe Gly Gly Gly Thr Lys
                245                 250                 255

Val Glu Ile Lys Gly Gly Gly Ser Gly Gly Gly Gly Ser Gly Ser Gly
            260                 265                 270

Gly Gly Ser Gly Gly Gly Gly Ser Gly Gly Gly Asp Ile Val Met Thr
        275                 280                 285

Gln Ser Pro Asp Ser Leu Ala Val Ser Leu Gly Glu Arg Ala Thr Ile
    290                 295                 300

Asn Cys Arg Ala Ser Glu Ser Val Asp Asn Tyr Gly Ile Ser Phe Met
305                 310                 315                 320

Asn Trp Tyr Gln Gln Lys Pro Gly Gln Pro Pro Lys Leu Leu Ile Tyr
                325                 330                 335

Ala Ala Ser Arg Gln Gly Ser Gly Val Pro Asp Arg Phe Ser Gly Ser
            340                 345                 350

Gly Ser Gly Thr Asp Phe Thr Leu Thr Ile Ser Ser Leu Gln Ala Glu
        355                 360                 365

Asp Val Ala Val Tyr Tyr Cys Gln Gln Ser Lys Glu Val Pro Phe Thr
    370                 375                 380

Phe Gly Gly Gly Thr Lys Leu Glu Ile Lys Gly Gly Gly Gly Ser Gly
385                 390                 395                 400

Gly Gly Gly Ser Gly Gly Gly Gly Ser Gln Val Gln Leu Val Gln Ser
                405                 410                 415

Gly Ala Glu Val Lys Lys Pro Gly Ser Ser Val Lys Val Ser Cys Lys
            420                 425                 430

Ala Ser Gly Tyr Thr Phe Ser Asn Tyr Leu Met Asn Trp Val Arg Gln
        435                 440                 445

Ala Pro Gly Gln Gly Leu Glu Trp Met Gly Arg Ile Asp Pro Tyr Glu
    450                 455                 460

Gly Asp Ile Asp Tyr Asn Gln Asn Phe Lys Asp Arg Val Thr Ile Thr
465                 470                 475                 480

Ala Asp Lys Ser Thr Ser Thr Ala Tyr Met Glu Leu Ser Ser Leu Arg
                485                 490                 495

Ser Glu Asp Thr Ala Val Tyr Tyr Cys Ala Arg Gly Tyr Gly Thr Ala
            500                 505                 510

Tyr Gly Val Asp Tyr Trp Gly Gln Gly Thr Leu Val Thr Val Ser Ser
        515                 520                 525

His His His His His His
    530
```

<210> SEQ ID NO 60
<211> LENGTH: 534
<212> TYPE: PRT
<213> ORGANISM: Artificial Sequence
<220> FEATURE:

-continued

<223> OTHER INFORMATION: Synthetic - Humanized BTE with W100F, D55E, and
G56A mutations

<400> SEQUENCE: 60

Met Gly Trp Ser Cys Ile Ile Leu Phe Leu Val Ala Thr Ala Thr Gly
1 5 10 15

Val His Ser Gln Val Gln Leu Val Glu Ser Gly Gly Gly Val Val Gln
20 25 30

Pro Gly Arg Ser Leu Arg Leu Ser Cys Ala Ala Ser Gly Phe Lys Phe
35 40 45

Ser Gly Tyr Gly Met His Trp Val Arg Gln Ala Pro Gly Lys Gly Leu
50 55 60

Glu Trp Val Ala Val Ile Trp Tyr Asp Gly Ser Lys Lys Tyr Tyr Val
65 70 75 80

Asp Ser Val Lys Gly Arg Phe Thr Ile Ser Arg Asp Asn Ser Lys Asn
85 90 95

Thr Leu Tyr Leu Gln Met Asn Ser Leu Arg Ala Glu Asp Thr Ala Val
100 105 110

Tyr Tyr Cys Ala Arg Gln Met Gly Tyr Trp His Phe Asp Leu Trp Gly
115 120 125

Arg Gly Thr Leu Val Thr Val Ser Ser Gly Gly Gly Gly Ser Gly Gly
130 135 140

Gly Gly Ser Gly Gly Gly Gly Ser Glu Ile Val Leu Thr Gln Ser Pro
145 150 155 160

Ala Thr Leu Ser Leu Ser Pro Gly Glu Arg Ala Thr Leu Ser Cys Arg
165 170 175

Ala Ser Gln Ser Val Ser Ser Tyr Leu Ala Trp Tyr Gln Gln Lys Pro
180 185 190

Gly Gln Ala Pro Arg Leu Leu Ile Tyr Asp Ala Ser Asn Arg Ala Thr
195 200 205

Gly Ile Pro Ala Arg Phe Ser Gly Ser Gly Ser Gly Thr Asp Phe Thr
210 215 220

Leu Thr Ile Ser Ser Leu Glu Pro Glu Asp Phe Ala Val Tyr Tyr Cys
225 230 235 240

Gln Gln Arg Ser Asn Trp Pro Pro Leu Thr Phe Gly Gly Gly Thr Lys
245 250 255

Val Glu Ile Lys Gly Gly Gly Ser Gly Gly Gly Gly Ser Gly Ser Gly
260 265 270

Gly Gly Ser Gly Gly Gly Gly Ser Gly Gly Gly Asp Ile Val Met Thr
275 280 285

Gln Ser Pro Asp Ser Leu Ala Val Ser Leu Gly Glu Arg Ala Thr Ile
290 295 300

Asn Cys Arg Ala Ser Glu Ser Val Asp Asn Tyr Gly Ile Ser Phe Met
305 310 315 320

Asn Trp Tyr Gln Gln Lys Pro Gly Gln Pro Pro Lys Leu Leu Ile Tyr
325 330 335

Ala Ala Ser Arg Gln Gly Ser Gly Val Pro Asp Arg Phe Ser Gly Ser
340 345 350

Gly Ser Gly Thr Asp Phe Thr Leu Thr Ile Ser Ser Leu Gln Ala Glu
355 360 365

Asp Val Ala Val Tyr Tyr Cys Gln Gln Ser Lys Glu Val Pro Phe Thr
370 375 380

Phe Gly Gly Gly Thr Lys Leu Glu Ile Lys Gly Gly Gly Gly Ser Gly
385 390 395 400

```
Gly Gly Gly Ser Gly Gly Gly Gly Ser Gln Val Gln Leu Val Gln Ser
                405                 410                 415

Gly Ala Glu Val Lys Lys Pro Gly Ser Ser Val Lys Val Ser Cys Lys
            420                 425                 430

Ala Ser Gly Tyr Thr Phe Ser Asn Tyr Leu Met Asn Trp Val Arg Gln
        435                 440                 445

Ala Pro Gly Gln Gly Leu Glu Trp Met Gly Arg Ile Asp Pro Tyr Glu
    450                 455                 460

Ala Asp Ile Asp Tyr Asn Gln Asn Phe Lys Asp Arg Val Thr Ile Thr
465                 470                 475                 480

Ala Asp Lys Ser Thr Ser Thr Ala Tyr Met Glu Leu Ser Ser Leu Arg
                485                 490                 495

Ser Glu Asp Thr Ala Val Tyr Tyr Cys Ala Arg Gly Tyr Gly Thr Ala
            500                 505                 510

Tyr Gly Val Asp Tyr Trp Gly Gln Gly Thr Leu Val Thr Val Ser Ser
        515                 520                 525

His His His His His His
    530
```

<210> SEQ ID NO 61
<211> LENGTH: 354
<212> TYPE: DNA
<213> ORGANISM: Artificial Sequence
<220> FEATURE:
<223> OTHER INFORMATION: Synthetic - 28F11 VH nucleotide sequence

<400> SEQUENCE: 61

```
caggtgcagc tggtggagtc cgggggaggc gtggtccagc ctgggaggtc cctgagactc     60

tcctgtgcag cgtctggatt caagttcagt ggctatggca tgcactgggt ccgccaggct    120

ccaggcaagg ggctggagtg ggtggcagtt atatggtatg atggaagtaa gaaatactat    180

gtagactccg tgaagggccg cttcaccatc tccagagaca attccaagaa cacgctgtat    240

ctgcaaatga acagcctgag agccgaggac acggctgtgt attactgtgc gagacaaatg    300

ggctactggc acttcgatct ctggggccgt ggcaccctgg tcactgtctc ctca          354
```

<210> SEQ ID NO 62
<211> LENGTH: 324
<212> TYPE: DNA
<213> ORGANISM: Artificial Sequence
<220> FEATURE:
<223> OTHER INFORMATION: Synthetic - 28F11 VL nucleotide sequence

<400> SEQUENCE: 62

```
gaaattgtgt tgacacagtc tccagccacc ctgtctttgt ctccagggga aagagccacc     60

ctctcctgca gggccagtca gagtgttagc agctacttag cctggtacca acagaaacct    120

ggccaggctc ccaggctcct catctatgat gcatccaaca gggccactgg catcccagcc    180

aggttcagtg gcagtgggtc tgggacagac ttcactctca ccatcagcag cctagagcct    240

gaagattttg cagtttatta ctgtcagcag cgtagcaact ggcctccgct cactttcggc    300

ggagggacca aggtggagat caaa                                           324
```

HUMANIZED ANTIBODY TARGETING THE TUMOR ASSOCIATED ANTIGEN IL13RA2

CROSS-REFERENCE TO RELATED APPLICATIONS

This application is a U.S. national stage application filed under 35 U.S.C. § 371 of International Application No. PCT/US2021/070377, filed on Apr. 12, 2021, which claims priority to U.S. Provisional Application No. 63/008,681, filed on Apr. 11, 2020, the contents of which are incorporated by reference in their entireties.

STATEMENT REGARDING FEDERALLY SPONSORED RESEARCH

This invention was made with government support under grant number CA221747 and grant number NS101150 awarded by the National Institutes of Health (NIH). The government has certain rights in this invention.

SEQUENCE LISTING

A Sequence Listing accompanies this application and is submitted as an ASCII text file of the sequence listing named "702581_01901_ST25.txt" which is 159 KB in size and was created on Apr. 9, 2021. The sequence listing is electronically submitted via EFS-Web with the application and is incorporated herein by reference in its entirety.

BACKGROUND

Each year, tens of millions of people are diagnosed with cancer around the world, and more than half of them will eventually die from it. There is a search for new and effective cancer treatments. The selective killing of an individual cancer cells is desirable for cancer therapy where the goal of the treatment is for specifically targeting and killing tumor cells, while leaving healthy cells and tissues intact and undamaged. Antibodies that are able to deliver a drug or chemotoxic agent to cells are one avenue of research in cancer therapies. Further, methods of activating the cytotoxic immune response to tumor cells is being highly investigated for cancer treatments, including bispecific antibodies that can activate immune cells to destroy cancer cells. Bispecific antibodies designed to bind with one "arm" to a surface antigen on target cells, and with the second "arm" to an activating, invariant component of the T cell receptor (TCR) complex are under investigation as cancer therapeutics. Simultaneous binding to both of its targets forces a temporary interaction between target cell and T cell, causing activation of any cytotoxic T cell and subsequent lysis of the target cell, i.e. cancer cell.

Glioblastoma, also known as glioblastoma multiforme (GBM), is the most aggressive type of brain cancer. Despite recent advances in treatment, GBM remains largely incurable. The typical duration of survival following a GBM diagnosis is 12 to 15 months. Routine treatment of newly diagnosed GBM consists of surgical resection, chemotherapy, and radiation, which results in a median GBM patient survival of less than two years, with just 5% of patients surviving beyond five years. The blood-brain barrier (BBB) limits therapeutic access to the tumor. An immunosuppressive microenvironment and molecular heterogeneity of GBM present a unique set of challenges for developing effective therapies for this type of brain tumor.

The development of treatments for lessening the immunosuppressive effects of GBM represents an active area of preclinical and clinical neuro-oncology research. Many, if not all, approaches being tested involve increasing T cell cytotoxic antitumor activity. Large numbers of functional cytotoxic tumor-infiltrating lymphocytes (TILs) correlate with improved progression-free survival for GBM patients. However, the immunosuppressive milieu of GBM impairs T cell cytolytic function, altering the effectiveness of T cell-based therapies for treating GBM. Numerous lymphocyte-directed treatments are being investigated, including the use of bispecific T cell engagers (BTE). BTEs can be produced and used without patient specific individualization and can, therefore, be considered "off-the-shelf" therapeutics. The use of BTEs targeting tumor-associated antigens (TAAs) has been approved by the Food and Drug Administration (FDA) in treating liquid malignancies, and BTE-associated treatments are currently being evaluated in multiple clinical studies for solid tumors (e.g., NCT03792841, NCT04117958, NCT03319940). BTEs consist of two single-chain variable fragments (scFvs) connected by a flexible linker. The specificity of BTE's tumor antigen-directed scFv is imperative to harness the full therapeutic potential of the recombinant molecule. BTE anti-cancer activity requires BTE binding with malignant and immune cells simultaneously; single-arm binding to a tumor antigen or CD3ε is therapeutically ineffective. However, the efficacy of the BTEs depends on the targeting ability and specificity to tumor cells.

Thus, there is an unmet need for effective therapeutic strategies for the treatment of GBM and targeting molecules that have specificity and affinity for the tumor cells to allow for specific killing of tumor cells.

SUMMARY

The present disclosure provides engineered humanized and bispecific antibodies capable of binding IL13Rα2, compositions and methods of use for treating cancer, particularly glioblastoma.

In one aspect, the present disclosure provides a humanized antibody that binds to IL13Rα2 comprising: a variable light domain ($V_L$) comprising an amino acid sequence of SEQ ID NO:53 or an amino acid with at least 95% sequence similarity to SEQ ID NO:53; and a variable heavy domain ($V_H$) comprising an amino acid sequence of SEQ ID NO:54 or an amino acid with at least 95% sequence similarity to SEQ ID NO:54. The humanized antibody may have one or more mutation that improves the stability and the affinity of the antibody for IL13Rα2. In some aspects, the humanized antibody is a single chain antibody.

The present disclosure provides in another aspect, a humanized antibody that binds IL13Rα2 comprising: (a) a variable heavy domain ($V_H$) comprising SEQ ID NO:1, SEQ ID NO:2, SEQ ID NO:3, SEQ ID NO:4, SEQ ID NO:9, SEQ ID NO:10, SEQ ID NO:11, SEQ ID NO:12, or an amino acid sequence having at least 95% sequence similarity to SEQ ID NO:1-4 or SEQ ID NO:9-12; and (b) a variable light domain ($V_L$) comprising SEQ ID NO:5, SEQ ID NO:6, SEQ ID NO:7, SEQ ID NO:8, SEQ ID NO:13, SEQ ID NO:14, SEQ ID NO:15, SEQ ID NO:16, or an amino acid sequence having at least 95% sequence similarity to SEQ ID NO:5-8 or SEQ ID NO:13-16.

In another aspect, the present disclosure provides a humanized antibody comprises:

(i) a $V_H$ selected from the group consisting of SEQ ID NO:9, SEQ ID NO:10, SEQ ID NO:11, and SEQ ID NO:12, wherein the $V_H$ has one or more mutations selected from M34L, M34A, M34I, M34V, D52E, P53A, D55E, and G56A; and (ii) a $V_L$ comprising the amino acid sequence selected from the group consisting of SEQ ID NO:13, SEQ ID NO:14, SEQ ID NO:15, and SEQ ID NO:16, wherein the $V_L$ comprising one or more mutations selected from M37L, M37I, M37V, Q58R, Q58A, Q94E, Q94R, Q94A, W100F, and W100Y.

In a further aspect, the present disclosure provides a humanized antibody, wherein the antibody cannot isomerize and comprises: (i) a $V_H$ selected from SEQ ID NO:9, SEQ ID NO:10, SEQ ID NO:11, or SEQ ID NO:12 wherein the $V_H$ comprises G56A, and a $V_L$ selected from SEQ ID NO:5, SEQ ID NO:6, SEQ ID NO:7, SEQ ID NO:8, SEQ ID NO:13, SEQ ID NO:14, SEQ ID NO:15, or SEQ ID NO:16; or (ii) a $V_H$ selected from SEQ ID NO:9, SEQ ID NO:10, SEQ ID NO:11, or SEQ ID NO:12 wherein the $V_H$ comprises D55E, and a $V_L$ selected from SEQ ID NO:5, SEQ ID NO:6, SEQ ID NO:7, SEQ ID NO:8, SEQ ID NO:13, SEQ ID NO:14, SEQ ID NO:15, or SEQ ID NO:16.

In a further aspect, the disclosure provides a composition comprising the humanized antibody of any one of the preceding claims and a pharmaceutically acceptable carrier.

In another aspect, the disclosure provides a method of treating an IL13Rα2-expressing cancer in a subject, the method comprising: administering a therapeutically effective amount of the humanized antibody or the composition described herein to treat the cancer.

In yet another aspect, the disclosure provides a engineered bispecific antibody comprising a first single-chain variable fragment (scFv) that binds to CD3 and a second scFv that binds to IL13Rα2, wherein the first scFv comprises: (a) a variable light domain ($V_H$) comprising an amino acid sequence of SEQ ID NO:51 or an amino acid sequence with at least 95% sequence similarity to SEQ ID NO:51; (b) a first flexible linker; and (c) a variable heavy domain ($V_L$) comprising an amino acid sequence of SEQ ID NO:52 or an amino acid sequence with at least 95% sequence similarity to SEQ ID NO:52, and wherein the second scFv comprises: (d) a variable light domain ($V_L$) comprising an amino acid sequence of SEQ ID NO:53 or an amino acid with at least 95% sequence similarity to SEQ ID NO:53; (e) a second linker; and (f) a variable heavy domain ($V_H$) comprising an amino acid sequence of SEQ ID NO:54 or an amino acid with at least 95% sequence similarity to SEQ ID NO:54; and wherein the bispecific antibody comprises from 5' to 3': the $V_H$ of the first scFv, the $V_L$ of the first scFv, the $V_L$ of the second scFv, and the $V_H$ of the second scFv. In some aspects, the first single-chain variable fragment (scFv) that binds to CD3 and second scFv that binds to IL13Rα2 are linked via a third flexible linker.

In a further aspect, the disclosure provides transgenic neural stem cells (NSCs) that expresses the bispecific antibody described herein.

In yet another aspect, the disclosure provides a method of treating an IL13Rα2-expressing cancer in a subject, the method comprising: administering a therapeutically effective amount of the bispecific antibody described herein, the composition described herein, or the transgenic NSCs described herein to the subject to treat the cancer.

In a further aspect, the disclosure provides a method for inducing lysis of a target cell, particularly a tumor cell, comprising contacting a target cell with a bispecific antibody described herein in the presence of a T cell, particularly a cytotoxic T cell. In some embodiment, the method is in vivo.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
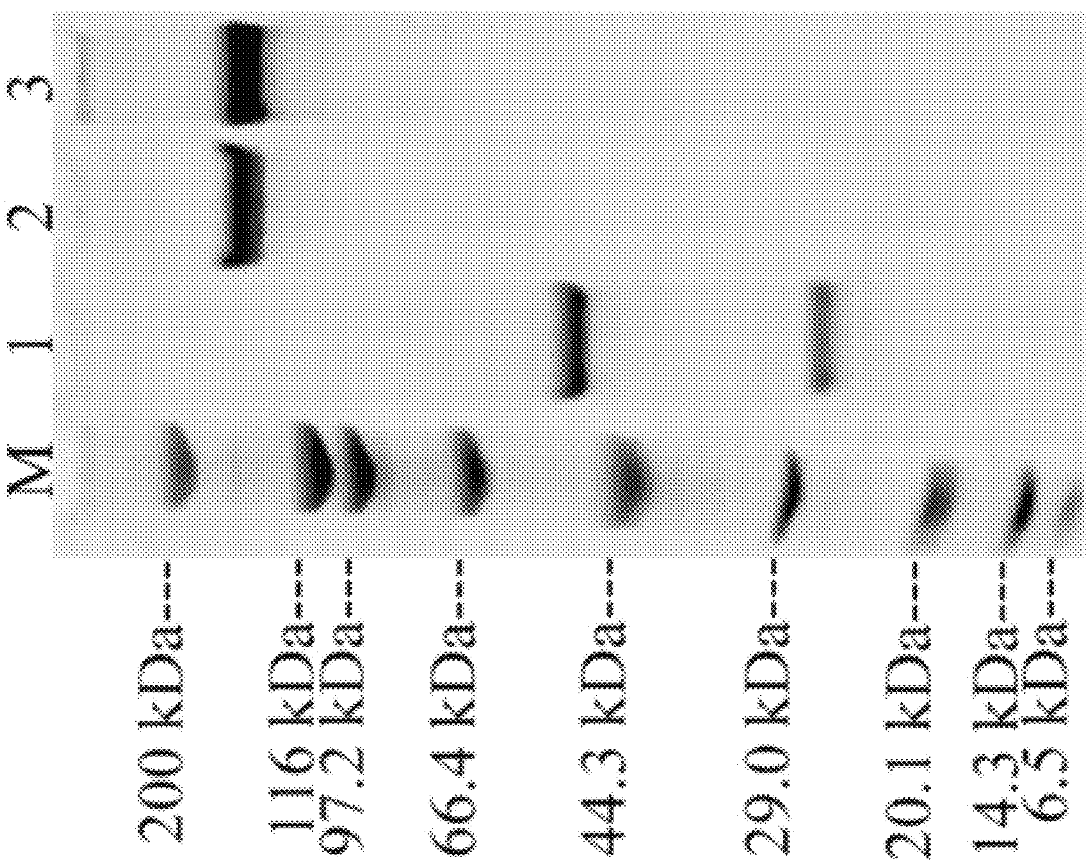
FIG. 1 shows the results of running chimeric antibody on SDS-PAGE under reducing and non-reducing conditions. Lane M: Protein marker. Lane 1: Reducing condition (Purity: 99%). Lane 2: Non-reducing condition (Purity: 99%). Lane 3: Human IgG.

Proteins that are expressed by tumor cells but not by normal cells are attractive molecular targets for the delivery of cytotoxic molecules to treat cancer. Antibodies are one promising means to target these tumor-specific proteins. Bispecific T cell engagers are also a further mean to target tumor cells and direct a cytotoxic immune response. In previous work, the inventor generated a mouse monoclonal antibody (mAb) against IL-13 receptor α2 (IL13Rα2), and demonstrated that the variable regions of the heavy chain (SEQ ID NO:25) and light chain (SEQ ID NO:26) of this antibody could be fused to functional moieties in a variety of configurations for therapeutic purposes (see U.S. Pat. No. 10,308,719, which is incorporated by reference in its entirety). IL13Rα2 is a monomeric high-affinity interleukin-13 (IL-13) receptor. Importantly, L13Rα2 is overexpressed by the majority of glioblastoma (GBM) tumors as well as several other tumor types, but is not expressed at significant levels on normal brain tissue.

In the present application, the inventor disclosed humanized antibody variants derived from the IL13Rα2-binding mouse monoclonal antibody. The inventor inserted the complementarity-determining regions (CDRs) of the mouse antibody into four different heavy chain variable region ($V_H$) human scaffolds and four different light chain variable region ($V_L$) human scaffolds, forming four humanized $V_H$ regions (amino acid sequences: SEQ ID NO:1-4; DNA sequences: SEQ ID NO:17-20) and four humanized $V_L$ regions (amino acid sequences: SEQ ID NO:5-8; DNA sequences: SEQ ID NO:21-24). The inventor expressed pairs of these humanized $V_H$ and $V_L$ regions to form 16 different humanized single-chain variable fragment (scFv) antibodies, each comprising one $V_H$ and one $V_L$ region (see Example 1). Surprisingly, several of the humanized scFv antibodies displayed improved binding affinity for IL13Rα2 as compared to the original murine scFv antibody. Further, the humanized antibodies were further altered in their amino acid sequence to provide additional benefits for use of the antibodies for human treatment, including longer-term stability and increased affinity for their receptor, increasing their desirability and potency as a therapeutic. For example, removal of certain post-translational modifications may stabilize the antibody product, as described more herein. The two main changes described herein is the altering of the amino acids (DG) that form an isomerization site in the antibodies and the removal of an oxidation site (e.g., tryptophan within the CDRs (i.e., W100F of the variable light chain). Isomerization can decrease binding affinities of the antibodies and reduce the stability of the polypeptides, thus the ability to decrease the isomerization of the humanized antibodies and bispecific antibodies described herein results in improved binding and stability. Tryptophan (Trp) has unique hydrophobic and structural properties, especially when positioned within the CDR. However, oxidation of Trp residues within the CDR can deleteriously impact antigen binding especially if it alters the CDR confirmation (see, e.g., Hageman et al. Impact of Tryptophan oxidation in complementarity-determining regions of two monoclonal antibodies on structure-function characterized by hydrogen-deuterium exchange mass spectrometry and surface plasmon resonance, Pharm Res (2019) 36:24). The removal of the oxidation site as described herein may allow for increased stability of the humanized antibody products produced while retaining the affinity to L13Ra2 (see Table 16). Humanized antibodies offer several advantages for clinical use: they are less immunogenic that their mouse counterparts, they show improved serum half-life, and they produce better therapeutic outcomes. Thus, with their improved ability to target IL3Rα2, the humanized antibodies of the present invention are promising therapeutic tools for the treatment of GBM and other cancers.

The potency of therapeutic antibodies can be diminished by the isomerization of specific aspartic acid residues. When isomerization occurs in a complementarity-determining region (CDR), it can decrease the binding affinities of these antibodies to their ligands. Further, isomerization can reduce the stability of these proteins, which becomes problematic during prolonged storage. When the present inventor analyzed the post-translational modifications of their humanized antibodies, they identified an aspartic acid residue (D55) and glycine reside (G56) within a CDR2 of the heavy chain that is susceptible to isomerization due to the presence of a glycine residue at its C-terminal end. Accordingly, the inventor generated point mutations at both aspartic acid residue (D55E; see, e.g., SEQ ID NO:27, SEQ ID NO:54) and the downstream glycine residue (G56A; see, e.g., SEQ ID NO:28, SEQ ID NO:54) and tested the binding affinity of the resultant antibodies (see Example 2). This analysis revealed that while the D55E mutation produced an antibody with decreased binding affinity, the G56A mutation did not significantly affect affinity. However, antibodies comprising the D55E mutation showed less reduction in binding after prolonged storage at warmer temperatures, suggesting that it may offer an improved in vivo half-life at physiological body temperature. Thus, removal of this isomerization site may be a critical step in adapting these antibodies for use in therapeutic applications, as demonstrated in the examples. The stability of these antibodies was tested demonstrating that they have higher melting temperatures and better stability for storage and use conditions than the chimeric antibodies.

The inventor inspected the sequences of the humanized antibodies for other sites that could affect binding activity, such as N-glycosylation sites, post-translational modifications, and unpaired cysteine residues (see Example 3). These sites, which are indicated with a numbered X in modified versions of the $V_H$ (SEQ ID NO:9-12, 54) and $V_L$ (SEQ ID NO:13-16, 53) sequences disclosed herein, which can be used to generate additional variants of the humanized antibodies with specific point mutations. These mutations may provide improved stability for the antibodies, especially for in vivo administration and use.

Figure 23:
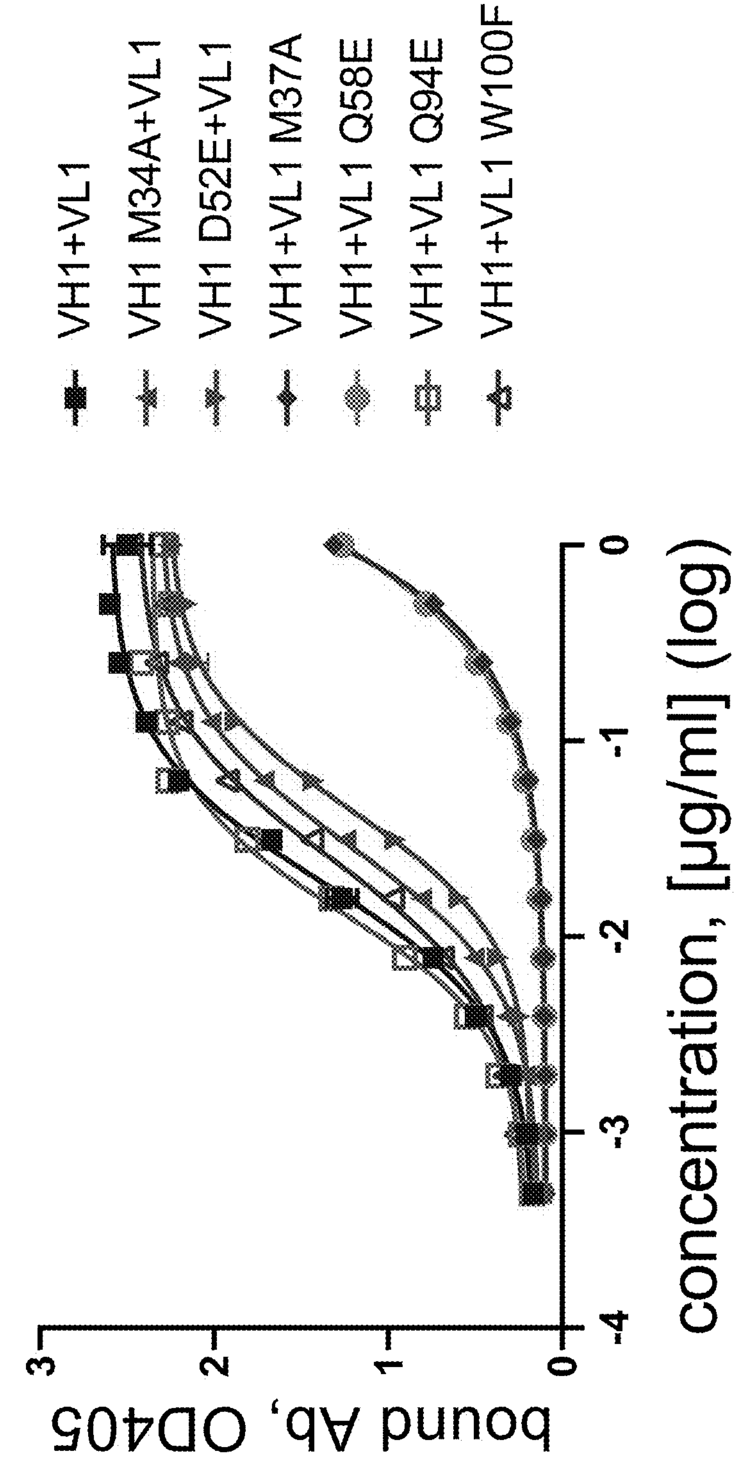
FIG. 23 shows a comparison of binding of humanized antibody (VH1-VL1) and variants of humanized antibody with mutations in either the VH1 chain (M34A, D52E) or VL1 chain (M37A, Q58E, Q94E, W100F) to human recombinant IL13Rα2 in plate ELISA. N=4. Data is presented as mean±SEM.

Antibodies:

The present invention provides humanized antibodies that bind IL13Rα2. The inventor has engineered a number of different variants of humanized antibodies or fragments thereof that have better infinities for the receptor (IL13Rα2), increased stability and reduced isomerization, which provide improved properties that are desirable for human therapeutics. The inventor specifically found that mutations to disrupt a potential isomerization hot spot (e.g., DG in position 55 and 56 of SEQ ID NO:54) and a mutation at W100 (e.g., W100F of SEQ ID NO:53) as a potential. These mutations provided additional benefits to the antibodies and bispecific antibodies (T cell engagers) of the present technology by increasing binding, stability and purity of the product. The inventor surprisingly found that other mutations that alter other post-modification sites drastically reduced the binding and production of the antibodies (e.g., M37A and Q58E, as demonstrated in FIG. 23). Thus, the inventor has engineered mutant antibodies and fragments thereof that provide enhanced properties for use as therapeutics.

In one embodiment, the disclosure provides engineered humanized antibodies that binds to IL13Rα2 comprising: a variable light domain ($V_L$) comprising an amino acid sequence of SEQ ID NO:53 or an amino acid with at least 95% sequence similarity to SEQ ID NO:53; and a variable heavy domain ($V_H$) comprising an amino acid sequence of SEQ ID NO:54 or an amino acid with at least 95% sequence similarity to SEQ ID NO:54. In some embodiments, (a) $X_1$ in $V_L$ is F; (b) $X_2$ in $V_H$ is E, (c) $X_3$ in $V_H$ is A; or (d) combinations of (a), (b) and (c). In a preferred embodiment, $X_1$ in $V_L$ is F; and $X_3$ in $V_H$ is A. Suitably, in a preferred embodiment, the humanized antibody is a single chain antibody and further comprising a flexible linker between the $V_H$ and $V_L$ domain. Suitable flexible linkers can be determined by one skilled in the art and include, for example, an amino acid sequence from 4-25 amino acids in length, and preferably comprising, for example, glycine and serine.

In another aspect, the antibodies comprise (a) a variable heavy domain comprising SEQ ID NO:1, SEQ ID NO:2, SEQ ID NO:3, SEQ ID NO:4, SEQ ID NO:9, SEQ ID NO:10, SEQ ID NO:11, SEQ ID NO:12, or an amino acid sequence having at least 95% sequence similarity to SEQ ID NO:1-4 or SEQ ID NO:9-12; and (b) a variable light domain comprising SEQ ID NO:5, SEQ ID NO:6, SEQ ID NO:7, SEQ ID NO:8, SEQ ID NO:13, SEQ ID NO:14, SEQ ID NO:15, SEQ ID NO:16, or an amino acid sequence having at least 95% sequence similarity to SEQ ID NO:5-8 or SEQ ID NO:13-16.

The term "antibody" is used herein to refer to immunoglobulin molecules or other molecules that comprise an antigen-binding domain from an immunoglobulin molecule. Suitable antibody molecules include, without limitation, whole antibodies (e.g., IgG, IgA, IgE, IgM, or IgD), monoclonal antibodies, humanized antibodies, and antibody fragments, including single chain variable fragments (ScFv), single domain antibodies, antigen-binding fragments (e.g., complementarity determining region (CDR) domains), and genetically engineered antibodies. Thus, the humanized antibodies of the present invention may be configured as any form of antibody, antibody fragment, or antibody-derived fragment, as long as they retain the ability to bind IL13Rα2. Antibody binding may be assessed using any appropriate assay including, for example, surface plasmon resonance (SPR), radioimmunoassay, flow cytometry, enzyme-linked immunosorbent assays (ELISA), fluorescence immunoassay (FIA), thermal shift assay, LC-MS detection, and kinetic exclusion assays (KinExA).

As stated above, the term "antibody" includes "antibody fragments" or "antibody-derived fragments" that comprise an antigen-binding domain. As used herein, the term "antibody fragment" is intended to include any fragment that displays antigen (i.e., IL13Rα2) binding function, for example, Fab, Fab', F(ab')2, scFv, Fv, dsFv, ds-scFv, Fd, dAbs, TandAbs dimers, mini bodies, monobodies, diabodies, and multimers thereof and bispecific antibody fragments. As used herein, the term "fragment" refers to fragments of biological relevance (i.e., functional fragments). For example, the fragments may contribute to or enable antigen binding, form part of or all of an antigen binding site, or contribute to the prevention of the antigen interacting with its natural ligand.

The antibodies disclosed herein comprise at least a heavy chain variable region ($V_H$), which generally comprises the antigen-binding site, and a light chain variable region ($V_L$). However, the antibodies may further comprise additional antibody regions. For example, the antibodies can be made such that they also comprise all or a portion of a heavy chain constant region, such as an IgG1, IgG2, IgG3, IgG4, IgA1, IgA2, IgE, IgM or IgD constant region. Furthermore, the antibody or antibody fragment can comprise all or a portion of a kappa light chain constant region or a lambda light chain constant region. The $V_H$ and $V_L$ sequences disclosed herein can be genetically engineered into antibodies and antibody fragments using conventional techniques, including recombinant or chemical synthesis techniques, which are well known and described in the art.

Importantly, the antibodies of the present invention are humanized antibodies. The term "humanized antibody" refers to antibodies in which the human antibody framework has been modified to comprise fragments of antibodies taken from a different species (i.e., mouse) that provide antigen specificity. This term includes chimeric antibodies containing minimal sequence derived from non-human immunoglobulin. For example, the hypervariable region residues of a human antibody may be replaced by hypervariable region residues from a non-human species having the desired specificity, affinity, and capacity. For example, the present inventor created humanized antibodies by inserting the complementarity-determining regions (CDRs) of a previously disclosed mouse antibody into several different heavy chain variable region ($V_H$) and light chain variable region ($V_L$) human scaffolds. In some instances, framework region (FR) residues of the human immunoglobulin are replaced by corresponding non-human residues. In some instances, humanized antibodies may comprise residues that are not found in the recipient antibody or in the donor antibody and are included to refine antibody performance. In general, the humanized antibody will comprise substantially all of at least one, and typically two or three variable domains, in which all or substantially all of the hypervariable loops correspond to those of a non-human immunoglobulin and all or substantially all of the FR regions are those of a human immunoglobulin sequence. In some embodiments, the humanized antibody will also optionally comprise at least a portion of an immunoglobulin constant region (Fc), typically that of a human immunoglobulin. Appropriate sequences for such constant regions are well known and documented in the art. For further details, see Jones et al., Nature 321:522-525 (1986); Reichmann et al., Nature 332: 323-329 (1988); and Presta, Curr. Op. Struct. Biol. 2:593-596 (1992).

In the Examples, the humanized antibodies were expressed as single-chain variable fragment (scFv) antibodies. As used herein, the term "single-chain variable fragment" or "scFv" refers to a fusion protein of the variable regions of the heavy ($V_H$) and light chains ($V_L$) of immunoglobulins, connected with a short linker peptide of about ten to about 25 amino acids. The linker may be rich in glycine for flexibility, as well as serine or threonine for solubility. The linker can either connect the N-terminus of the $V_H$ with the C-terminus of the $V_L$, or vice versa. ScFvs may be produced in a cell culture of microbes such as *Escherichia coli* or *Saccharomyces cerevisiae*. ScFvs can also be produced in tissue culture, for example, in a mammalian or human cell line. ScFvs have many uses, e.g., therapeutic, flow cytometry, immunohistochemistry, and as antigen-binding domains of artificial T cell receptors. Thus, in some embodiments, the humanized antibody is a single chain antibody (ScFv), and in some embodiments, the heavy variable region ($V_H$) and the light variable region ($V_L$) are linked by a flexible linker. In some embodiments, the sequences of the variable regions (i.e., $V_H$ and $V_L$) may further comprise a signal sequence, e.g., the signal sequence from mouse Ig heavy chain V region 102 (e.g., amino acid sequence: SEQ ID NO:29; nucleotide sequence: SEQ ID NO:46). Other suitable signal sequences are contemplated for use and known in the art, and can be located 5' to the variable heavy domain. Signal sequences allow for the secretion of the humanized antibody, and are cleaved during maturation of the antibody when secreted from the cells into the extracellular space.

In certain embodiments, the humanized antibodies comprise the scFvs tested in Example 1 or described in Examples 4-6. In these embodiments, the antibodies comprise: (i) SEQ ID NO:1 and SEQ ID NO:5; (ii) SEQ ID NO:1 and SEQ ID NO:6; (iii) SEQ ID NO:1 and SEQ ID NO:7; (iv) SEQ ID NO:1 and SEQ ID NO:8; (v) SEQ ID NO:2 and SEQ ID NO:5; (vi) SEQ ID NO:2 and SEQ ID NO:6; (vii) SEQ ID NO:2 and SEQ ID NO:7; (viii) SEQ ID NO:2 and SEQ ID NO:8; (ixv) SEQ ID NO:3 and SEQ ID NO:5; (x) SEQ ID NO:3 and SEQ ID NO:6; (xi) SEQ ID NO:3 and SEQ ID NO:7; (xii) SEQ ID NO:3 and SEQ ID NO:8; (xiii) SEQ ID NO:4 and SEQ ID NO:5; (xiv) SEQ ID NO:4 and SEQ ID NO:6; (xv) SEQ ID NO:4 and SEQ ID NO:7; and (xvi) SEQ ID NO:4 and SEQ ID NO:8. In some embodiments, the scFvs are antibodies that comprise amino acid sequences with at least 95% sequence identity to the SEQ IDs listed, and the antibodies retain their ability to bind to IL13Rα2.

The humanized antibodies of the present invention may be from any appropriate source. The antibodies can be produced in vitro or in vivo, and can be wholly or partially synthetically produced. For example, the antibodies may be from a recombinant source and/or produced in transgenic cells, animals or transgenic plants.

As discussed above, the binding affinity of an antibody can be compromised when sites within functional regions (e.g., CDRs) undergo chemical changes such as isomerization or post-translational modification. In Example 3, the inventor identified specific residues that are susceptible to such chemical changes. These residues, which are indicated with a numbered X in generic versions of the $V_H$ (SEQ ID NO:9-12) and $V_L$ (SEQ ID NO:13-16) sequences disclosed herein, include methionine residues that are susceptible to oxidation (M34 in the $V_H$ sequences, M37 in the $V_L$ sequences), an aspartic acid (D52 in $V_H$) and downstream proline residue (P53 in $V_H$) that form a potential hydrolysis site, an aspartic acid (D55 in $V_H$) and downstream glycine residue (G56 in $V_H$) that form a potential isomerization site, glutamine residues that are susceptible to deamination (Q58 and Q94 in $V_L$), and a tryptophan residue (W100 in $V_L$) that is susceptible to oxidation.

Thus, in some embodiments, the humanized antibodies comprise point mutations that have been designed to prevent chemical changes at these susceptible residues. Specifically, in some embodiments, the humanized antibodies comprise: (i) a $V_H$ selected from the group consisting of SEQ ID NO:9, SEQ ID NO:10, SEQ ID NO:11, or SEQ ID NO:12, wherein the $V_H$ has one or more mutations selected from M34L, M34A, M34I, M34V, D52E, P53A, D55E, and G56A; or (ii) a $V_L$ comprising the amino acid sequence selected from the group consisting of SEQ ID NO:13, SEQ ID NO:14, SEQ ID NO:15, and SEQ ID NO:16, wherein the $V_L$ comprising one or more mutations selected from M37L, M37I, M37V, Q58R, Q58A, Q94E, Q94R, Q94A, W100F, or W100Y. In some embodiments, the humanized antibody comprises (i) a $V_H$ selected from the group consisting of SEQ ID NO:9, SEQ ID NO:10, SEQ ID NO:11, or SEQ ID NO:12, wherein the $V_H$ has one or more mutations selected from M34L, M34A, M34I, M34V, D52E, P53A, D55E, and G56A; or (ii) a $V_L$ comprising the amino acid sequence selected from the group consisting of SEQ ID NO:13, SEQ ID NO:14, SEQ ID NO:15, and SEQ ID NO:16, wherein the $V_L$ comprising two or more mutations selected from M37L, M37I, M37V, Q58R, Q58A, Q94E, Q94R, Q94A, W100F, or W100Y. In some embodiments, the humanized antibody comprises (i) a $V_H$ selected from the group consisting of SEQ ID NO:9, SEQ ID NO:10, SEQ ID NO:11, or SEQ ID NO:12, wherein the $V_H$ has two or more mutations selected from M34L, M34A, M34I, M34V, D52E, P53A, D55E, and G56A; or (ii) a $V_L$ comprising the amino acid sequence selected from the group consisting of SEQ ID NO:13, SEQ ID NO:14, SEQ ID NO:15, and SEQ ID NO:16, wherein the $V_L$ comprising two or more mutations selected from M37L, M37I, M37V, Q58R, Q58A, Q94E, Q94R, Q94A, W100F, or W100Y. In some embodiments, the humanized antibody comprises (i) a $V_H$ selected from the group consisting of SEQ ID NO:9, SEQ ID NO:10, SEQ ID NO:11, or SEQ ID NO:12, wherein the $V_H$ has two or more mutations selected from M34L, M34A, M34I, M34V, D52E, P53A, D55E, and G56A; or (ii) a $V_L$ comprising the amino acid sequence selected from the group consisting of SEQ ID NO:13, SEQ ID NO:14, SEQ ID NO:15, and SEQ ID NO:16, wherein the $V_L$ comprising one or more mutations selected from M37L, M37I, M37V, Q58R, Q58A, Q94E, Q94R, Q94A, W100F, or W100Y. The present invention contemplates where each of the $V_H$ and $V_L$ may contain one or more, two or more, three or more, four or more, five or more, six or more of the mutations described and any combinations thereof (e.g., one mutation in $V_H$ and one mutation in $V_L$, two mutations in $V_H$ and only one mutation in $V_L$, etc.) and that the combinations are not limited to the exemplary embodiments described herein.

In certain embodiments, the humanized antibodies comprise point mutations that disrupt the potential isomerization site formed by an aspartic acid (D55) and downstream glycine residue (G56) in the $V_H$ sequences disclosed herein, which were tested in Example 2. In these embodiments, the humanized antibodies cannot isomerize and comprises (i) a $V_H$ selected from SEQ ID NO:9, SEQ ID NO:10, SEQ ID NO:11, or SEQ ID NO:12 wherein the $V_H$ comprises G56A, and a $V_L$ selected from SEQ ID NO:5, SEQ ID NO:6, SEQ ID NO:7, SEQ ID NO:8, SEQ ID NO:13, SEQ ID NO:14, SEQ ID NO:15, or SEQ ID NO:16, (ii) a $V_H$ selected from SEQ ID NO:9, SEQ ID NO:10, SEQ ID NO:11, or SEQ ID NO:12 wherein the $V_H$ comprises D55E, and a $V_L$ selected from SEQ ID NO:5, SEQ ID NO:6, SEQ ID NO:7, SEQ ID NO:8, SEQ ID NO:13, SEQ ID NO:14, SEQ ID NO:15, or SEQ ID NO:16, or (iii) a $V_H$ selected from SEQ ID NO:9, SEQ ID NO:10, SEQ ID NO:11, or SEQ ID NO:12 wherein the $V_H$ comprises D55E and G56A, and a $V_L$ selected from SEQ ID NO:5, SEQ ID NO:6, SEQ ID NO:7, SEQ ID NO:8, SEQ ID NO:13, SEQ ID NO:14, SEQ ID NO:15, or SEQ ID NO:16.

The inventor discovered that many of the humanized ScFv antibodies they tested have a greater affinity for IL13Rα2 than the original mouse ScFv antibody. Affinity, the strength with which a molecule binds to its ligand, refers to the strength of the sum total of non-covalent interactions between a single binding site of a molecule and its binding partner and is typically measured and reported as an equilibrium dissociation constant ($K_D$). $K_D$ is the ratio of the antibody dissociation rate ($k_d$, i.e., how quickly it dissociates from its antigen) to the antibody association rate ($k_a$, i.e., how quickly it binds to its antigen). Thus, $K_D$ and affinity are inversely related, such that a lower $K_D$ value indicates a higher affinity and a higher $K_D$ value indicates a lower affinity. In the Examples, the $K_D$ was determined for each antibody using a surface plasmon resonance (SPR) biosensor to measure the dissociation ($k_d$) and association ($k_a$) rate constants. Accordingly, in some embodiments, the humanized antibody comprise an antibody with a $K_D$ that is less than that that of the original mouse antibody (i.e., less than $5\times10^{-9}$, preferably less than $1\times10^{-10}$). In some embodiments, the humanized antibody or bispecific antibody has a binding constant ($K_D$) of $5\times10^{-9}$ M or less for IL13Rα2. In some embodiments, the humanized antibody has a binding constant ($K_D$) of $2\times10^{-10}$ M or less for IL13Rα2.

With their affinity for IL13Rα2, the humanized antibodies of the present invention are useful for targeting IL13Rα2-expressing cancer cells. This ability can be harnessed to deliver other molecules to cancer cells. Thus, in some embodiments, the humanized antibodies further comprise an agent. The term "agent," as used herein, includes any useful moiety that allows for the purification, identification, detection, diagnosing, imaging, or therapeutic use of the antibodies of the present invention. The agent is selected according to the intended application (e.g., treatment of a particular cancer) and may be covalently or non-covalently connected to the antibody. In one embodiment, the agent conjugated to the antibody forming an antibody-conjugate. Methods of conjugating antibodies to compounds are described below. Additionally, the agent may be connected to the antibody by genetically fusing the agent via creation of a fusion protein as described below.

In some embodiments, the agent is a therapeutic agent. Exemplary therapeutic agents include, without limitation, pharmaceuticals, biologics, toxins, fragments of toxins, alkylating agents, enzymes, antibiotics, antimetabolites, antiproliferative agents, chemotherapeutic agents, hormones, neurotransmitters, DNA, RNA, siRNA, oligonucleotides, antisense RNA, aptamers, lectins, compounds that alter cell membrane permeability, photochemical compounds, small molecules, liposomes, micelles, gene therapy vectors, viral vectors, immunological therapeutic constructs, and other drugs. Drugs that treat cancer are particularly suitable for use in the present invention.

In other embodiments, the agent is a detection agent. Suitable detection agents include, without limitation, epitope tags, detectable markers, radioactive markers, and nanoparticles. Suitable epitope tags are known in the art and include, but are not limited to, 6-Histidine (His), hemagglutinin (HA), cMyc, GST, Flag tag, V5 tag, and NE-tag, among others. Epitope tags are commonly used as a purification tags (i.e., an agent that allows isolation of the antibody from other non-specific proteins). Suitable detectable markers include luminescent markers, fluorescent markers (e.g., fluorescein, fluorescein isothiocyanate, rhodamine, dichlorot[pi]azinylamine fluorescein, green fluorescent protein (GFP), red fluorescent protein (RFP), blue fluorescent dyes excited at wavelengths in the ultraviolet (UV) part of the spectrum (e.g., AMCA (7-amino-4-methylcoumarin-3-acetic acid); Alexa Fluor 350), green fluorescent dyes excited by blue light (e.g., FITC, Cy2, Alexa Fluor 488), red fluorescent dyes excited by green light (e.g., rhodamines, Texas Red, Cy3, Alexa Fluor dyes 546, 564 and 594), or dyes excited with infrared light (e.g., Cy5), dansyl chloride, and phycoerythrin), or enzymatic markers (e.g., horseradish peroxidase, alkaline phosphatase, beta-galactosidase, glucose-6-phosphatase, and acetylcholinesterase). Suitable radioactive markers include, but are not limited to, $^{125}I$, $^{131}I$, $^{35}S$ or $^{3}H$. Suitable nanoparticles, including metal nanoparticles and other metal chelates, are known in the art and include, but are not limited to, gold nanoparticles (ACSNano, Vol. 5, No. 6, 4319-4328, 2011), quantum dots (Nanomedicine, 8 (2012) 516-525), magnetic nanoparticles ($Fe_3O_4$), silver nanoparticles, nanoshells, and nanocages.

Methods of conjugating, linking and coupling antibodies to compounds are well known in the art, see Nat Biotechnol. (2005) 23(9):1137-46; Cancer Immunol Immunother. (2003) 52(5):328-37; and Adv Drug Deliv Rev. (2003) 55(2):199-215. For example, one may wish to link the antibodies of the present invention to an agent via primary amines (see Pharmaceutical Research (2007) 24(9): p. 1759-1771). For example, lysine residues of either antibody or agent may be functionalized using Traut's reagent (2-iminothiolane.HCL) yielding a thiol. The thiol group, now attached to the lysine residue, is reacted with a maleimide-functionalized drug or vector resulting in a stable thio-ether bond. One may optionally use a chemical spacer such as polyethylene glycol to reduce steric hindrance. Alternatively, one may wish to link the antibody to the agent non-covalently. For example, one could use biotin/streptavidin interaction (see Pharmaceutical Research (2007) 24(9): p. 1759-1771, incorporated by reference in its entirety). Lysine residues of either the antibody or agent may be biotinylated using one of a number of commercial methods (e.g., N-hydroxysuccinimide biotin analogs). Then, either the antibody or the agent (whichever one was not modified in the previous step) would be conjugated to streptavidin or one of its variants (e.g., neutravidin). The monobiotinylated reagent and the streptavidin-conjugated counterpart would be combined and the near-covalent binding affinity would keep the reagents together. Conjugation may optionally be accomplished with a cleavable or non-cleavable linker. Many chemical cross-linking methods are also known in the art. Cross-linking reagents may be homobifunctional (i.e., having two functional groups that undergo the same reaction) or heterobifunctional (i.e., having two different functional groups). Numerous cross-linking reagents are commercially available, and detailed instructions for their use are readily available from the commercial suppliers. For a general reference on polypeptide cross-linking and conjugate preparation, see Wong, Chemistry of protein conjugation and cross-linking, CRC Press (1991).

In some embodiments, the agent is a polypeptide that is translated concurrently with the antibody polypeptide sequence as a fusion protein. In such embodiments, the agent is "genetically fused" to the antibody. For example, one may wish to express the antibody as a fusion protein with a therapeutic peptide. Standard molecular biology techniques (e.g., restriction enzyme based subcloning or homology based subcloning) can be used to insert the DNA sequence encoding the agent in frame with the targeting vector. Optionally, a protein linker may be added to avoid steric hindrance. The fusion protein is then produced as one peptide in a cell (e.g., yeast, bacteria, insect, or mammalian cell) and purified before use. Note that the agent does not need to be a whole protein.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al, Kuby Immunology, 6$^{th}$ ed., W. H. Freeman and Co., page 91 (2007). A single VH or VL domain may be sufficient to confer antigen-binding specificity. The term "hypervariable region" or "HVR" are also referred to as "complementarity determining regions" (CDRs), and these terms are used herein interchangeably in reference to portions of the variable region that form the antigen binding regions. These regions of an antibody variable domain are hypervariable in sequence and/or form structurally defined loops ("hypervariable loops"). Generally, native four-chain antibodies comprise six CDRs; three in the VH (H1, H2, H3), and three in the VL (L1, L2, L3). With the exception of CDR1 in VH, CDRs generally comprise the amino acid residues that form the hypervariable loops. This particular region has been described by Kabat et al, U.S. Dept. of Health and Human Services, Sequences of Proteins of Immunological Interest (1983) and by Chothia et al, J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The exact residue numbers that encompass a particular CDR will vary depending on the sequence and size of the CDR. Those skilled in the art can routinely determine which residues comprise a particular CDR given the variable region amino acid sequence of the antibody.

Bispecific Antibodies

In another embodiment of the present invention, the inventor has engineered humanized bispecific antibodies. The term "bispecific" means that the molecule is able to specifically bind to at least two distinct moieties (e.g., antigen binding sites). Typically, a bispecific molecule comprises two different binding sites, each of which is specific for a different moiety (e.g., antigen). In certain embodiments, the bispecific molecule is capable of simultaneously binding two moieties, particularly two moieties expressed on two distinct cells (e.g., a tumor cell and a T cell). The bispecific antibodies described herein are capable of binding a target antigen and a T cell antigen. The term "bispecific antibody", "bispecific T cell engager" and "BTE" are used interchangeable herein and refer to the antibody molecules that are capable of binding two distinct antigens at the same time. Particularly, the bispecific antibodies are capable of binding to the surface of tumor cells and T cells simultaneously, allowing for activation of the T cells, and the targeting killing of tumor cells bound to the bispecific antibody.

The bispecific antibodies described herein comprise or consist of two single-chain variable fragments (scFvs) connected by a flexible linker. One of the scFvs is directed to a target associated antigen, in this particular invention, to IL13Rα2 which is found on cancer cells, particularly glioblastoma. The other scFv is capable of binding to an activating T cell antigen, in this particular embodiment, a CD3 ε that is expressed on T cells. The bispecific antibody by binding CD3 engage tumor infiltrating lymphocytes (TILs) and cancer cells in an MHC independent manner and are, therefore, unaffected by MHC downregulation that occurs in some cancers, for example, in glioblastoma (GBM) cells. The specificity of bispecific antibody's tumor antigen-directed scFv is imperative to harness the full therapeutic potential of the recombinant molecule. BTE anticancer activity requires BTE binding with malignant cancer and immune cells simultaneously; as has been demonstrated in the art, single-arm binding to a tumor antigen or CD3ε is therapeutically ineffective.

An "activating T cell antigen" as used herein refers to an antigenic determinant expressed on the surface of a T lymphocyte, particularly a cytotoxic T lymphocyte, which is capable of inducing T cell activation upon interaction with an antigen binding molecule. Specifically, interaction of an antigen binding molecule with an activating T cell antigen may induce T cell activation by triggering the signaling cascade of the T cell receptor complex. In a particular embodiment the activating T cell antigen is CD3.

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. The T cell activating bispecific antigen binding molecules of the invention are capable of inducing T cell activation. Suitable assays to measure T cell activation are known in the art described herein.

Expression of IL13Rα2 in GBM 12, GBM 6, and GBM 39 used for toxicity and T cells activation assays are known in the art and have been previously described by the inventor (e.g., Balyasnikova et. al. Characterization and immunotherapeutic implications for a novel antibody targeting interleukin (IL)-13 receptor α2. J Biol Chem. 2012 Aug. 31; 287(36):30215-27. doi: 10.1074/jbc.M112.370015. Epub 2012 Jul. 9. PMID: 22778273; PMCID: PMC3436275, and Pituch et al. Neural stem cells secreting bispecific T cell engager to induce selective antiglioma activity. Proc Natl Acad Sci USA. 2021 Mar. 2; 118(9):e2015800118. doi: 10.1073/pnas.2015800118. PMID: 33627401; PMCID: PMC7936285.)

The "target cell antigen" as used herein refers to an antigen presented on the surface of a target cell, for example a cancer cell or a cell of the tumor stroma. Specifically, in the present invention, the target cell antigen is IL13Rα2, which is found on glioblastoma cells.

In one embodiment, the present disclosure provides an engineered bispecific T cell engager comprising a first single-chain variable fragment (scFv) that binds to CD3 and a second scFv that binds to IL13Rα2 as described herein. In one embodiment, the first scFv comprises: (a) a variable heavy domain (VH) comprising an amino acid sequence of SEQ ID NO:51 or an amino acid sequence with at least 95% sequence similarity to SEQ ID NO:51; (b) a first flexible linker; and (c) a variable light domain (VL) comprising an amino acid sequence of SEQ ID NO:52 or an amino acid sequence with at least 95% sequence similarity to SEQ ID NO:52, and wherein the second scFv comprises: (d) a variable light domain (VL) comprising an amino acid sequence of SEQ ID NO:53 or an amino acid with at least 95% sequence similarity to SEQ ID NO:53; (e) a second linker; and (f) a variable heavy domain (VH) comprising an amino acid sequence of SEQ ID NO:54 or an amino acid with at least 95% sequence similarity to SEQ ID NO:54; and wherein the bispecific antibody comprises from 5' to 3': the VH of the first scFv, the VL of the first scFv, the VL of the second scFv, and the VH of the second scFv. Specifically, the orientation of the VH and VL domains and linker between two scFvs is important for the design and proper functioning of the bispecific antibody. Thus, the suitable designed bispecific antibodies have the following orientation: α-CD3 VH-linker-αCD3 VL-linker-humanized VH scFvIL13Rα2-linker humanized scFvIL13Rα2 VL. Suitable polypeptides comprising the bispecific antibodies are found in SEQ ID NO:48, SEQ ID NO:49; SEQ ID NO:56-59. In some embodiments, the engineered bispecific antibodies comprise the first single-chain variable fragment (scFv) that binds to CD3 and second scFv that binds to IL13Rα2 are linked via a third flexible linker. Suitable linkers are known in the art and include those described above for the humanized antibodies, including, peptide sequences of 5-25 amino acids, preferably comprising glycines and serines. Suitable first and second linker include an amino acid sequence of about 10-20 amino acids, the amino acids selected from glycine and serine. In one suitable examples, the first and second linker are $(Gly_4S)_3$ (SEQ ID NO:55). In some aspects, the third linker is a 20-30 amino acid glycine-serine linker, for example, SEQ ID NO:56.

As used herein, the terms "first" and "second" with respect to scFv molecules, linkers, etc. are used for convenience of distinguishing when there is more than one of each type of moiety.

The bispecific antibodies described herein are engineered to be humanized. As discussed above, the humanized antibody against IL13Rα2 may include one or more mutations (e.g., G56A, W100F, or combinations thereof) that improve the stability, binding or both for the bispecific antibodies. In one embodiment, the scFv that binds to IL13Rα2 has a G52A mutation in the $V_H$ domain (e.g., $X_3$ is A in SEQ ID NO:48 or 54). In another embodiment, the bispecific antibodies comprises the D55E mutation in the $V_H$ domain (e.g., $X_2$ is E in SEQ ID NO:48 or 54). In a further embodiment, the bispecific antibody may be a mutation in the VL domain, e.g., W100F (e.g., $X_1$ in SEQ ID NO:48 or 53).

In some embodiments, the bispecific antibody further comprises a tag. Suitable tags are known in the art and described above, including epitope tags and purifications tags such as, for example, 6-Histidine (His), hemagglutinin (HA), cMyc, GST, Flag tag, etc.

Suitable examples of engineered bispecific antibodies of the present inventions are provided herein and include the polypeptide comprising or consisting of SEQ ID NO:48, SEQ ID NO:49, SEQ ID NO:57, SEQ ID NO:58, SEQ ID NO:59, SEQ ID NO:60, etc. or amino acid sequences having at least 95% sequence identity, at least 98% sequence identity, at least 99% sequence identity, 100% sequence identity to SEQ ID NO:48, 49, 57-60.

In some embodiments, a nucleic acid sequence encoding the bispecific antibody described herein, including vectors, is contemplated. In a further embodiment, a transgenic neural stem cell (NSC) that expresses the bispecific T cell engager described herein is also provided. Neural stem cells (NSCs) have inherent advantages as a cellular carrier of antineoplastic agents to the site of GBM since they are native to the brain. NSCs have demonstrated tropism to brain tumors in several preclinical models. These cells can withstand a harsh oxygen-deprived environment of GBM. NSCs can be used as producers of bispecific targeting the tumor-associated antigen IL13Rα2 and their antitumor activity using in vitro and in vivo models of GBM. In vitro, bispecific antibodies show significant antitumor activity when used in co-cultures that include T cells harvested from patients' blood and tumor tissue. In vivo, NSCs modified for bispecific antibody synthesis migrate to a tumor in animal subjects' brains while functioning as intra- and peritumoral bispecific antibody producers.

The terms "stability" and "stable" in the context of antibodies and bispecific antibodies describe the resistance of the antibodies or their fragments with respect to aggregation, degradation or fragmentation under the given conditions relating to their production, preparation, storage, use or transport. "Stable" formulations according to the present invention retain their biological activity under the given production, preparation, transport, use and storage conditions.

As described herein, the humanized antibodies and the engineered humanized bispecific antibodies are specific to two different moieties and display a higher binding affinity that the parent mouse antibody or derived chimeric antibodies, and shown in the examples. By "specific binding" we mean that the binding is selective for the antigen and can be discriminated from unwanted or non-specific interactions. The ability of an antigen binding moiety to bind to a specific antigenic determinant can be measured either through an enzyme-linked immunosorbent assay (ELISA) or other techniques familiar to one of skill in the art, e.g. surface plasmon resonance (SPR) technique (analyzed on a BIAcore instrument) (Liljeblad et al, Glyco J 17, 323-329 (2000)), and traditional binding assays (Heeley, Endocr Res 28, 217-229 (2002)).

In one embodiment, the extent of binding of an antigen binding moiety to an unrelated protein is less than about 10% of the binding of the antigen binding moiety to the antigen as measured, e.g., by SPR. In certain embodiments, an antigen binding moiety that binds to the antigen, or an antigen binding molecule comprising that antigen binding moiety, has a dissociation constant ($K_D$) of <1 μM, <100 nM, <10 nM, <1 nM, <0.1 nM, <0.01 nM, or <0.001 nM (e.g. $10^{-8}$ M or less, e.g. from $10^{-8}$ M to $10^{-13}$ M, e.g., from $10^{-9}$ M to $10^{-13}$ M).

Additional Compositions:

The present invention provides compositions comprising the humanized antibodies and humanized bispecific antibodies disclosed herein and a pharmaceutically acceptable carrier. The pharmaceutically acceptable carrier should be selected based upon the desired route of administration. For example, the humanized antibodies may be provided in combination with liposomes, nanoparticles or other analogous carriers loaded with a pharmaceutically active compound. Methods of preparing such compositions are known in the art (see, for example, Cancer Research (2000) 60, 6942-6949 and Analytical Chemistry News & Features (1998) pp. 322A-327A).

"Pharmaceutically acceptable" carriers are known in the art and include, but are not limited to, for example, suitable diluents, preservatives, solubilizers, emulsifiers, liposomes, nanoparticles, and adjuvants. Pharmaceutically acceptable carriers may be aqueous or nonaqueous solutions, suspensions, and emulsions. Examples of nonaqueous solvents are propylene glycol, polyethylene glycol, vegetable oils such as olive oil, and injectable organic esters such as ethyl oleate. Aqueous carriers include isotonic solutions, alcoholic/aqueous solutions, emulsions or suspensions, including saline and buffered media.

The compositions of the present invention may further include liquids or lyophilized or otherwise dried formulations and may include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, milamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

In some embodiments, the compositions are provided in lyophilized form and rehydrated with sterile water or saline solution before administration. Alternatively, the compositions may be provided in a sterile solution of known concentration. Further, the compositions may be added to an infusion bag containing 0.9% sodium chloride, USP and in some cases, administered in a dosage of from 0.5 to 15 mg/kg of body weight.

The compositions may also be prepared in unit dosaged forms for administration to a subject. The amount and timing of administration are at the discretion of the treating clinician to achieve the desired outcome. The humanized antibodies can be formulated for systemic or local (e.g., intravenous, intrathecal, intra-cranial) administration. In one example, the antibody is formulated for parenteral administration, such as intravenous administration.

In another aspect, the present invention provides nucleic acid sequences encoding the humanized antibodies disclosed herein. In some embodiments, the nucleic acid sequences comprise conservative or inconsequential substitutions or deletions.

In another aspect, the present invention provides vectors comprising the nucleic acid sequences that encode the humanized antibodies or engineered humanized bispecific antibodies disclosed herein. The vectors may be an expression vector comprising an expression cassette encoding the humanized antibodies or engineered humanized bispecific antibodies, or encoding the agent in addition to the humanized antibodies or bispecific antibodies. For example, a nucleic acid sequence encoding an antibody may be under the control of a heterologous promoter, allowing for the regulation of the transcription of said nucleic acid sequence in a cell. Said nucleic acid sequence can also be linked to appropriate control sequences to allow for regulation of its translation in a cell. Suitable vectors further include, for example, viral vectors, that allow for the transduction and expression of the engineered humanized antibodies and humanized bispecific antibodies described herein.

Methods:

In another aspect, the present invention provides methods of treating an IL13Rα2-expressing cancer in a subject. The methods comprise administering a therapeutically effective amount of the humanized antibodies, bispecific antibodies or compositions disclosed herein to treat the cancer.

Importantly, while IL13Rα2 is expressed by many cancer cells, it is not expressed by healthy tissues, with the exception of testes. Thus, the humanized antibodies or bispecific antibodies disclosed herein can be used as a targeting moiety to deliver therapeutics to cancer cells with low risk of off-target toxicity. In some embodiments, the methods further comprise determining whether IL13Rα2 is expressed on a cancer cell in the subject, and the humanized antibody or composition is only administered to the subject if IL13Rα2 expression is detected.

To determine whether IL13Rα2 is expressed on a cancer cell in the subject, a tissue sample or biopsy may be collected and analyzed using any standard method used to detect gene or protein expression. Suitable methods include, without limitation, Northern blot, western blot, in situ hybridization, immunohistochemistry, immunocytochemistry, reverse transcription polymerase chain reaction, microarray, RNA sequencing, and the like.

While the focus of the inventor's research is the treatment of glioblastoma, IL13Rα2 overexpression has been observed in a variety of tumor types, including colorectal cancer, renal cell carcinoma, pancreatic cancer, melanoma, head and neck cancer, mesothelioma, breast cancer, lung cancer, osteosarcoma, ovarian cancer, and metastases thereof (see, e.g., Cancers 2020, 12(2), 500). Any cancer type that expresses IL13Rα2 can be treated using the methods of the present invention. In a preferred embodiment, the cancer is glioblastoma.

The methods of the present invention may comprise an immunotherapy treatment, such as a vaccination, immune-checkpoint blockade, antibody-drug conjugates, tumor-infiltrating lymphocytes (TILs), bi-specific T-cell engagers (BTEs), or T cells modified with chimeric antigen receptors (CARs). For example, the humanized antibodies disclosed herein may be incorporated into reagents such as BTEs or CARs to give them the ability to target IL13Rα2-expressing cancer cells. Alternatively, the antibodies may be fused with the signaling domain of a T cell signaling protein (e.g., 4-1BB or CD3ζ) or a peptide modulator of T cell activation (e.g., IL-15 or IL-15Rα) to activate immune cell activity at the site of a tumor.

In addition, the antibodies may be used as targeting moieties used to deliver other therapeutics to cancer cells. To this end, the antibody may be conjugated to a therapeutic agent, as discussed above. Exemplary therapeutic agents for the treatment of cancer include cytotoxic and chemotherapeutic agents, such as platinum coordination compounds (e.g., cisplatin), topoisomerase inhibitors (e.g., topotecan, irinotecan and 9-amino-camptothecin), antibiotics (e.g., doxorubicin, mitomycin, bleomycin, daunorubicin and streptozocin), antimitotic alkaloids (e.g., vinblastine, vincristine, vindesine, Taxol and vinorelbine), and difluoronucleosides (e.g., 2'-deoxy-2',2'-difluorocytidine hydrochloride). However, the antibodies of the present invention may be used to target any chemotherapeutic agent to IL13Rα2-expressing cancer cells.

In one embodiment, the disclosed antibodies may be used as a targeting moiety by being linked to a peptide providing a second function, e.g., an effector function, such as a T cell signaling domain involved in T cell activation, a peptide that affects or modulates an immunological response to cancer cells, or an enzymatic component of a labeling system that results in a CAR encoded by a polynucleotide according to the disclosure. Exemplary conjugates include an anti-IL13Rα2 scFv linked to a hinge, a transmembrane domain, and an effector compound or domain, e.g., CD28, CD3ζ, CD134 (OX40), CD137 (41BB), ICOS, CD40, CD27, or Myd88, thereby yielding a CAR.

In some embodiments, the humanized antibody (being used as a targeting moiety) is used in a conjugate, wherein the conjugate further comprises an effector domain. As used herein, the term "effector domain" refers to a portion of a conjugate that effects a desired biological function.

In some embodiments, the effector domain is an apoptosis tag, for example, a TRAIL protein, or a portion thereof. An apoptosis tag is a tag that causes the IL13Rα2-expressing cell to apoptose.

In some embodiments, the effector domain is a label. Suitable labels include, for example, but not limited to, a radiolabel, a fluorescent label, an enzyme that catalyzes a calorimetric or fluorometric reaction, an enzymatic substrate, a solid matrix, biotin or avidin.

In another embodiment, the effector domain identifies or locates IL13Rα2-expressing cells. For example, the effector domain may be a diagnostic agent, e.g., a radiolabel, a fluorescent label, an enzyme (e.g., that catalyzes a calorimetric or fluorometric reaction), a substrate, a solid matrix, or a carrier (e.g., biotin or avidin). The diagnostic agent in some aspects is an imaging agent. Many appropriate imaging agents are known in the art, as are methods of attaching the labeling agents to the peptides of the invention (see, e.g., U.S. Pat. Nos. 4,965,392; 4,472,509; 5,021,236; and 5,037,630; each incorporated herein by reference). The imaging agents are administered to a subject in a pharmaceutically acceptable carrier, and allowed to accumulate at a target site having the lymphatic endothelial cells. This imaging agent then serves as a contrast reagent for X-ray, magnetic resonance, positron emission tomography, single photon emission computed tomography (SPECT), or sonographic or scintigraphic imaging of the target site. Imaging may occur in vitro or in vivo, for example, imaging may be performed in vitro where tissue from the subject is obtained through a biopsy, and the presence of IL13Rα2 positive cells is determined with the aid of the imaging agents described herein in combination with histochemical techniques for preparing and fixing tissues. Paramagnetic ions useful in the imaging agents of the invention include for example chromium (III), manganese (II), iron (III), iron (II), cobalt (II), nickel (II) copper (II), neodymium (III), samarium (III), ytterbium(III), gadolinium (III), vanadium (II), terbium (III), dysprosium (III), holmium (III) and erbium (III). Ions useful for X-ray imaging include, but are not limited to, lanthanum (III), gold (III), lead (II) and particularly bismuth (III). Radioisotopes for diagnostic applications include for example, $^{211}$astatine, $^{14}$carbon, $^{51}$chromium, $^{36}$chlorine, $^{57}$cobalt, $^{67}$copper, $^{152}$europium, $^{67}$gallium, $^{3}$hydrogen, $^{123}$iodine, $^{125}$iodine, $^{111}$indium, $^{59}$iron, $^{32}$phosphorus, $^{186}$rhenium, $^{75}$selenium, $^{35}$sulphur, $^{99}$mtechnicium, $^{90}$yttrium, and $^{89}$zirconium.

In another embodiment, the effector domain may be one that alters the physico-chemical characteristics of the conjugate, e.g., an effector that confers increased solubility and/or stability and/or half-life, resistance to proteolytic cleavage, modulation of clearance. In exemplary aspects, the effector domain is a polymer, a carbohydrate, or a lipid. The polymer may be branched or unbranched. The polymer may be of any molecular weight. The polymer in some embodiments has an average molecular weight of between about 2 kDa to about 100 kDa (the term "about" indicating that in preparations of a water-soluble polymer, some molecules will weigh more, some less, than the stated molecular weight). The average molecular weight of the polymer is in some aspects between about 5 kDa and about 50 kDa, between about 12 kDa to about 40 kDa or between about 20 kDa to about 35 kDa. In some embodiments, the polymer is modified to have a single reactive group, such as an active ester for acylation or an aldehyde for alkylation, so that the degree of polymerization may be controlled. The polymer in some embodiments is water-soluble so that the protein to which it is attached does not precipitate in an aqueous environment, such as a physiological environment. In some embodiments when, for example, the composition is used for therapeutic use, the polymer is pharmaceutically acceptable. Additionally, in some aspects, the polymer is a mixture of polymers, e.g., a co-polymer, a block co-polymer. In some embodiments, the polymer is selected from the group consisting of: polyamides, polycarbonates, polyalkylenes and derivatives thereof, including polyalkylene glycols, polyalkylene oxides, polyalkylene terepthalates, polymers of acrylic and methacrylic esters, including poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly (phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly (vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene. In some aspects, the polymer is a biodegradable polymer, including a synthetic biodegradable polymer (e.g., polymers of lactic acid and glycolic acid, polyanhydrides, poly(ortho)esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion. In some aspects, the polymer is a bioadhesive polymer, such as a bioerodible hydrogel described by H. S. Sawhney, C. P. Pathak and J. A Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly (octadecyl acrylate). In some embodiments, the polymer is a water-soluble polymer or a hydrophilic polymer. Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and combinations thereof. In some aspects, the water-soluble polymers or mixtures thereof include, but are not limited to, N-linked or O-linked carbohydrates, sugars, phosphates, carbohydrates; sugars; phosphates; polyethylene glycol (PEG) (including the forms of PEG that have been used to derivatize proteins, including mono-(C1-C10) alkoxy- or aryloxy-polyethylene glycol), monomethoxy-polyethylene glycol; dextran (such as low molecular weight dextran of, for example, about 6 kD), cellulose; other carbohydrate-based polymers, poly-(N-vinyl pyrrolidone), polyethylene glycol, propylene glycol homopolymers, a polypropylene oxide/ethylene oxide co-polymer, polyoxyethylated polyols (e.g., glycerol) and polyvinyl alcohol. Also encompassed by the disclosure are bifunctional crosslinking molecules that may be used to prepare covalently attached multimers. A particularly preferred water-soluble polymer for use herein is polyethylene glycol (PEG) As used herein, polyethylene glycol is meant to encompass any of the forms of PEG that can be used to derivatize other proteins, such as mono-(C1-C10) alkoxy- or aryloxy-polyethylene glycol. PEG is a linear or branched neutral polyether, available in a broad range of molecular weights, and is soluble in water and most organic solvents. PEG is effective at excluding other polymers or peptides when present in water, primarily through its high dynamic chain mobility and hydrophobic nature, thus creating a water shell or hydration sphere when attached to other proteins or polymer surfaces. PEG is nontoxic, non-immunogenic, and approved by the Food and Drug Administration for internal consumption. Proteins or enzymes when conjugated to PEG have demonstrated bioactivity, non-antigenic properties, and decreased clearance rates when administered in animals. F. M. Veronese et al., Preparation and Properties of Monomethoxypoly(ethylene glycol)-modified Enzymes for Therapeutic Applications, in J. M. Harris ed., Poly(Ethylene Glycol) Chemistry—Biotechnical and Biomedical Applications, 127-36, 1992, incorporated herein by reference. PEG in thought to prevent recognition by the immune system. In addition, PEG has been widely used in surface modification procedures to decrease protein adsorption and improve blood compatibility. S. W. Kim et al., Ann. N.Y. Acad. Sci. 516: 116-30 1987; Jacobs et al., Artif. Organs 12: 500-501, 1988; Park et al., J. Poly Sci, Part A 29:1725-31, 1991, each incorporated herein by reference in its entirety. Hydrophobic polymer surfaces, such as polyurethanes and polystyrene, can be modified by the grafting of PEG (MW 3,400) and employed as non-thrombogenic surfaces Surface properties (contact angle) can be more consistent with hydrophilic surfaces, due to the hydrating effect of PEG. More importantly, protein (albumin and other plasma proteins) adsorption can be greatly reduced, resulting from the high chain motility, hydration sphere, and protein exclusion properties of PEG. PEG (MW 3,400) was determined as an optimal size in surface immobilization studies, Park et al., J. Biomed. Mat. Res. 26:739-45, 1992, while PEG (MW 5,000) was most beneficial in decreasing protein antigenicity. F. M. Veronese et al., In J. M. Harris, et al., Poly(Ethylene Glycol) Chemistry—Biotechnical and Biomedical Applications, 127-36. Methods for preparing pegylated polypeptides (e.g., humanized antibody) may comprise the steps of (a) reacting the polypeptide with polyethylene glycol (such as a reactive ester or aldehyde derivative of PEG) under conditions whereby the humanized antibody polypeptide becomes attached to one or more PEG groups, and (b) obtaining the reaction product(s). In general, the optimal reaction conditions for the acylation reactions will be determined based on known parameters and the desired result. For example, the larger the ratio of PEG:protein, the greater the percentage of poly-pegylated product. In some embodiments, the humanized antibody will have a single PEG moiety at the N-terminus. See U.S. Pat. No. 8,234,784, incorporated by reference herein.

In some embodiments, the effector domain is a carbohydrate. In some embodiments, the carbohydrate is a monosaccharide (e.g., glucose, galactose, fructose), a disaccharide (e.g., sucrose, lactose, maltose), an oligosaccharide (e.g., raffinose, stachyose), a polysaccharide (e.g., a starch, amylase, amylopectin, cellulose, chitin, callose, laminarin, xylan, mannan, fucoidan, or galactomannan). In some embodiments, the effector domain is a lipid. The lipid, in some embodiments, is a fatty acid, eicosanoid, prostaglandin, leukotriene, thromboxane, N-acyl ethanolamine, glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide, oil, wax, cholesterol, sterol, fat-soluble vitamin. monoglyceride, diglyceride, triglyceride, or a phospholipid.

In another exemplary embodiment, the effector domain is a lethal domain that confers lethality, such that when the conjugate is localized to a cell expressing IL13Rα2, e.g., a tumor cell expressing IL13Rα2. The effector domain confers upon the conjugate the ability to kill an IL13Rα2-expressing cell once the humanized antibody has found and bound to its IL13Rα2 target.

In exemplary embodiments, the effector domain is a cytotoxin (also referred to herein as a "cytotoxic agent"). The cytotoxic agent is any molecule (chemical or biochemical) which is toxic to a cell. In some embodiments, the cytotoxic agent is a chemotherapeutic agent. Chemotherapeutic agents are known in the art and include, but are not limited to, platinum coordination compounds, topoisomerase inhibitors, antibiotics, antimitotic alkaloids and difluoronucleosides, as described in U.S. Pat. No. 6,630,124. In some embodiments, the chemotherapeutic agent is a platinum coordination compound. The term "platinum coordination compound" refers to any tumor cell growth-inhibiting platinum coordination compound that provides the platinum in the form of an ion. In some embodiments, the platinum coordination compound is cis-diamminediaquoplatinum (II)-ion; chloro(diethylenetriamine)-platinum(II) chloride; dichloro(ethylenediamine)-platinum(II), diammine(1,1-cyclobutanedicarboxylato) platinum(II) (carboplatin); spiroplatin; iproplatin; diammine(2-ethylmalonato)-platinum(II); ethylenediaminemalonatoplatinum (II); aqua(1,2-diaminodyclohexane)-sulfatoplatinum(II); (1,2-diaminocyclohexane)malonatoplatinum(II); (4-caroxyphthalato)(1,2-diaminocyclohexane)platinum(II); (1,2-diaminocyclohexane)-(isocitrato)platinum(II), (1,2-diaminocyclohexane)cis(pyruvato)platinum(II); (1,2-diaminocyclohexane)oxalatoplatinum(II); ormaplatin; or tetraplatin. In some embodiments, cisplatin is the platinum coordination compound employed in the compositions and methods of the present invention. Cisplatin is commercially available under the name PLATINOL™ from Bristol Myers-Squibb Corporation and is available as a powder for constitution with water, sterile saline or other suitable vehicle Other platinum coordination compounds suitable for use in the present invention are known and are available commercially and/or can be prepared by conventional techniques. Cisplatin, or cis-dichlorodiammineplatinum II, has been used successfully for many years as a chemotherapeutic agent in the treatment of various human solid malignant tumors. More recently, other diamino-platinum complexes have also shown efficacy as chemotherapeutic agents in the treatment of various human, solid, malignant tumors. Such diamino-platinum complexes include, but are not limited to, spiroplatinum and carboplatinum. Although cisplatin and other diamino-platinum complexes have been widely used as chemotherapeutic agents in humans, they have had to be delivered at high dosage levels that can lead to toxicity problems such as kidney damage.

In some embodiments, the chemotherapeutic agent is a topoisomerase inhibitor. Topoisomerases are enzymes that are capable of altering DNA topology in eukaryotic cells. They are critical for cellular functions and cell proliferation. Generally, there are two classes of topoisomerases in eukaryotic cells, type I and type II Topoisomerase I is a monomeric enzyme of approximately 100,000 molecular weight. The enzyme binds to DNA and introduces a transient single-strand break, unwinds the double helix (or allows it to unwind), and subsequently reseals the break before dissociating from the DNA strand. Various topoisomerase inhibitors have recently shown clinical efficacy in the treatment of humans afflicted with ovarian cancer, esophageal cancer or non-small cell lung carcinoma. In some aspects, the topoisomerase inhibitor is camptothecin or a camptothecin analog. Camptothecin is a water-insoluble, cytotoxic alkaloid produced by *Camptotheca accuminata* trees indigenous to China and *Nothapodytes foetida* trees indigenous to India. Camptothecin exhibits tumor cell growth-inhibiting activity against a number of tumor cells Compounds of the camptothecin analog class are typically specific inhibitors of DNA topoisomerase I. By the term "inhibitor of topoisomerase" is meant any tumor cell growth-inhibiting compound that is structurally related to camptothecin. Compounds of the camptothecin analog class include, but are not limited to; topotecan, irinotecan and 9-amino-camptothecin. In additional embodiments, the cytotoxic agent is any tumor cell growth-inhibiting camptothecin analog claimed or described in U.S. Pat. No. 5,004,758; European Patent Application Number 88311366.4 (Publication Number EP 0 321 122): U.S. Pat. No. 4,604,463; European Patent Application Publication Number EP 0 137 145, U.S. Pat. No. 4,473,692; European Patent Application Publication Number EP 0 074 256; U.S. Pat. No. 4,545,880; European Patent Application Publication Number EP 0 074 256; European Patent Application Publication Number EP 0 088 642; Wani et al., J. Med. Chem., 29, 2358-2363 (1986); and Nitta et al., Proc. 14th International Congr. Chemotherapy, Kyoto, 1985, Tokyo Press, Anticancer Section 1, p. 28-30. In particular, the disclosure contemplates a compound called CPT-11. CPT-11 is a camptothecin analog with a 4-(piperidino)-piperidine side chain joined through a carbamate linkage at C-10 of 10-hydroxy-7-ethyl camptothecin. CPT-11 is currently undergoing human clinical trials and is also referred to as irinotecan; Wani et al, J. Med. Chem., 23, 554 (1980); Wani et. al., J. Med. Chem., 30, 1774 (1987); U.S. Pat. No. 4,342,776; European Patent Application Publication Number EP 418 099, U.S. Pat. No. 4,513,138; European Patent Application Publication Number EP 0 074 770, U.S. Pat. No. 4,399,276; European Patent Application Publication Number 0 056 692; the entire disclosure of each of which is hereby incorporated by reference. All of the above-listed compounds of the camptothecin analog class are available commercially and/or can be prepared by conventional techniques including those described in the above-listed references. The topoisomerase inhibitor may be selected from the group consisting of topotecan, irinotecan and 9-aminocamptothecin.

The preparation of numerous compounds of the camptothecin analog class (including pharmaceutically acceptable salts, hydrates and solvates thereof) as well as the preparation of oral and parenteral pharmaceutical compositions comprising such a compound of the camptothecin analog class and an inert, pharmaceutically acceptable carrier or diluent, is extensively described in U.S. Pat. No. 5,004,758; and European Patent Application Number 88311366.4 (Publication Number EP 0 321 122), the teachings of each of which are incorporated herein by reference in its entirety.

In still another embodiment, the chemotherapeutic agent is an antibiotic compound. Suitable antibiotics include, but are not limited to, doxorubicin, mitomycin, bleomycin, daunorubicin and streptozocin. In some embodiments, the chemotherapeutic agent is an antimitotic alkaloid. In general, antimitotic alkaloids can be extracted from *Catharanthus roseus*, and have been shown to be efficacious as anticancer chemotherapy agents. A great number of semi-synthetic derivatives have been studied both chemically and pharmacologically (see, O. Van Tellingen et al, Anticancer Research, 12, 1699-1716 (1992)). The antimitotic alkaloids of the present invention include, but are not limited to, vinblastine, vincristine, vindesine, Taxol and vinorelbine. The latter two antimitotic alkaloids are commercially available from Eli Lilly and Company, and Pierre Fabre Laboratories, respectively (see, U.S. Pat. No. 5,620,985). In one aspect of the disclosure, the antimitotic alkaloid is vinorelbine.

In another embodiment, the chemotherapeutic agent is a difluoronucleoside. 2'-deoxy-2',2'-difluoronucleosides are known in the art as having antiviral activity. Such compounds are disclosed and taught in U.S. Pat. Nos. 4,526,988 and 4,808,614. European Patent Application Publication 184,365 discloses that these same difluoronucleosides have oncolytic activity. In certain specific aspects, the 2'-deoxy-2',2'-difluoronucleoside used in the compositions and methods of the disclosure is 2'-deoxy-2',2'-difluorocytidine hydrochloride, also known as gemcitabine hydrochloride. Gemcitabine is commercially available or can be synthesized in a multi-step process as disclosed in U.S. Pat. Nos. 4,526,988, 4,808,614 and 5,223,608, the teachings of each of which are incorporated herein by reference in its entirety.

In another exemplary embodiment, the effector domain is an Fe domain of IgG or other immunoglobulin. For substituents such as an Fc region of human IgG, the fusion can be fused directly to humanized antibody described herein or fused through an intervening sequence. For example, a human IgG hinge, CH2 and CH3 region may be fused at either the N-terminus or C-terminus of the humanized antibody to attach the Fc region. The resulting Fc-fusion agent enables purification via a Protein A affinity column (Pierce, Rockford, Ill.). Peptide and proteins fused to an Fc region can exhibit a substantially greater half-life in vivo than the unfused counterpart. A fusion to an Fc region allows for dimerization/multimerization of the fusion polypeptide. The Fc region may be a naturally occurring Fc region, or may be modified for superior characteristics, e.g., therapeutic qualities, circulation time, reduced aggregation. As noted above, in some embodiments, the humanized antibodies are conjugated, e.g., fused to an immunoglobulin or portion thereof (e.g., variable region, CDR, or Fc region) Known types of immunoglobulins (Ig) include IgG, IgA, IgE, IgD or IgM. The Fc region is a C-terminal region of an Ig heavy chain, which is responsible for binding to Fc receptors that carry out activities such as recycling (which results in prolonged half-life), antibody dependent cell-mediated cytotoxicity (ADCC), and complement dependent cytotoxicity (CDC).

For example, according to some definitions the human IgG heavy chain Fc region stretches from Cys226 to the C-terminus of the heavy chain. The "hinge region" generally extends from Glu216 to Pro230 of human IgG1 (hinge regions of other IgG isotypes may be aligned with the IgG1 sequence by aligning the cysteines involved in cysteine bonding). The Fc region of an IgG includes two constant domains, CH2 and CH3. The CH2 domain of a human IgG Fc region usually extends from amino acids 231 to amino acid 341. The CH3 domain of a human IgG Fc region usually extends from amino acids 342 to 447. References made to amino acid numbering of immunoglobulins or immunoglobulin fragments, or regions, are all based on Kabat et al. 1991, Sequences of Proteins of Immunological Interest, U.S. Department of Public Health, Bethesda, Md., incorporated herein by reference. In related embodiments, the Fc region may comprise one or more native or modified constant regions from an immunoglobulin heavy chain, other than CH1, for example, the CH2 and CH3 regions of IgG and IgA, or the CH3 and CH4 regions of IgE.

Suitable conjugate moieties include portions of immunoglobulin sequence that include the FcRn binding site. FcRn, a salvage receptor, is responsible for recycling immunoglobulins and returning them to circulation in the blood. The region of the Fc portion of IgG that binds to the FcRn receptor has been described based on X-ray crystallography (Burmeister et al 1994, Nature 372:379). The major contact area of the Fc with the FcRn is near the junction of the CH2 and CH3 domains. Fc-FcRn contacts are all within a single Ig heavy chain. The major contact sites include amino acid residues 248, 250-257, 272, 285, 288, 290-291, 308-311, and 314 of the CH2 domain and amino acid residues 385-387, 428, and 433-436 of the CH3 domain.

Some conjugate moieties may or may not include FcγR binding site(s). FcγR are responsible for antibody-dependent cell-mediated cytotoxicity (ADCC) and complement-dependent cytotoxicity (CDC). Examples of positions within the Fc region that make a direct contact with FcγR are amino acids 234-239 (lower hinge region), amino acids 265-269 (B/C loop), amino acids 297-299 (C'/E loop), and amino acids 327-332 (F/G) loop (Sondermann et al, Nature 406: 267-273, 2000). The lower hinge region of IgE has also been implicated in the FcRI binding (Henry, et al., Biochemistry 36, 15568-15578, 1997). Residues involved in IgA receptor binding are described in Lewis et al., (J Immunol. 175:6694-701, 2005). Amino acid residues involved in IgE receptor binding are described in Sayers et al. (J Biol Chem. 279 (34):35320-5, 2004).

Amino acid modifications may be made to the Fc region of an immunoglobulin. Such variant Fc regions comprise at least one amino acid modification in the CH3 domain of the Fc region (residues 342-447) and/or at least one amino acid modification in the CH2 domain of the Fc region (residues 231-341). Mutations believed to impart an increased affinity for FcRn include T256A, T307A, E380A, and N434A (Shields et al. 2001, J. Biol Chem. 276:6591) Other mutations may reduce binding of the Fc region to FcγRI, FcγRIIA, FcγRIIB, and/or FcγRIIIA without significantly reducing affinity for FcRn. For example, substitution of the Asn at position 297 of the Fc region with Ala or another amino acid removes a highly conserved N-glycosylation site and may result in reduced immunogenicity with concomitant prolonged half-life of the Fc region, as well as reduced binding to FcγRs (Routledge et al. 1995, Transplantation 60:847: Friend et al. 1999, Transplantation 68:1632, Shields et al. 1995, J. Biol. Chem. 276:6591) Amino acid modifications at positions 233-236 of IgG1 have been made that reduce binding to FcγRs (Ward and Ghetie 1995, Therapeutic Immunology 2:77 and Armour et al. 1999, Eur. J. Immunol 29:2613). Some exemplary amino acid substitutions are described in U.S. Pat. Nos. 7,355,008 and 7,381,408, each of which is incorporated by reference herein in its entirety.

In some embodiments, the humanized antibody is fused to alkaline phosphatase (AP). Methods for making Fc or AP fusion agents are provided in WO 02/060950.

In another exemplary embodiment, the effector domain is a T-cell signaling domain. For example, the conjugate is a chimeric antigen receptor (CAR). Chimeric antigen receptors (CARs) are engineered transmembrane proteins that combine the specificity of an antigen-specific antibody with a T-cell receptor's function. In general, CARs comprise an ectodomain, a transmembrane domain, and an endodomain. The ectodomain of a CAR in some embodiments may comprise an antigen recognition region, which may be the humanized scFV described herein. The ectodomain also in some embodiments comprises a signal peptide that directs the nascent protein into the endoplasmic reticulum. In exemplary embodiments, the ectodomain comprises a spacer that links the humanized antibody described herein to the transmembrane domain. The transmembrane (TM) domain is the portion of the CAR that traverses the cell membrane. In exemplary embodiments, the TM domain comprises a hydrophobic alpha helix. In exemplary embodiments, the TM domain comprises all or a portion of the TM domain of CD28. In exemplary embodiments, the TM domain comprises all or a portion of the TM domain of CD8α. The endodomain of a CAR comprises one or more signaling domains. In exemplary embodiments, the endodomain comprises the zeta chain of CD3, which comprises three copies of the Immunoreceptor Tyrosine-based Activation Motif (ITAM). An ITAM generally comprises a Tyr residue separated by two amino acids from a Leu or Ile. In the case of immune cell receptors, e.g., the T cell receptor and the B cell receptor, the ITAMs occur in multiples (at least two) and each ITAM is separated from another by 6-8 amino acids. The endodomain of CARs may also comprises additional signaling domains, e.g., portions of proteins that are important for downstream signal transduction. In exemplary embodiments, the endodomain comprises signaling domains from one or more of CD28, 41BB or 4-1BB (CD137), ICOS, CD27, CD40, OX40 (CD134), or Myd88. Sequences encoding signaling domains of such proteins are provided herein as SEQ ID NOs:39-42, 68-79, 81, and 83. Methods of making CARs, expressing them in cells, e.g, T-cells, and utilizing the CAR-expressing T-cells in therapy, are known in the art See, e.g, International Patent Application Publication Nos. WO2014/208760, WO2014/190273, WO2014/186469, WO2014/184143, WO2014180306, WO2014/179759, WO2014/153270, US Application Publication Nos. US20140369977, US20140322212, US20140322275, US20140322183, US20140301993, US20140286973, US20140271582, US20140271635, US20140274909, European Application Publication No. 2814846, each of which are incorporated by reference in their entirety.

In exemplary embodiments, the conjugate of the disclosure is an IL13Rα2-specific chimeric antigen receptor (CAR) comprising the humanized antibody described herein, a hinge region, and an endodomain comprising a signaling domain of a CD3 zeta chain and a signaling domain of CD28, CD134, and/or CD137. In exemplary embodiments, the CAR comprises (A) humanized antibody described herein, (B) a hinge region; and (C) an endodomain comprising a signaling domain of a CD3 zeta chain and a signaling domain of CD28, CD134, and/or CD137. In exemplary embodiments, the CAR further comprises a transmembrane (TM) domain based on the TM domain of CD8α. In exemplary embodiments, the endodomain further comprises a signaling domain of one or more of: CD137, CD134, CD27, CD40, ICOS, and Myd88.

In exemplary embodiments, the CAR comprises (A) the humanized antibody described herein; (B) a hinge region; (C) an endodomain comprising a signaling domain of a CD3 zeta chain and a signaling domain of CD28 and at least one other signaling domain. In one embodiment, the CAR comprises an endodomain comprising a signaling domain of 41BB (CD137). In another embodiment, the CAR comprises an endodomain comprising a signaling domain of OX40 (CD134). In another embodiment, the CD137 signaling is N-terminal to a CD3 zeta chain signaling chain. In another embodiment, the CAR comprises (A) the humanized antibody described herein, (B) a hinge region; (C) a transmembrane domain of CD8α chain, and (D) an endodomain comprising a signaling domain of a CD3 zeta chain, and, optionally, at least one other signaling domain. In one embodiment, the CAR further comprises a CD137 signaling domain and a CD3 zeta chain signaling domain. In some embodiments, the humanized antibodies or compositions are administered through an intravenous injection or through intra-peritoneal and subcutaneous methods. Such methods include administering a therapeutic agent to a subject in combination with an antibody or composition, such that the antibody targets delivery of the agent to an IL13Rα2-expressing cell. In another embodiment, the humanized antibodies or compositions are administered intra-tumorally to the site of the tumor.

In another embodiment, the disclosure provides a method for inducing lysis of a target cell, particularly a tumor cell, comprising contacting the target cell with a bispecific antibody described herein in the presence of a T cell, particularly a cytotoxic T cell. In some embodiments, the method is done in vivo in a subject having a tumor, particularly in some embodiments, glioblastoma.

DEFINITIONS

Administering. As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, intradermal administration, intrathecal administration, and subcutaneous administration. Administration can be continuous or intermittent.

Antigen. The term "antigen," as used herein, refers to any molecule that is recognized by the immune system and that can stimulate an immune response.

Chimeric antibody. The term "chimeric antibody" refers to an antibody comprising a variable region (i.e., binding region) from one source or species and at least a portion of a constant region derived from a different source or species.

Other forms of "chimeric antibodies" are those in which the class or subclass has been modified or changed from that of the original antibody. Such "chimeric" antibodies are also referred to as "class-switched antibodies." Methods for producing chimeric antibodies involve conventional recombinant DNA and gene transfection techniques, which are now well known in the art. For example, chimeric antibodies are commonly isolated from a host cell (e.g., an SP2-0, NS0 or CHO cell) or from an animal (e.g., a mouse) that is transgenic for immunoglobulin genes or antibodies.

Complementarity determining region (CDR). The term "complementarity determining region" or "CDR," as used herein, refers to part of the variable chains in immunoglobulins (antibodies) and T cell receptors where these molecules bind to their specific antigen. As the most variable parts of the molecules, CDRs are crucial to the diversity of antigen specificities generated by lymphocytes. There are three CDRs (CDR1, CDR2 and CDR3), arranged non-consecutively, on the amino acid sequence of a variable domain of an antigen receptor. Since the antigen receptors are typically composed of two variable domains (on two different polypeptide chains: the heavy and light chain), there are six CDRs for each antigen receptor that can collectively come into contact with the antigen. A single whole antibody molecule has two antigen receptors and therefore contains twelve CDRs. Sixty CDRs can be found on a pentameric IgM molecule. Within the variable domain, CDR1 and CDR2 may be found in the variable (V) region of a polypeptide chain, and CDR3 includes some of V, all of diversity (D, heavy chains only) and joining (J) regions. Since most sequence variation associated with immunoglobulins and T cell receptors is found in the CDRs, these regions are sometimes referred to as hypervariable regions. Among these, CDR3 shows the greatest variability as it is encoded by a recombination of VJ in the case of a light chain region and VDJ in the case of heavy chain regions.

Monoclonal antibody. The terms "monoclonal antibody" or "monoclonal antibody composition" as used herein refer to a preparation of antibody molecules of a single amino acid composition. Monoclonal antibodies also include "human monoclonal antibodies", which display a single binding specificity and have variable and constant regions derived from human germline immunoglobulin sequences. Human monoclonal antibodies can be produced by a hybridoma, which includes a B cell obtained from a transgenic nonhuman animal (e.g., a transgenic mouse) having a genome comprising a human heavy chain transgene and a human light chain transgene fused to an immortalized cell.

Percentage of sequence similarity. "Percentage of sequence similarity" or "percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Protein and nucleic acid sequence identities are evaluated using the Basic Local Alignment Search Tool ("BLAST"), which is well known in the art (Karlin and Altschul, 1990, *Proc. Natl. Acad. Sci. USA* 87: 2267-2268; Altschul et al., 1997, *Nucl. Acids Res.* 25: 3389-3402). The BLAST programs identify homologous sequences by identifying similar segments, which are referred to herein as "high-scoring segment pairs," between a query amino or nucleic acid sequence and a test sequence which is preferably obtained from a protein or nucleic acid sequence database. Preferably, the statistical significance of a high-scoring segment pair is evaluated using the statistical significance formula (Karlin and Altschul, 1990), the disclosure of which is incorporated by reference in its entirety. The BLAST programs can be used with the default parameters or with modified parameters provided by the user. The term "substantial identity" of amino acid sequences for purposes of this invention normally means polypeptide sequence identity of at least 40%. Preferred percent identity of polypeptides can be any integer from 40% to 100%. More preferred embodiments include at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100%.

Protein. The terms "protein" and "polypeptide" are used interchangeably herein to designate a series of amino acid residues connected to by peptide bonds between the alpha-amino and carboxy groups of adjacent residues. The terms "protein" and "polypeptide" refer to a polymer of protein amino acids, including modified amino acids (e.g., phosphorylated, glycated, glycosylated, etc.) and amino acid analogs. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to an encoded gene product and fragments thereof. Thus, exemplary polypeptides or proteins include gene products, naturally occurring proteins, homologs, orthologs, paralogs, fragments and other equivalents, variants, fragments, and analogs of the foregoing. The antibodies of the present invention are polypeptides.

Nucleic Acid. The term "nucleic acid" as used herein includes "polynucleotide," "oligonucleotide," and "nucleic acid molecule," and generally means a polymer of DNA or RNA, which may be single-stranded or double-stranded, synthesized or obtained (e.g., isolated and/or purified) from natural sources, which may contain natural, non-natural or altered nucleotides, and which may contain a natural, non-natural or altered internucleotide linkage, such as a phosphoroamidate linkage or a phosphorothioate linkage, instead of the phosphodiester found between the nucleotides of an unmodified oligonucleotide.

Subject. As used herein, "subject" or "patient" refers to mammals and non-mammals. A "mammal" may be any member of the class Mammalia including, but not limited to, humans, non-human primates (e.g., chimpanzees, other apes, and monkey species), farm animals (e.g., cattle, horses, sheep, goats, and swine), domestic animals (e.g., rabbits, dogs, and cats), or laboratory animals including rodents (e.g., rats, mice, and guinea pigs). Examples of non-mammals include, but are not limited to, birds, and the like. The term "subject" does not denote a particular age or sex. In one specific embodiment, a subject is a mammal, preferably a human. In a preferred embodiment, the human has IL13Rα2 expressing tumor. In one example, the subject has glioblastoma.

Therapeutic agent. As used herein, the term "therapeutic agent" refers to any synthetic or naturally occurring biologically active compound or composition of matter which, when administered to a subject, induces a desired pharmacologic, immunogenic, and/or physiologic effect by local and/or systemic action. The term, therefore, encompasses those compounds or chemicals traditionally regarded as drugs, chemotherapeutics, and biopharmaceuticals including molecules such as proteins, peptides, hormones, nucleic acids, gene constructs and the like. Examples of therapeutic agents are described in well-known literature references, such as the Merck Index (14th edition), the Physicians' Desk Reference (64th edition), and The Pharmacological Basis of Therapeutics (12th edition), and they include, without limitation, substances used for the treatment, prevention, diagnosis, cure or mitigation of a disease or illness; substances that affect the structure or function of the body, or pro-drugs, which become biologically active or more active after they have been placed in a physiological environment.

Treating. As used herein, "treating" or "treatment" describes the management and care of a subject for the purpose of combating a disease, condition, or disorder. Treating includes the administration of an antibody or composition of present invention to prevent the onset of the symptoms or complications, to alleviate the symptoms or complications, or to eliminate the disease, condition, or disorder. Specifically, the antibodies or compositions disclosed herein can be used to treat a cancer that expresses IL13Rα2.

Therapeutically effective amount. The terms "effective amount" or "therapeutically effective amount" refer to an amount sufficient to effect beneficial or desirable biological or clinical results. That result can be reducing, alleviating, inhibiting or preventing one or more symptoms of a disease or condition, reducing, inhibiting or preventing the growth of cancer cells, reducing, inhibiting or preventing metastasis of the cancer cells or invasiveness of the cancer cells or metastasis, or reducing, alleviating, inhibiting or preventing one or more symptoms of the cancer or metastasis thereof, or any other desired alteration of a biological system. In some embodiments, the effective amount is an amount suitable to provide the desired effect, e.g., anti-tumor response. An anti-tumor response may be demonstrated, for example, by a decrease in tumor size or an increase in immune cell activation (e.g., CD8+ T cell activation).

Vector. The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors". Vectors comprise the nucleotide sequence encoding the antibodies described herein and a heterogeneous sequence necessary for proper propagation of the vector and expression of the encoded polypeptide. The heterogeneous sequence (i.e., sequence from a difference species than the polypeptide) can comprise a heterologous promoter or heterologous transcriptional regulatory region that allows for expression of the polypeptide. As used herein, the terms "heterologous promoter," "promoter," "promoter region," or "promoter sequence" refer generally to transcriptional regulatory regions of a gene, which may be found at the 5' or 3' side of the polynucleotides described herein, or within the coding region of the polynucleotides, or within introns in the polynucleotides. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site, as well as protein binding domains (consensus sequences) responsible for the binding of RNA polymerase.

Expression vectors include all those known in the art including, without limitation, a yeast artificial chromosome, bacterial plasmid (e.g., naked or contained in liposomes), phagemid, shuttle vector, cosmid, virus (e.g., Sendai viruses, lentiviruses, retroviruses, adenoviruses, and adeno-associated viruses), chromosome, mitochondrial DNA, plastid DNA, and nucleic acid fragment. Generally, an expression vector comprises sufficient cis-acting elements for expression; other elements for expression can be supplied by the host cell or in an in vitro expression system.

The present invention has been described in terms of one or more preferred embodiments, and it should be appreciated that many equivalents, alternatives, variations, and modifications, aside from those expressly stated, are possible and within the scope of the invention.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

The invention will be more fully understood upon consideration of the following non-limiting examples.

EXAMPLES

Example 1: Antibody Expression

The aim of this project is to humanize a mouse monoclonal antibody (mAb) using CDR grafting method without sacrificing the binding affinity of the parent antibody. The following experiments are presented in this Example:

1. Confirmation of antigen-antibody interaction
2. Humanized antibody design and construction
3. Selection of Humanized Antibodies Materials:

pCDNA3.4 expression vector and Expi293F cell (prepared by GenScript)

Biological safety cabinet (Thermo Scientific, Model. 1384)

Zhichu CO2 shaker incubator (Shanghai Zhichu Instrument, Model. ZCZY-BS8)

Expi293F medium (Gibco, Cat. No. A14351-01)

ExpiFectamine293 Transfection Kit (Gibco, Cat. No. A14525)
TPP Tubespin Bioreactor 50 (Cat. No. 87050)
125-ml shake flask (Corning, Cat. No. 431143)
500-ml shake flask (Corning, Cat. No. 431145)
Protein-A resin (GenScript, Cat. No. L0443)
Binding buffer: 0.15 M NaCl, 20 mM Na2HPO4, pH 7.0
Elution buffer: 0.1 M Glycine-HCl, pH 2.5
Neutralization buffer: 1 M Tris-HCl, pH 9.0
Biacore T200/Biacore 8K (GE Healthcare)
Series S Sensor Chip Protein A (GE Healthcare, Cat. No.:29-1275-55)
HBS-EP: 10 mM HEPES, 150 mM NaCl, 3 mM EDTA, 0.005% Tween 20, pH 7.4
10 mM Glycine-HCl
Amino acid sequences of parental antibody
Human IL13Rα2

Methods:

Construction and Production of Chimeric Antibody

The DNA sequences encoding the chimeric antibody heavy and light chains were synthesized and inserted into the pCDNA3.4 vector to construct expression plasmids of full-length IgGs. Expression of chimeric antibody was conducted in Expi293F cell culture, and the supernatants were purified using an affinity purification column. The purified antibody was buffer-exchanged into PBS using dialysis bag. The concentration and purity of the purified protein was determined by OD280 and SDS-PAGE, respectively.

Binding Confirmation of Chimeric Antibody

The affinity of chimeric antibody to the antigen human IL13Rα2 was determined using a surface plasmon resonance (SPR) biosensor, Biacore T200 (GE Healthcare). Antibody was immobilized on the sensor chip through Fc capture method. Human IL13Rα2 was used as the analyte with association time of 180 s and buffer flow was maintained for 600 s for dissociation. The data of dissociation ($k_d$) and association ($k_a$) rate constants were obtained using Biacore T200 evaluation software. The equilibrium dissociation constants ($K_D$) were calculated from the ratio of $k_d$ over $k_a$.

Humanization Design of Mouse Antibody

The humanized heavy chain and light chain were designed as described in design report. The designed plasmids of heavy chain and light chain were synthesized following GenScript's standard operating procedures (SOP).

Production and Affinity Ranking of Humanized Antibodies

The designed plasmids of heavy chain and light chain were sent for 5 mL transfection following GenScript's standard operating procedures (SOP). For affinity ranking, antibodies were immobilized on the sensor chip through Fc capture method. Human IL13Rα2 was used as the analyte. The surface was regenerated before the injection of another antibody. The process was repeated until all antibodies are analyzed. The off-rates of antibodies were obtained from fitting the experimental data locally to 1:1 interaction model using the Biacore 8K evaluation software. The antibodies were ranked by their dissociation rate constants (off-rates, k). Based on the ranked results, the top three clones were selected.

Construction and Production of Humanized IgGs

The top three clones were selected and expressed in Expi293F cell culture. The recombinant IgGs secreted to the medium were purified using resin A affinity chromatography following GenScript's SOP.

Affinity Measurement of Purified Humanized IgGs

The affinity of purified antibodies binding to human IL13Rα2 was individually determined using Biacore T200. Antibodies were immobilized on the sensor chip through Fc capture method. Human IL13Rα2 was used as the analyte. The data of dissociation ($k_d$) and association ($k_a$) rate constants were obtained using Biacore T200 evaluation software. The equilibrium dissociation constants ($K_D$) were calculated from the ratio of $k_d$ over $k_a$.

Results:

Chimeric Antibody Production

Chimeric antibody was expressed and purified according to GenScript's SOP, respectively. The purified IgG migrated as ~150 kDa band in SDS-PAGE under non-reducing conditions. Based on the SDS-PAGE result, the purity of IgG is >95% (FIG. 1). The yield of purified IgG from 100 ml cell culture was ~3.28 mg.

Binding Confirmation of Chimeric Antibody by SPR

Figure 2:
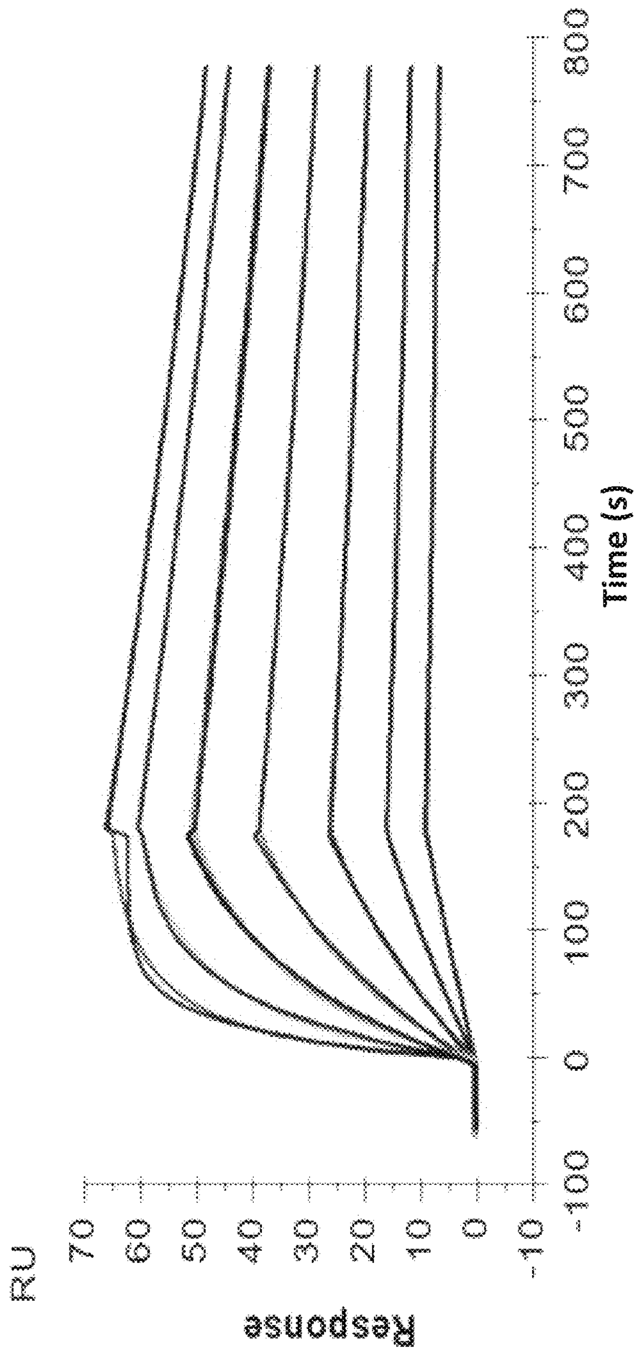
FIG. 2 shows sensor-grams of human IL13Rα2 binding to chimeric antibodies. Real-time responses are shown with colored curves. A fitting of Biacore experimental data to a 1:1 interaction model is shown in black. The antigen concentrations were 1.875, 3.75, 7.5, 15, 30, 60, 120 nM, respectively.

The results indicate that chimeric antibody can bind to the Human IL13Rα2. The affinity and kinetics of human IL13Rα2 binding to Chimeric IgG are summarized in Table 1 and the sensor-grams are shown in FIG. 2.

TABLE 1

The affinity and kinetics of human IL13Rα2 binding to chimeric IgG.

| Ligand | Analyte | $k_a$ (1/Ms) | $k_d$ (1/s) | $K_D$ (M) | Rmax | $Chi^2(RU^2)$ |
|---|---|---|---|---|---|---|
| Chimeric | Human IL13Rα2 | 3.63E+05 | 5.23E−04 | 1.44E−09 | 66.51 | 0.196 |

Affinity Ranking of Humanized Antibodies

Figure 3:
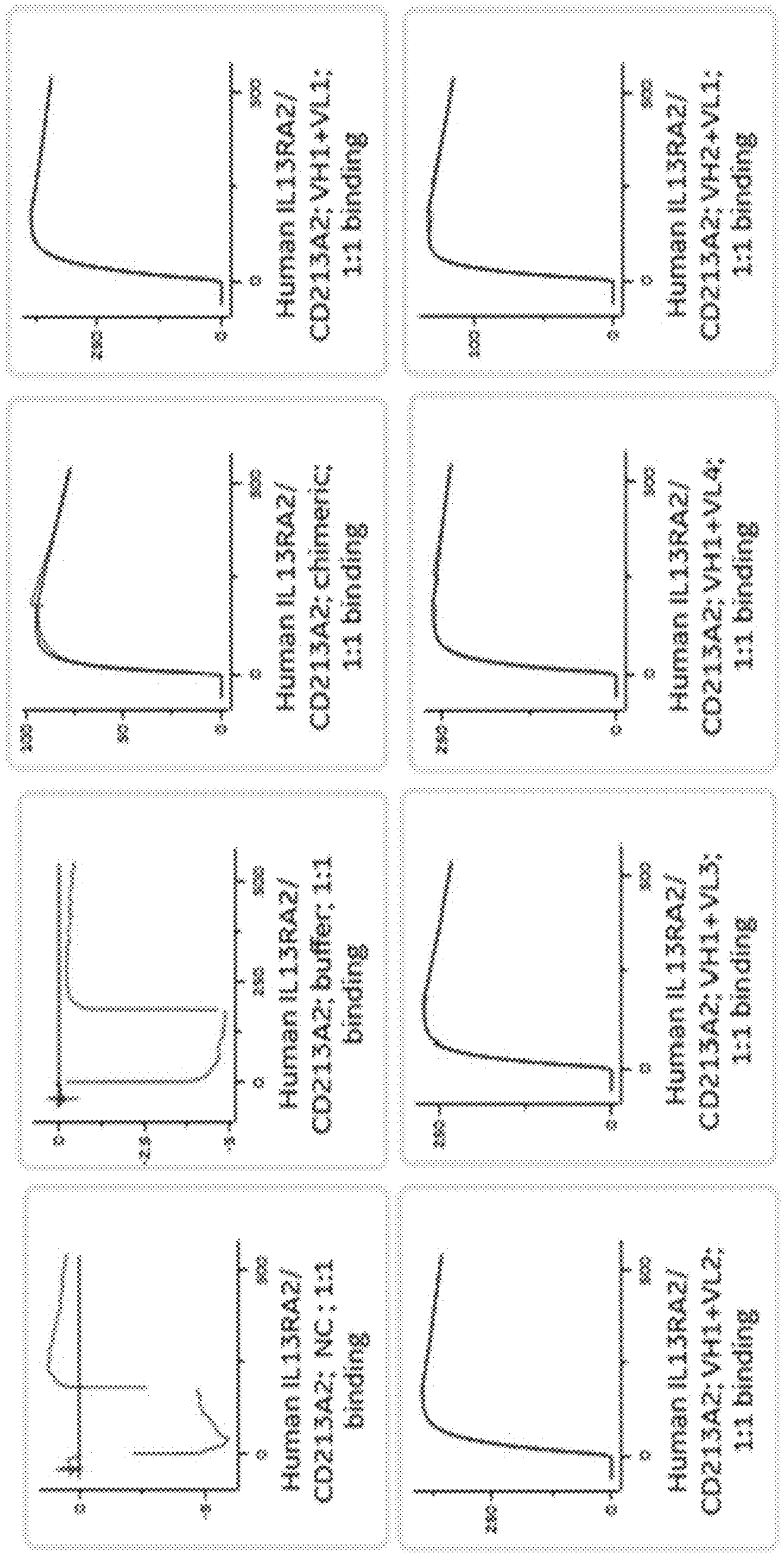
FIG. 3 shows sensor-grams of human IL13Rα2 binding to humanized antibodies. Real-time responses are shown with a red curve. A fitting of Biacore experimental data to a 1:1 interaction model is shown in black. The human IL13Rα2 concentration was 100 nM.
Figure 3:
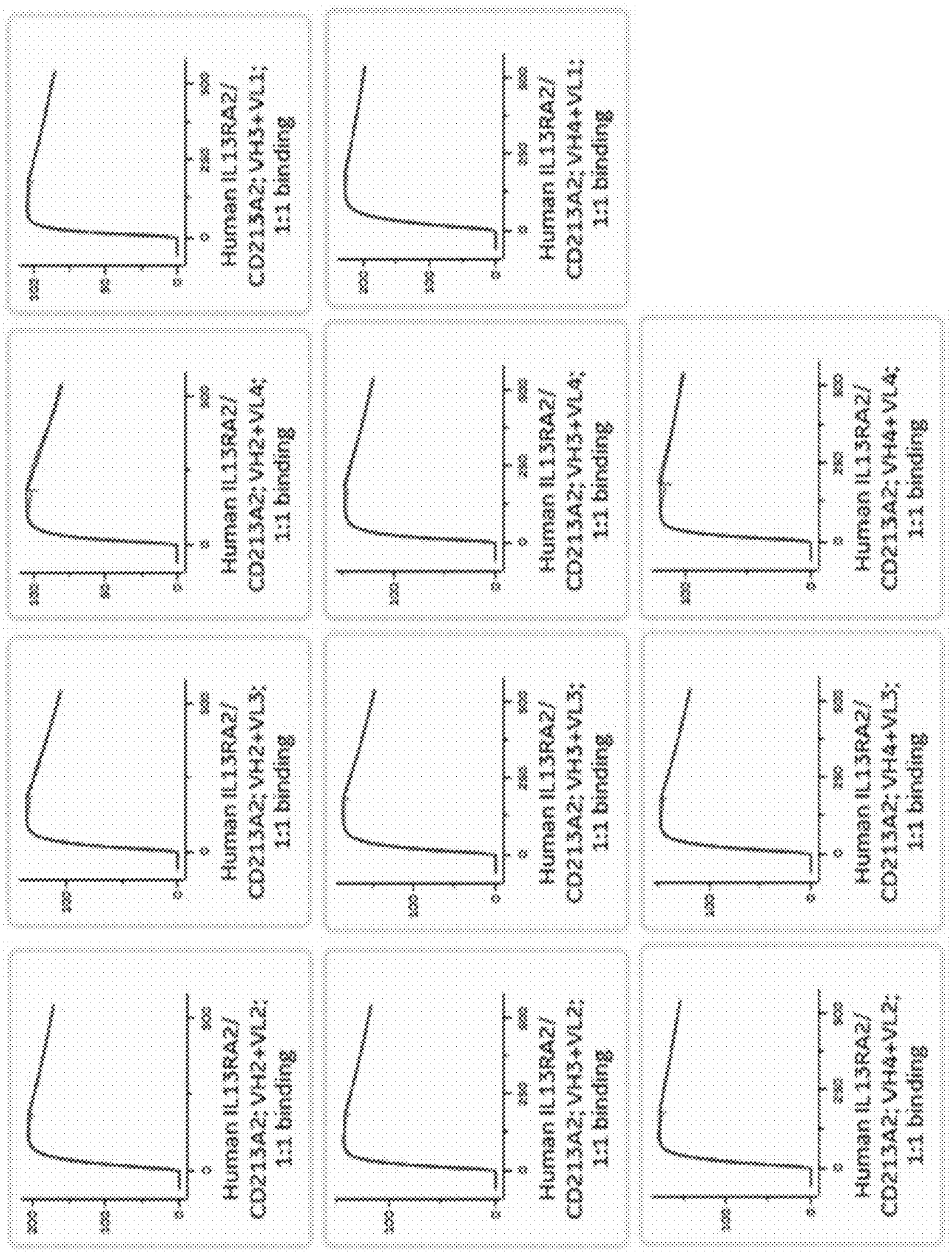

The affinity of human IL13Rα2 binding to humanized antibodies supernatant is summarized in Table 2 and the sensor-grams are shown in FIG. 3.

TABLE 2

The affinity and kinetics of human IL13Rα2 binding to humanized antibodies.

| Ligand | Analyte | $k_a$ (1/Ms) | $k_d$ (1/s) | $K_D$ (M) | Rmax (RU) | $Chi^2(RU^2)$ |
|---|---|---|---|---|---|---|
| NC | Human IL13Rα2 | NA | NA | NA | NA | NA |
| buffer | Human IL13Rα2 | NA | NA | NA | NA | NA |
| chimeric | Human IL13Rα2 | 5.11E+05 | 5.44E−04 | 1.07E−09 | 96 | 3.01E+00 |
| VH1 + VL1 | Human IL13Rα2 | 4.29E+05 | 3.29E−04 | 7.68E−10 | 388.7 | 1.38E+00 |
| VH1 + VL2 | Human IL13Rα2 | 4.12E+05 | 3.12E−04 | 7.58E−10 | 402.2 | 1.06E+00 |

TABLE 2-continued

The affinity and kinetics of human IL13Rα2 binding to humanized antibodies.

| Ligand | Analyte | $k_a$ (1/Ms) | $k_d$ (1/s) | $K_D$ (M) | Rmax (RU) | $Chi^2(RU^2)$ |
|---|---|---|---|---|---|---|
| VH1 + VL3 | Human IL13Rα2 | 5.14E+05 | 4.63E−04 | 9.00E−10 | 275.8 | 9.21E−01 |
| VH1 + VL4 | Human IL13Rα2 | 4.49E+05 | 2.69E−04 | 5.99E−10 | 265.1 | 4.47E+00 |
| VH2 + VL1 | Human IL13Rα2 | 5.93E+05 | 4.17E−04 | 7.04E−10 | 134.8 | 1.03E+00 |
| VH2 + VL2 | Human IL13Rα2 | 6.48E+05 | 5.55E−04 | 8.57E−10 | 206.7 | 8.15E−01 |
| VH2 + VL3 | Human IL13Rα2 | 6.49E+05 | 7.61E−04 | 1.17E−09 | 137 | 1.07E+00 |
| VH2 + VL4 | Human IL13Rα2 | 5.55E+05 | 7.48E−04 | 1.35E−09 | 106.8 | 1.90E+00 |
| VH3 + VL1 | Human IL13Rα2 | 9.01E+05 | 5.95E−04 | 6.61E−10 | 104.7 | 3.10E−01 |
| VH3 + VL2 | Human IL13Rα2 | 8.52E+05 | 5.95E−04 | 6.98E−10 | 143.2 | 4.75E−01 |
| VH3 + VL3 | Human IL13Rα2 | 6.20E+05 | 7.02E−04 | 1.13E−09 | 189.9 | 7.11E−01 |
| VH3 + VL4 | Human IL13Rα2 | 6.25E+05 | 6.15E−04 | 9.84E−10 | 150.1 | 1.42E+00 |
| VH4 + VL1 | Human IL13Rα2 | 5.83E+05 | 4.24E−04 | 7.27E−10 | 229.1 | 1.04E+00 |
| VH4 + VL2 | Human IL13Rα2 | 7.46E+05 | 4.45E−04 | 5.97E−10 | 181.6 | 7.56E−01 |
| VH4 + VL3 | Human IL13Rα2 | 7.69E+05 | 6.75E−04 | 8.77E−10 | 149.3 | 6.47E−01 |
| VH4 + VL4 | Human IL13Rα2 | 8.44E+05 | 5.01E−04 | 5.94E−10 | 121 | 2.12E+00 |

Production of Humanized IgGs

Figure 4:
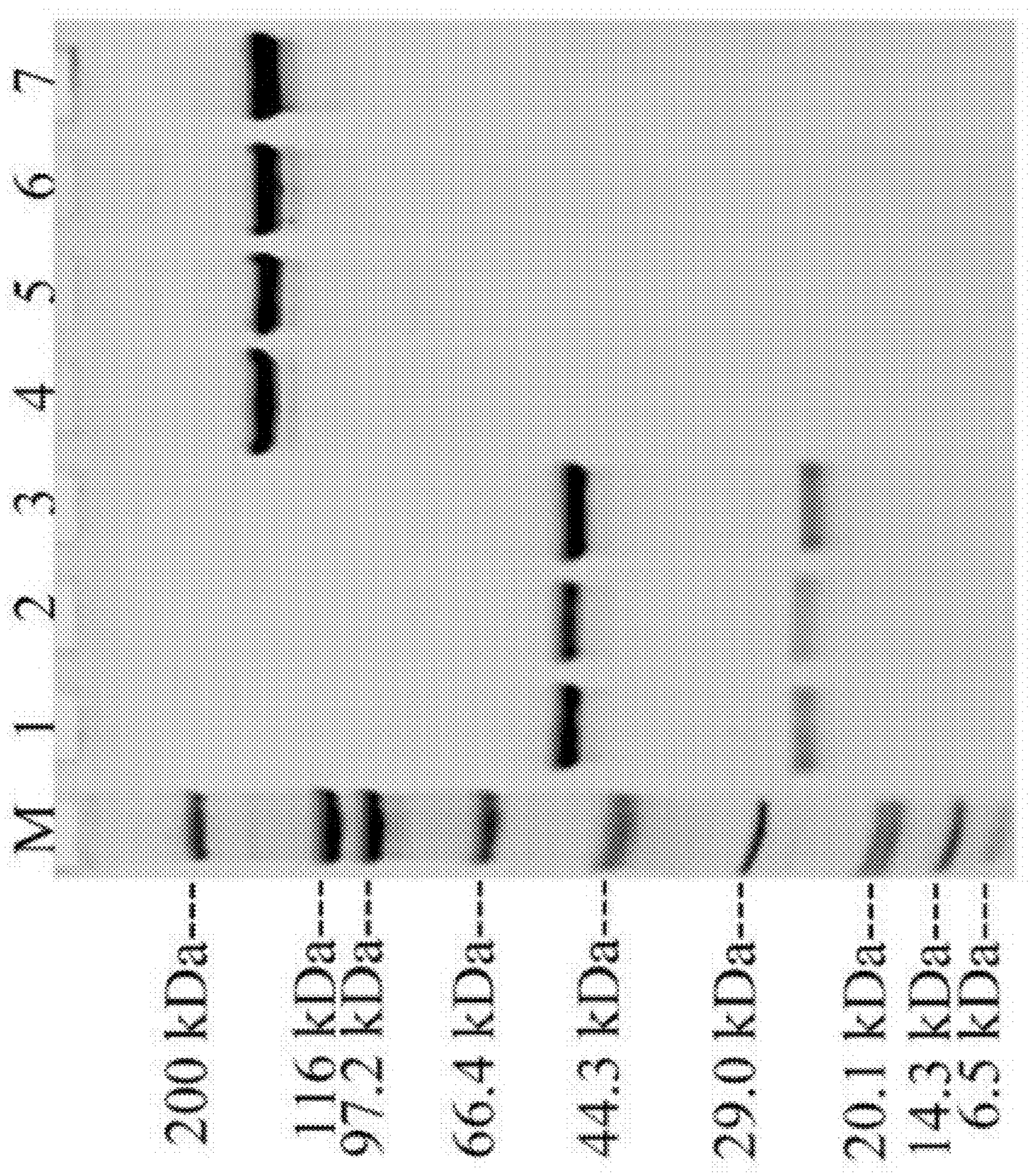
FIG. 4 shows the results of running three purified IgGs on SDS-PAGE under reducing and non-reducing conditions. Lane M: Protein marker. Lane 1: U3621EI120 VH2+VL3 under reducing conditions (Purity: 99%). Lane 2: U3621EI120 VH1+VL1 under reducing conditions (Purity: 99%). Lane 3: U3621EI120 VH1+VL4 under reducing conditions (Purity: 99%). Lane 4: U3621EI120 VH2+VL3 under non-reducing conditions (Purity: 98%). Lane 5: U3621EI120 VH1+VL1 under non-reducing conditions (Purity: 98%). Lane 6: U3621EI120 VH1+VL4 under non-reducing conditions (Purity: 97%). Lane 7: Human IgG.

The top three humanized antibodies with the highest affinity for human IL13Rα2 were expressed and purified according to GenScript's SOP. The purified IgGs migrated as ~150 kDa band in SDS-PAGE under non-reducing condition, ~50 kDa and ~25 kDa bands under reducing condition. Judging from the SDS-PAGE, the purity of humanized IgGs were all over 95% (FIG. 4).

Affinity Measurement of Purified hIgGs

Figure 5:
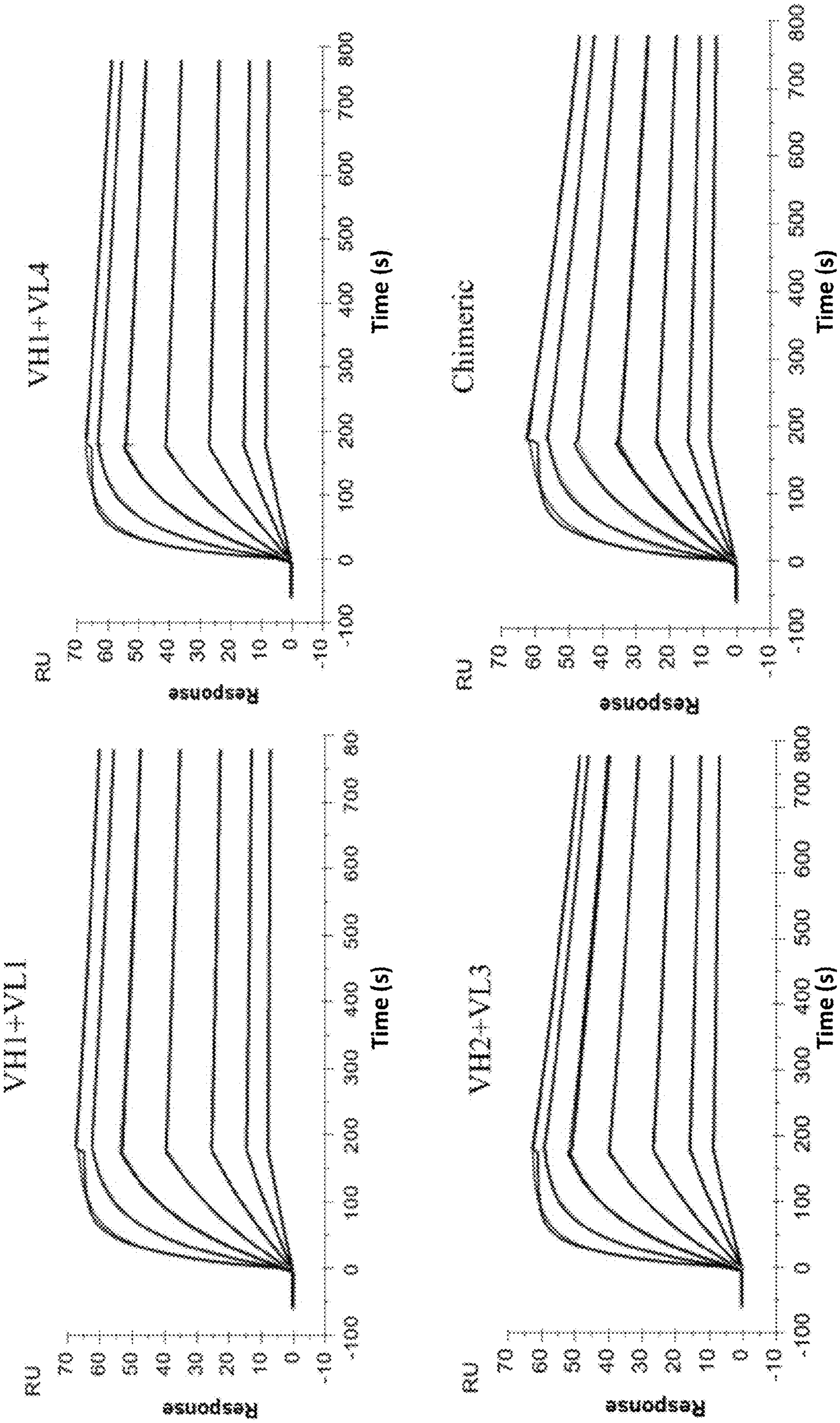
FIG. 5 shows sensor-grams of human IL13Rα2 binding to chimeric and selected humanized antibodies. Real-time responses are shown with colored curves. A fitting of Biacore experimental data to a 1:1 interaction model is shown in black. The antigen concentrations were 1.875, 3.75, 7.5, 15, 30, 60, 120 nM for chimeric antibody, and 0.9375, 1.875, 3.75, 7.5, 15, 30, 60 nM for other antibodies, respectively.

The affinity of human IL13Rα2 binding to antibodies is summarized in Table 3 and the sensor-grams are shown in FIG. 5.

TABLE 3

The affinity of human IL13Rα2 binding to selected humanization hIgGs.

| Ligand | Analyte | $k_a$ (1/Ms) | $k_d$ (1/s) | $K_D$ (M) | Rmax (RU) | $Chi^2(RU^2)$ |
|---|---|---|---|---|---|---|
| VH1 + VL1 | Human IL13Rα2 | 6.76E+05 | 1.91E−04 | 2.83E−10 | 67.57 | 0.0784 |
| VH1 + VL4 | Human IL13Rα2 | 7.41E+05 | 2.20E−04 | 2.97E−10 | 67.13 | 0.0821 |
| VH2 + VL3 | Human IL13Rα2 | 8.20E+05 | 4.20E−04 | 5.13E−10 | 62.6 | 0.0735 |
| Chimeric | Human IL13Rα2 | 3.30E+05 | 4.77E−04 | 1.45E−09 | 62.68 | 0.169 |

Summary:

Mouse monoclonal antibody (mAb) was successfully humanized. Four humanized heavy chains and four humanized light chains were designed, synthesized, and individually inserted into an expression vector. The humanized antibodies were expressed and used for affinity ranking test. Finally, three humanized antibodies with a similar binding affinity as the chimeric antibody were identified and purified.

Example 2: Affinity of Antibodies

In the following Example, the affinity of human IL13Rα2 binding to selected antibodies, including antibodies in which the $V_H$ region contained a D55E or G56A point mutation, was measured using Biacore T200 (GE Healthcare) using the parameters shown in Table 4.

TABLE 4

Binding parameters.

| Immobilization | |
|---|---|
| Capture time(s) | 25 |
| Flow rate(μl/min) | 10 |

TABLE 4-continued

Binding parameters.

| Association & Dissociation | |
|---|---|
| Association contact time(s) | 180 |
| Dissociation contact time(s) | 600 |
| Flow rate(μl/min) | 30 |
| Sample concentrations(nM) | 0.9375, 1.875, 3.75, 7.5, 15, 30, 60 |

TABLE 4-continued

Binding parameters.

| Surface regeneration | |
|---|---|
| Regeneration buffer | 10 mM Glycine-HCl |
| Contact time(s) | 30 |
| Flow rate(μl/min) | 30 |

Figure 6:
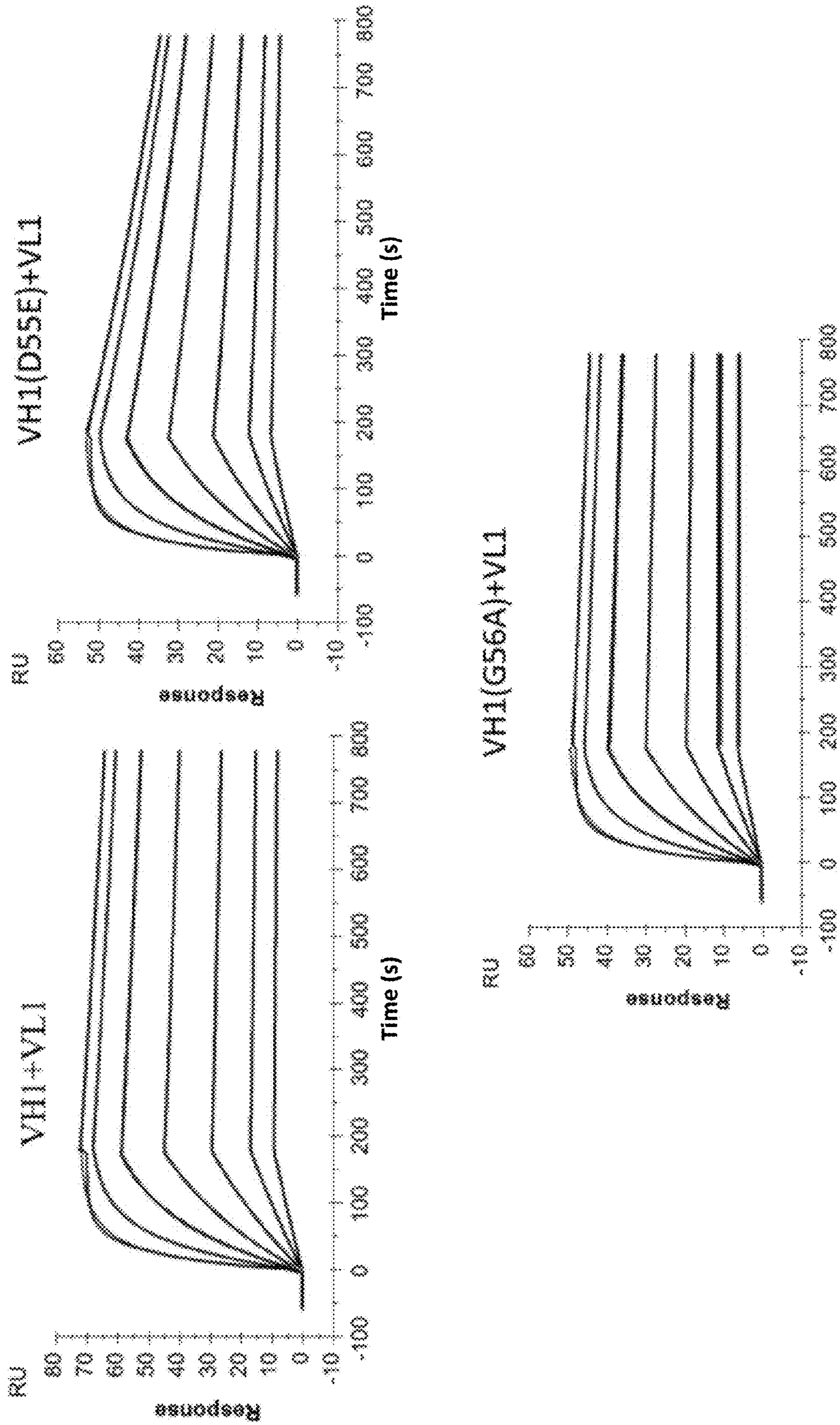
FIG. 6 shows sensor-grams of human IL13Rα2 binding to selected antibodies.

The affinity and kinetics of human IL13Rα2 binding to selected antibodies are summarized in Table 5, and the sensor-grams were shown in FIG. 6.

TABLE 5

The affinity and kinetics of L13Rα2 binding to selected ligands.

| Ligand | $k_a$ (1/Ms) | $k_d$ (1/s) | $K_D$ (M) | Rmax | $Chi^2$ $(RU^2)$ |
|---|---|---|---|---|---|
| VH1 + VL1 | 7.40E+05 | 1.90E−04 | 2.57E−10 | 72.19 | 0.0771 |
| VH1(D55E) + VL1 | 7.38E+05 | 7.12E−04 | 9.65E−10 | 53.44 | 0.0384 |
| VH1(G56A) + VL1 | 7.27E+05 | 1.56E−04 | 2.15E−10 | 48.67 | 0.043 |

Conclusions:

The D55E mutation reduced the affinity of the humanized anti-IL13Rα2 antibody, while the G56A did not. Nevertheless, the humanized anti-IL13Rα2 antibody VH1 (D55E)+VL1 still exceeded the affinity of the chimeric antibody (i.e, the murine VH and VL sequences with human constant region).

Example 3: Post-Translational Modifications Analysis

Figure 7:
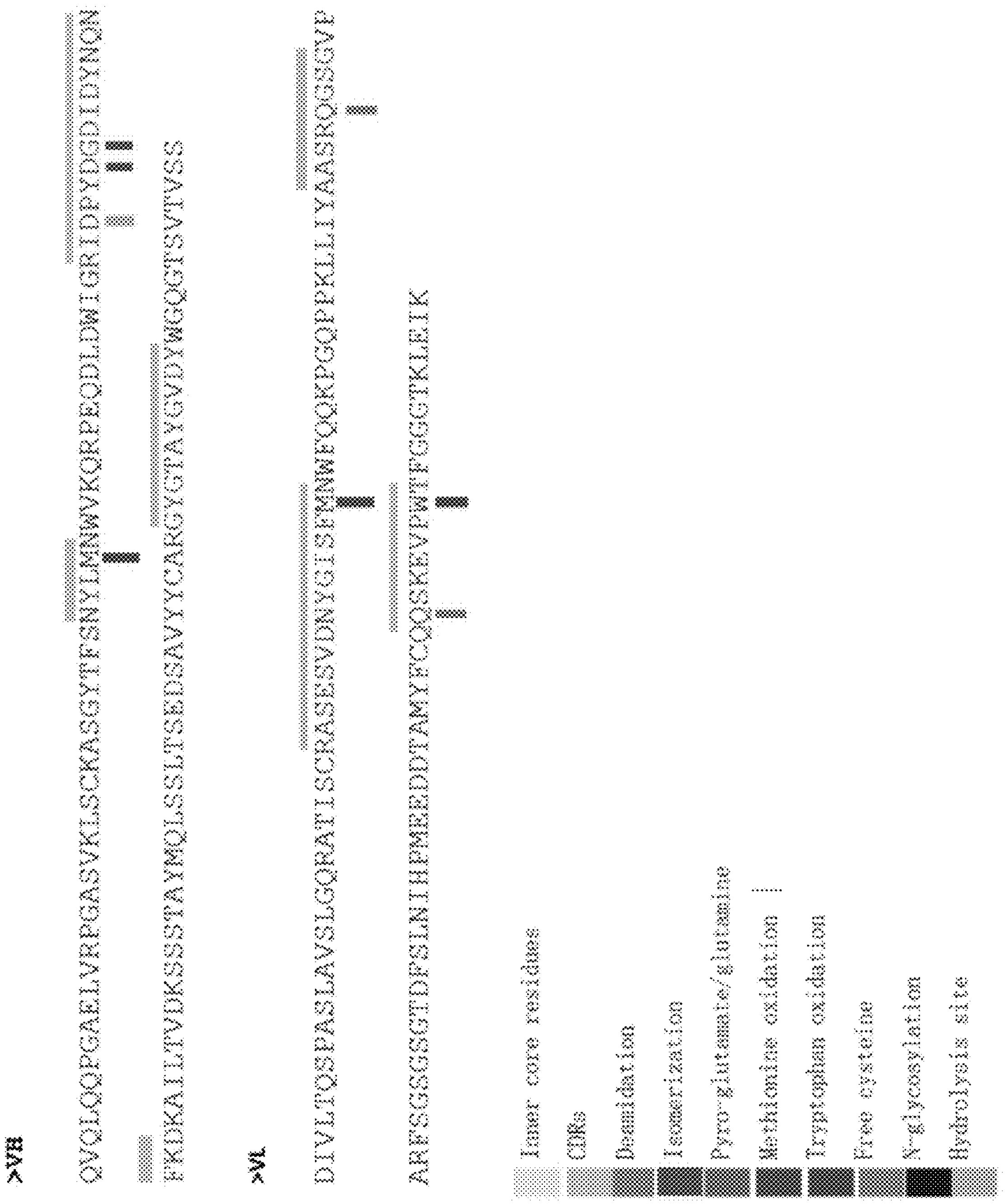
FIG. 7 shows the results of a post-translational modification analysis performed on the sequence of the original mouse monoclonal antibody (mAb). The amino acid resides with potential liabilities (e.g., potential for deamidation, isomerization, etc.; see key) within the heavy chain variable region ($V_H$; top; SEQ ID NO:25) and the light chain variable region ($V_L$; bottom; SEQ ID NO:26) of this antibody are indicated with a colored bar below. The complementarity-determining regions (CDRs) are indicated with a gray bar above.
Figure 8:
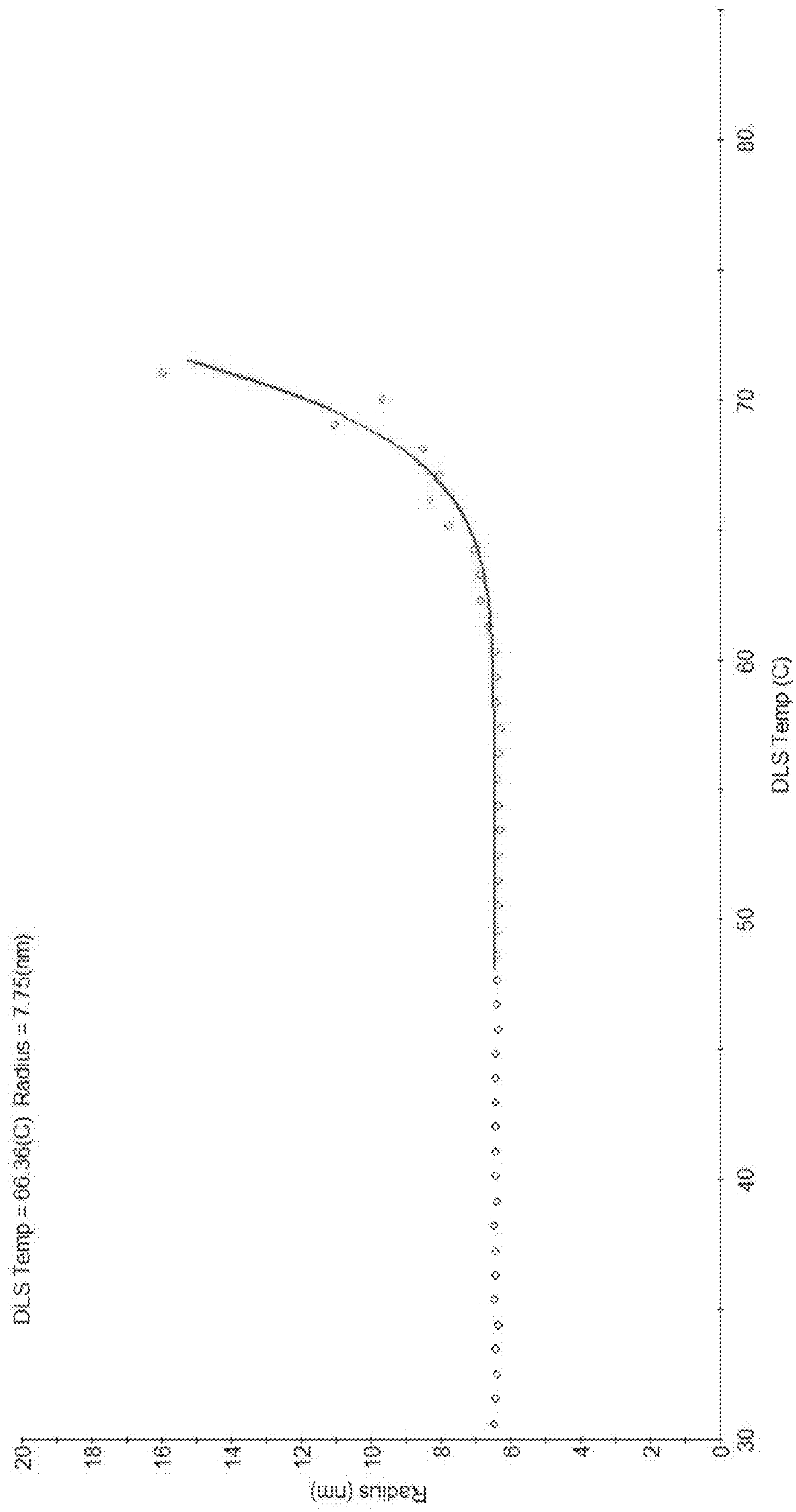
FIG. 8 shows the dynamic light scattering (DLS) graph of the chimeric antibody (Ab) at day 0 (D0).
Figure 9:
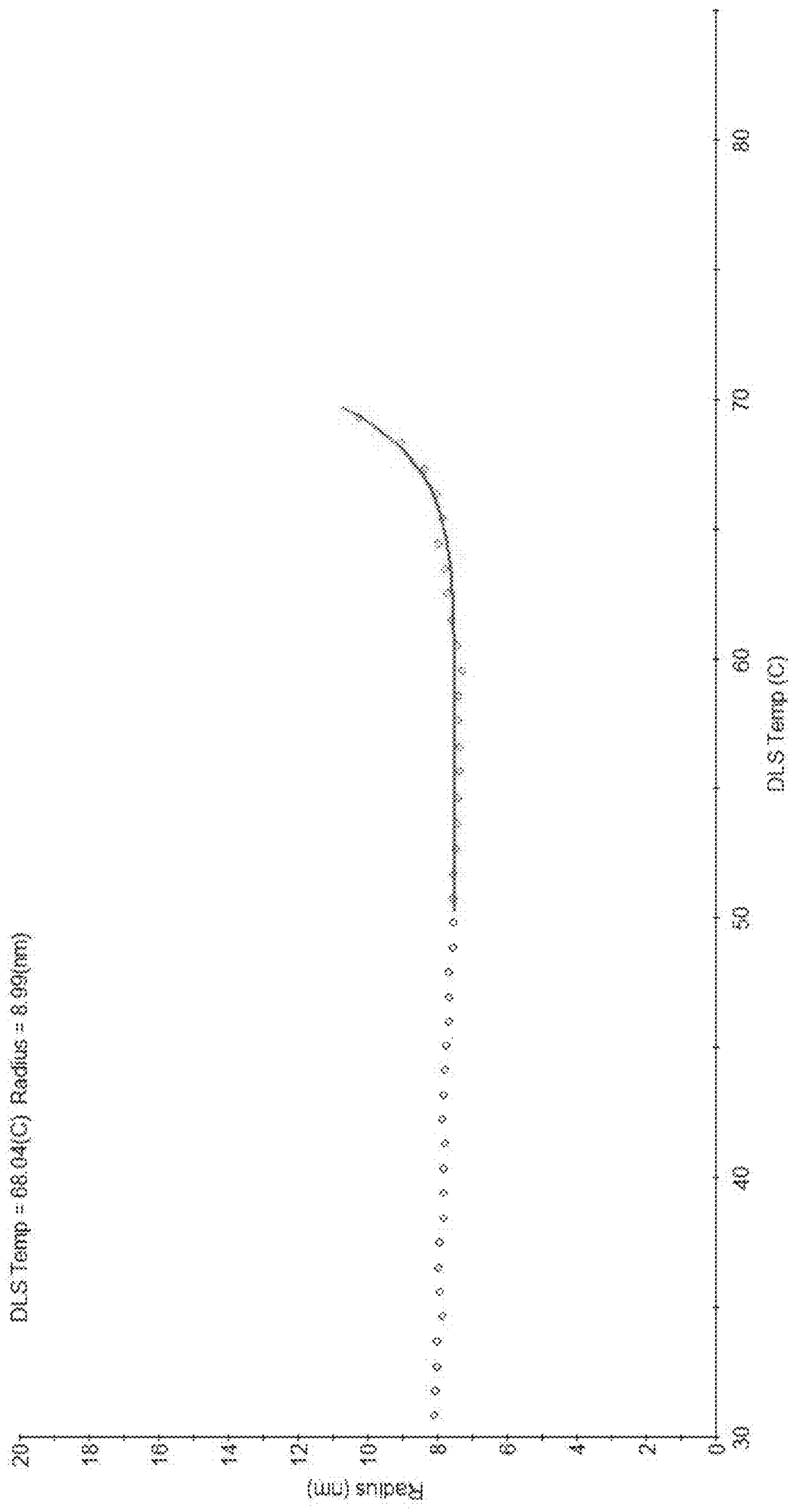
FIG. 9 shows the DLS graph of the fusion protein comprising the single-chain variable fragments (scFvs) connected by flexible linker (VH1-VL1) at D0.
Figure 10:
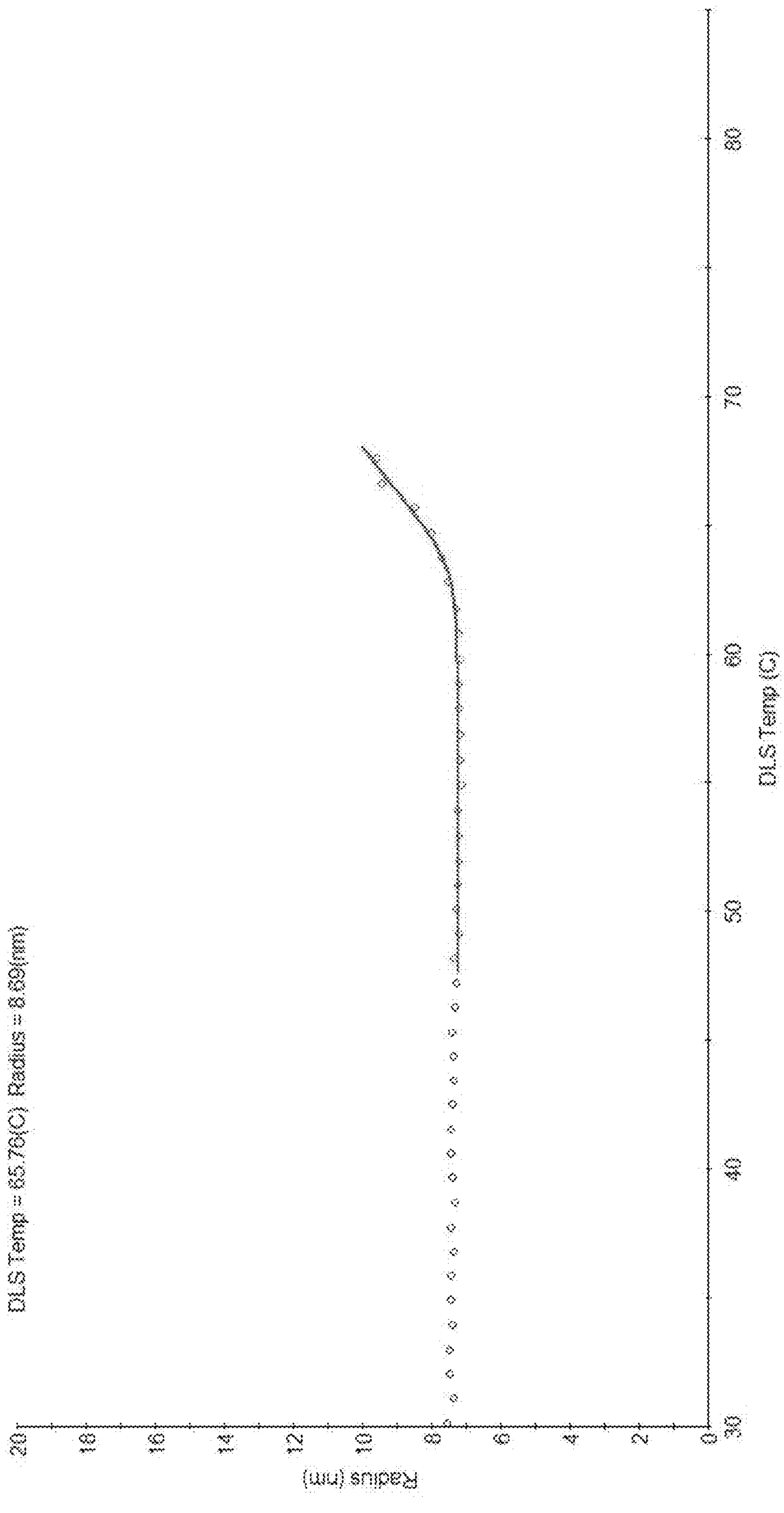
FIG. 10 shows the DLS graph of the D55E mutant scFv fusion protein (VH1D55E-VL1) at D0.
Figure 11:
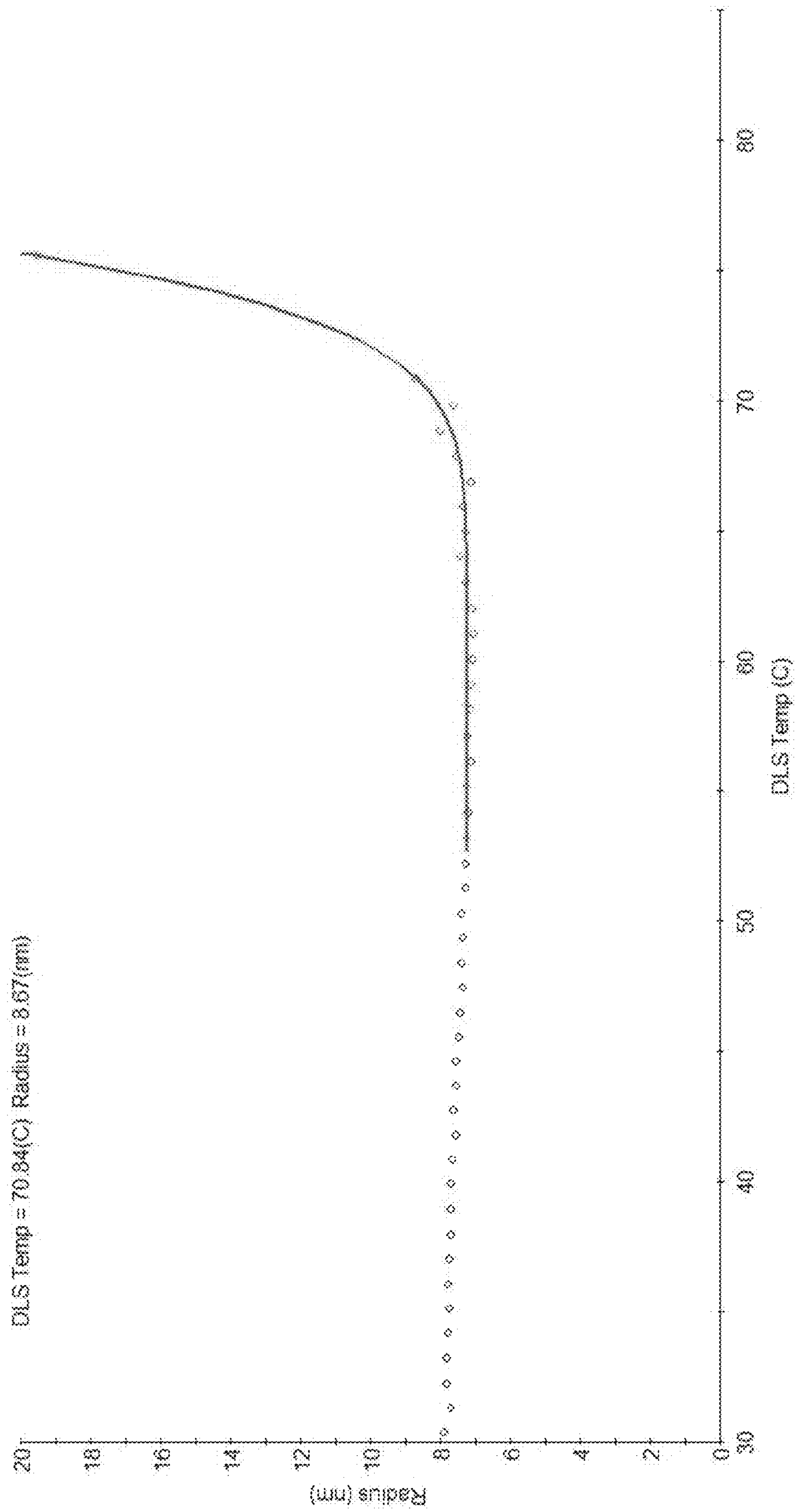
FIG. 11 shows the DLS graph of the G56A mutant scFv fusion protein (VH1G56A-VL1) at D0.
Figure 12:
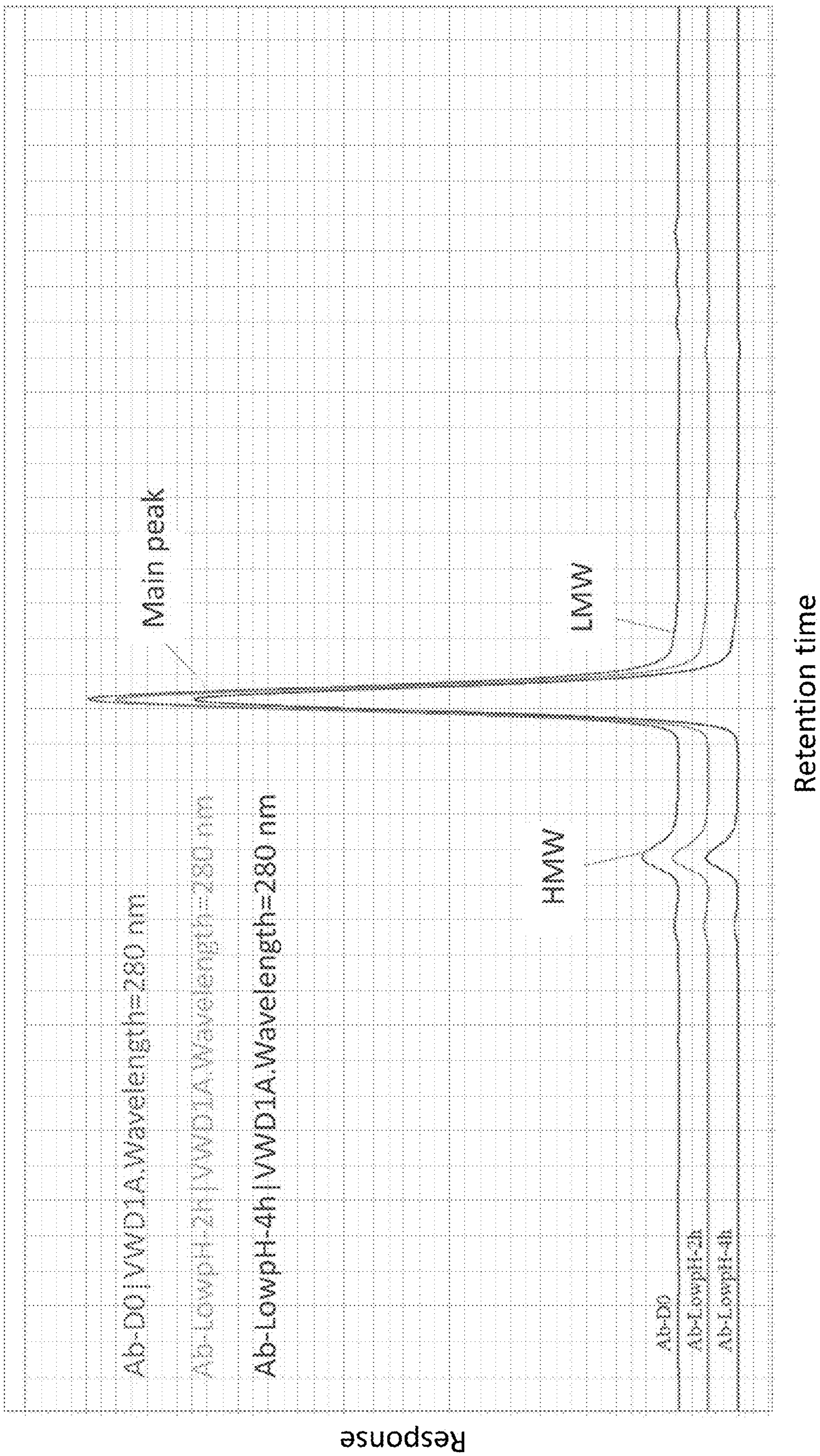
FIG. 12 shows the SEC-HPLC chromatograms at low pH 3.5 for Ab.
Figure 13:
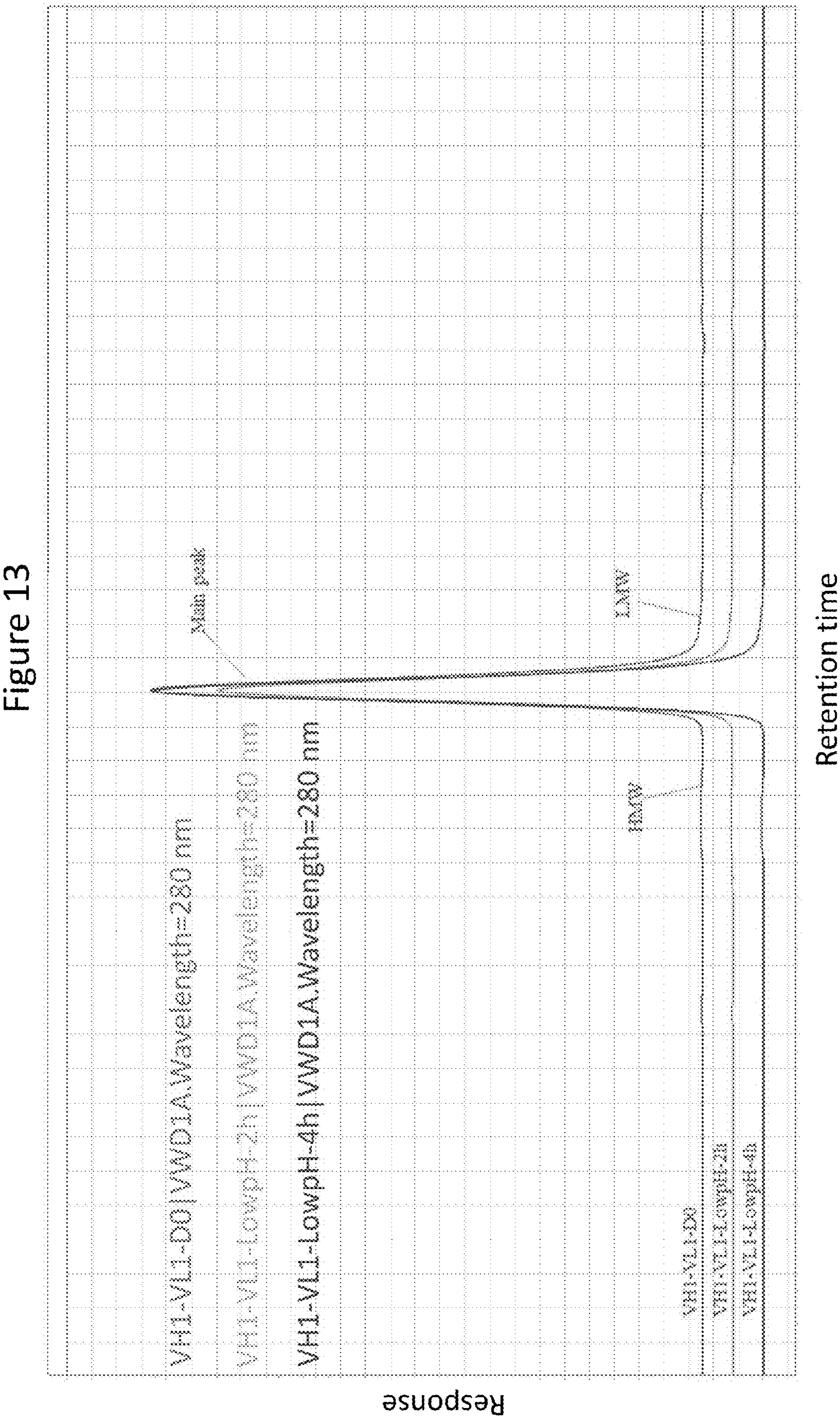
FIG. 13 shows the SEC-HPLC chromatograms at low pH 3.5 for VH1-VL1.
Figure 14:
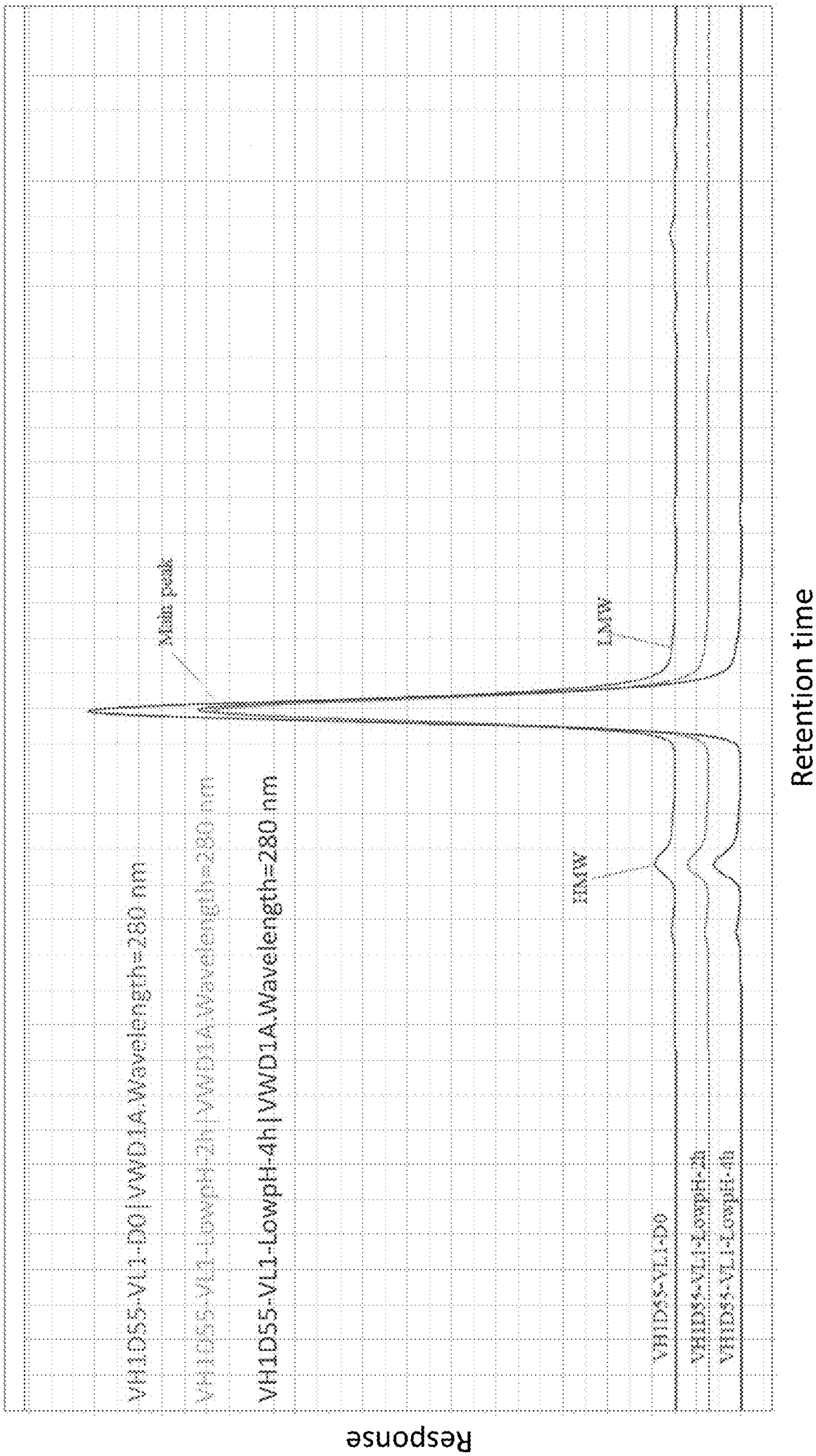
FIG. 14 shows the SEC-HPLC chromatograms at low pH 3.5 for VH1D55E-VL1.
Figure 15:
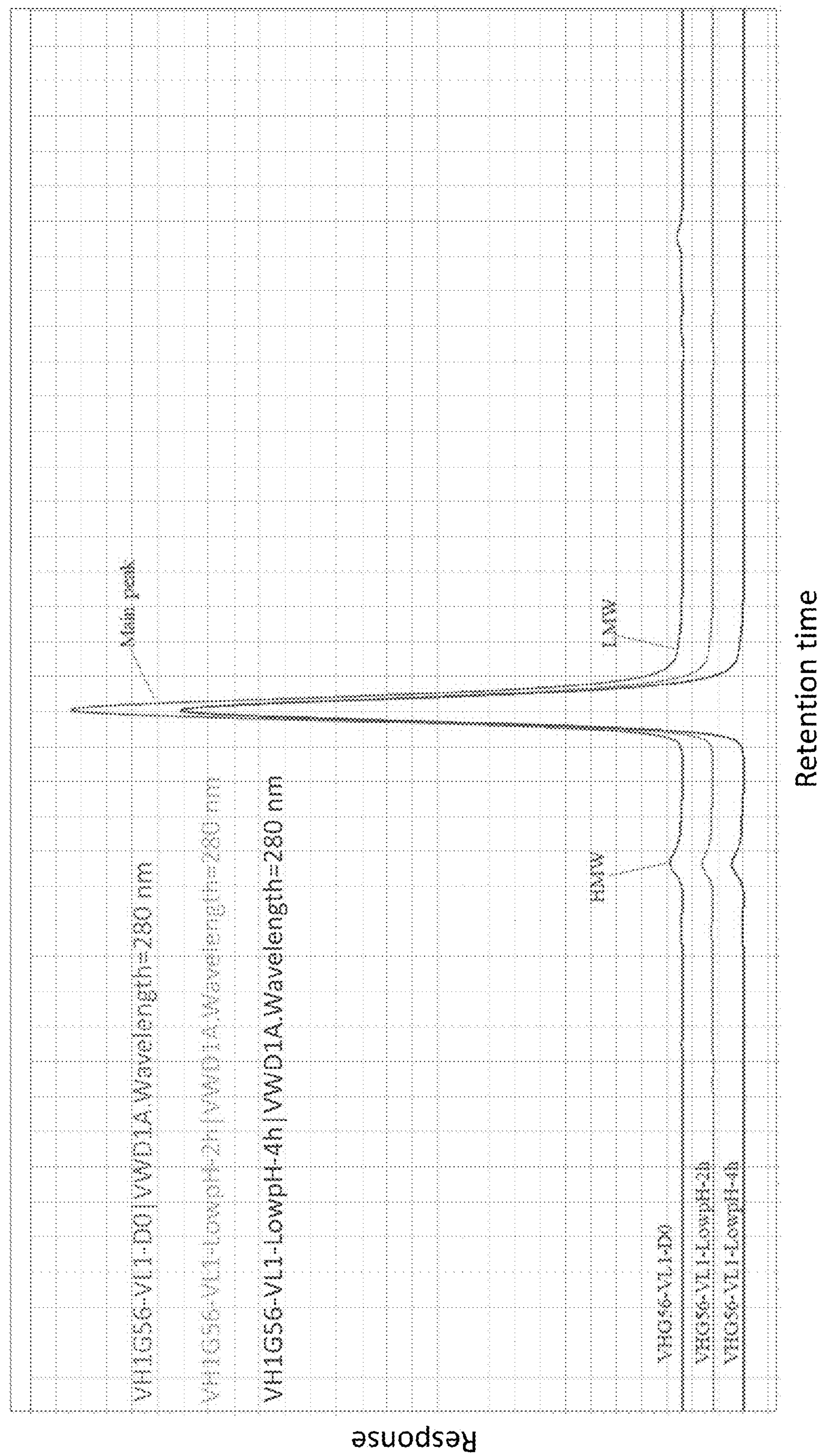
FIG. 15 shows the SEC-HPLC chromatograms at low pH 3.5 for VH1D56A-VL1.
Figure 16:
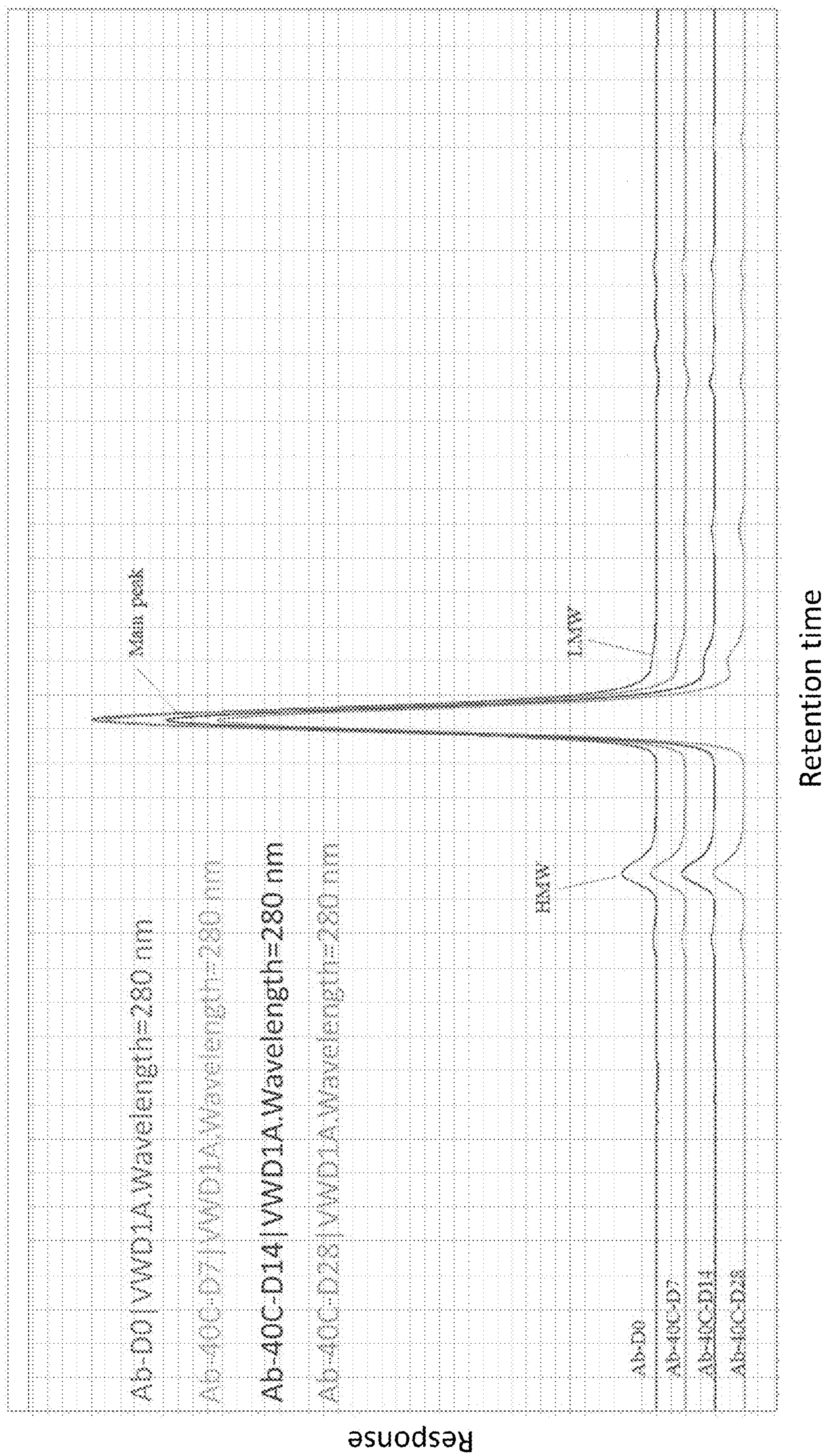
FIG. 16 shows the SEC-HPLC chromatogram at 40° C. for Ab.
Figure 17:
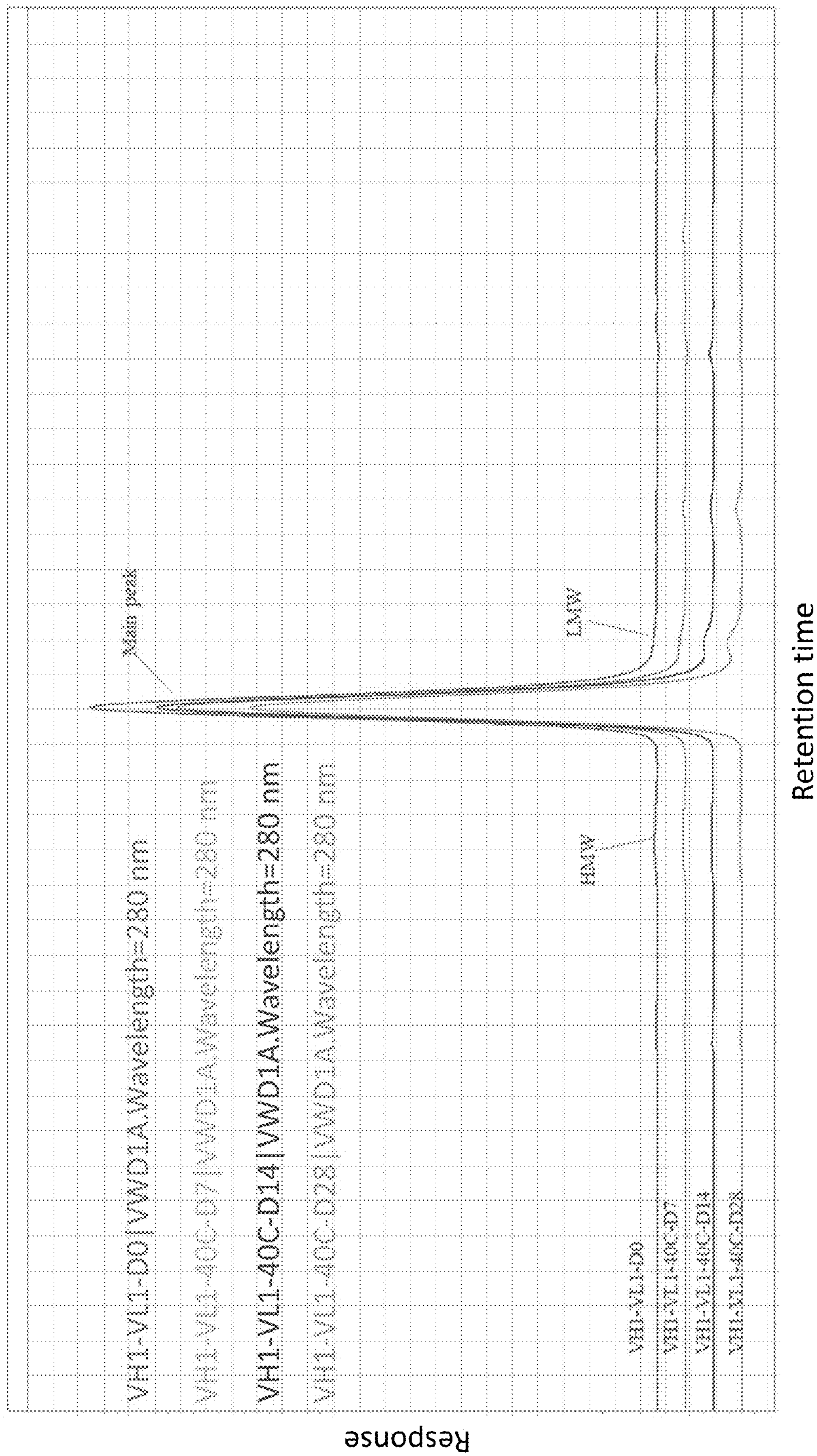
FIG. 17 shows the SEC-HPLC chromatogram at 40° C. for VH1-VL1.
Figure 18:
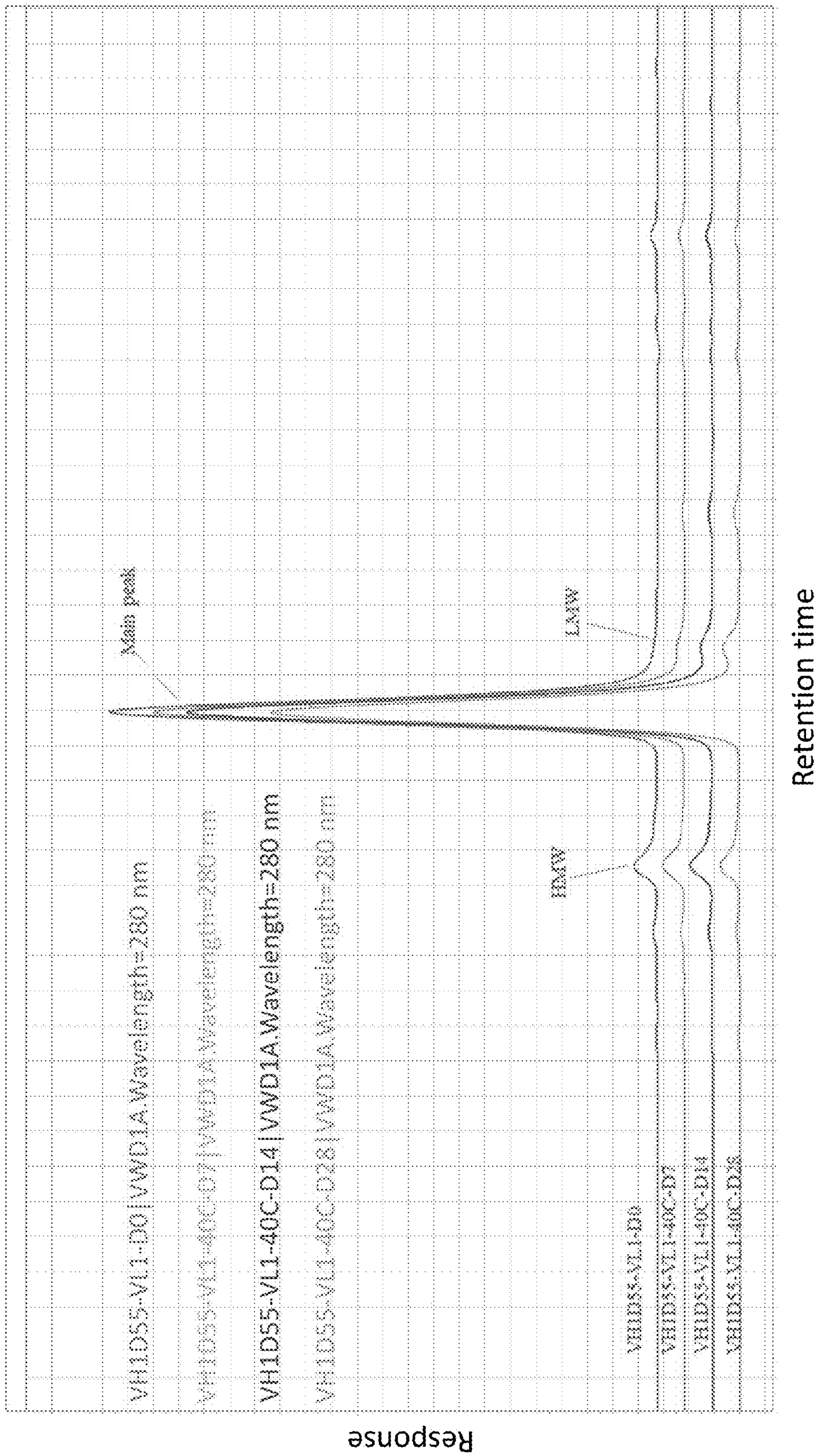
FIG. 18 shows the SEC-HPLC chromatogram at 40° C. for VH1D55E-VL1.
Figure 19:
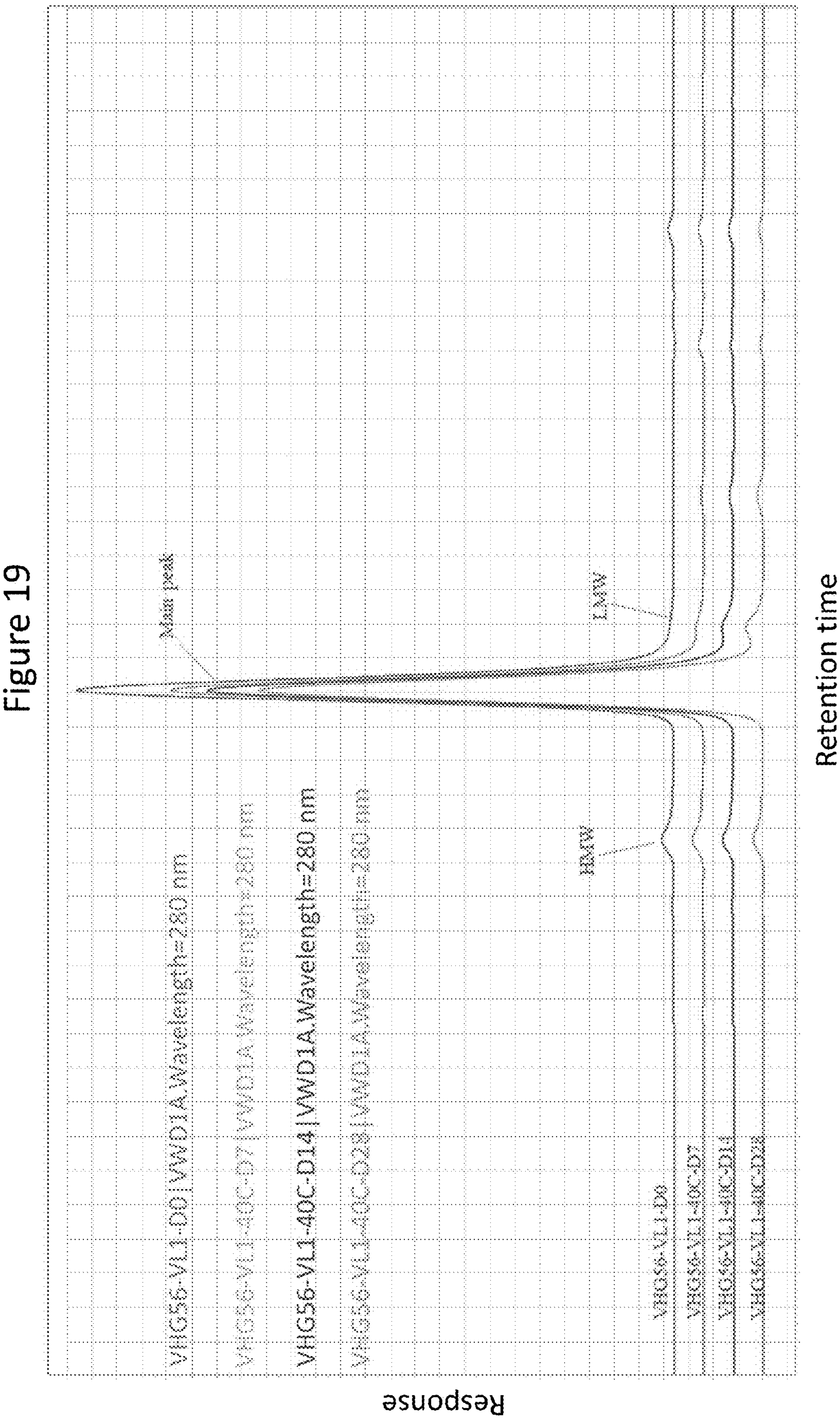
FIG. 19 shows the SEC-HPLC chromatogram at 40° C. for VH1D56A-VL1.

The grafted sequence was inspected for potential liability like N-glycosylation sites, post-translational modifications, and unpaired cysteine residues, which may affect the binding activity of the grafted antibody. Residues at risk for post-translational modification (PTM) are outlined in Table 6. The result of the PTM analysis performed on the mouse monoclonal antibody (mAb) sequence is shown in FIG. 7.

TABLE 6

Residues at risk for post-translational modification.

| Post-translational modifications | Sequence or residues |
|---|---|
| N-glycosylation | Asn-x-Ser/Thr (where x is not Pro) |
| Aspartate isomerization to isoaspartate | Asp-Gly, Asp-Ser |
| Deamidation of asparagine and glutamine to isoaspartate and isoglutamate, respectively | Asn-Gly, Asn-Ser are most prominent; Gln-Gly, Gln-Ser |
| Methionine oxidation | Surface-exposed Met residues; particular issue if Met in CDRs |
| Tryptophan oxidation | Surface-exposed Trp residues; particular issue if Trp in CDRs |
| Pyroglutamate formation from N-terminal glutamate or glutamine | N-terminal Glu or Gln residue |
| Free -thiol group | No pairing cysteine residue |
| Hydrolysis | Asp-Pro |

Example 4: Stability of Antibodies

In the following example, the inventor analyzed the stability of several forms of a humanized anti-IL13Rα2 antibody described herein. These forms include a mutant that comprises a D55E mutation in VH domain ("VH1D55E-VL1"), a mutant that comprises a G56A mutation in VH domain ("VH1G56A-VL1"), and the un-mutated form of the humanized anti-IL13Rα2 antibody ("VH1-VL1"). The stability of these humanized antibodies is compared to that of the parental chimeric murine antibody ("Ab"; the VH and VL of murine Ab clone 47 in human constant regions). All antibodies comprised the same constant regions.

Materials:

TABLE 7

Sample information.

| Antibody name | Amount & volume | Concentration | Buffer component and pH | Isoelectric point | Theoretical extinction coefficient |
|---|---|---|---|---|---|
| Chimeric Ab | 26 mg, 12 mL | 2.1 mg/mL | PBS, pH 7.4 | 6.91 | 1.433 |
| Humanized VH1-VL1 | 31 mg, 10 mL | 3.1 mg/mL | PBS, pH 7.4 | 7.20 | 1.475 |
| Humanized VH1D55E-VL1 | 31 mg, 11 mL | 2.8 mg/mL | PBS, pH 7.4 | 7.20 | 1.475 |
| Humanized VHG56A-VL1 | 30 mg, 9.5 mL | 3.1 mg/mL | PBS, pH 7.4 | 7.20 | 1.475 |

Sample Handling. For conditions of low pH 3.5, the above samples went through the buffer exchange, and then the aliquots were made. For condition of 40° C., the aliquots were made directly without buffer exchange.

TABLE 8

Sample handling conditions.

| Conditions | Starting buffer | Investigation conditions | Time points (Test items) |
|---|---|---|---|
| D 0 | PBS, pH 7.4 | D 0 | A, B, C |
| Low pH 3.5 | PBS, pH 7.4 | Low pH 2 h, 4 h | B, C |
| 40° C. | PBS, pH 7.4 | D 7, D 14, D 28 | B, C |

A: DLS (Tagg/onset); B: UV280; C: SEC-HPLC;
D 0: Day 0; D 7: Day 7; D 14: Day 14; D 28: Day 28;

Results:

DLS. Dynamic light scattering (DLS) measures the Tonset/agg (onset temperature at which aggregates are first detected. The DLS results are presented in Table 9, and the corresponding thermograms are presented in FIG. 8-11. As seen in Table 9, all humanized antibodies made surprisingly had increased stability over the murine chimeric antibody ("Ab"). However, the G56A mutation increased the stability and melting temperature the most.

TABLE 9

DLS test results.

| Sample name | Tonset/agg |
|---|---|
| Ab-D 0 | 66.36° C. |
| VH1-VL1-D 0 | 68.04° C. |
| VH1D55E-VL1-D 0 | 65.76° C. |
| VHG56A-VL1-D 0 | 70.84° C. |

UV280. The humanized antibodies are stable and do not result in protein loss, even when incubated at high temperature or low pH for extended periods of time as determined by UV280. The UV280 results are presented in Table 10.

TABLE 10

| UV280 test results. | | | | | | | |
|---|---|---|---|---|---|---|---|
| Sample name/ conditions | OD value | | | Average OD value | CV % | E | Conc. (mg/mL) |
| Ab-D0 | 0.54978 | 0.54869 | 0.54883 | 0.54910 | 0.088 | 1.449 | 1.14 |
| Ab-40C-D7 | 0.25935 | 0.25903 | 0.25856 | 0.25898 | 0.125 | 1.449 | 1.07 |
| Ab-40C-D14 | 0.27521 | 0.27538 | 0.27506 | 0.27522 | 0.047 | 1.449 | 1.14 |
| Ab-40C-D28 | 0.27557 | 0.27483 | 0.27497 | 0.27512 | 0.117 | 1.449 | 1.14 |
| Ab-LowpH-2h | 0.60794 | 0.60649 | 0.60664 | 0.60702 | 0.107 | 1.449 | 3.77 |
| Ab-LowpH-4h | 0.63343 | 0.63352 | 0.63272 | 0.63322 | 0.057 | 1.449 | 3.50 |
| VH1-VL1-D0 | 0.31577 | 0.31561 | 0.31475 | 0.31538 | 0.142 | 1.461 | 1.94 |
| VH1-VL1-40C-D7 | 0.32780 | 0.32722 | 0.32704 | 0.32735 | 0.099 | 1.461 | 2.02 |
| VH1-VL1-40C-D14 | 0.31151 | 0.30987 | 0.31156 | 0.31098 | 0.252 | 1.461 | 1.92 |
| VH1-VL1-40C-D28 | 0.33300 | 0.33297 | 0.33279 | 0.33292 | 0.028 | 1.461 | 2.05 |
| VH1-VL1-LowpH-2h | 0.47977 | 0.48082 | 0.47969 | 0.48009 | 0.107 | 1.461 | 10.19 |
| VH1-VL1-LowpH-4h | 0.51217 | 0.50994 | 0.51015 | 0.51075 | 0.197 | 1.461 | 8.39 |
| VH1D55E-VL1-D0 | 0.32923 | 0.32900 | 0.32813 | 0.32879 | 0.144 | 1.461 | 1.80 |
| VHID55E-VL1-40C-D7 | 0.33728 | 0.33636 | 0.33659 | 0.33674 | 0.116 | 1.461 | 1.84 |
| VHID55E-VL1-40C-D14 | 0.32553 | 0.32506 | 0.32465 | 0.32508 | 0.111 | 1.461 | 1.78 |
| VHID55E-VL1-40C-D28 | 0.34463 | 0.34495 | 0.34321 | 0.34426 | 0.220 | 1.461 | 1.89 |
| VH1D55E-VL1-LowpH-2h | 0.47308 | 0.47094 | 0.47071 | 0.47158 | 0.226 | 1.461 | 10.97 |
| VH1D55E-VL1-LowpH-4h | 0.48076 | 0.48201 | 0.48118 | 0.48132 | 0.108 | 1.461 | 9.88 |
| VHG56A-VL1-D0 | 0.29295 | 0.29304 | 0.29348 | 0.29316 | 0.079 | 1.461 | 1.81 |
| VHG56A-VL1-40C-D7 | 0.31669 | 0.31506 | 0.31507 | 0.31561 | 0.243 | 1.461 | 1.94 |
| VHG56A-VL1-40C-D14 | 0.30588 | 0.30512 | 0.30516 | 0.30539 | 0.114 | 1.461 | 1.88 |
| VHG56A-VL1-40C-D28 | 0.31476 | 0.31519 | 0.31535 | 0.31510 | 0.079 | 1.461 | 1.94 |
| VHG56A-VL1-LowpH-2h | 0.46417 | 0.46515 | 0.4657 | 0.46501 | 0.136 | 1.461 | 6.68 |
| VHG56A-VL1-LowpH-4h | 0.48869 | 0.48798 | 0.49163 | 0.48943 | 0.323 | 1.461 | 7.04 |

Note:
VHG56A-VL1-40C-D7 indicates that VHG56A-VL1 treated at 40° C. for 7 days; VHG56A-VL1-LowpH-4h indicates VHG56A-VL1 treated under low pH conditions for 4 hours; the same principle is made for othersample names.

pH 3.5 stability of SEC-HPLC measurement. The pH 3.5 stability of size-exclusion chromatography (SEC)-HPLC measurement is summarized in the following table, where samples of D0 is served as starting point, respectively. The humanized antibodies had high purity determined by SEC-HPLC for each molecule. The pH 3.5 stability of SEC-HPLC measurements are presented in Table 11, and the corresponding SEC-HPLC chromatograms are presented in FIG. 12-15.

TABLE 11

| pH 3.5 stability of SEC-HPLC test results. | | | | | |
|---|---|---|---|---|---|
| Sample name | Conditions | HMW (%) | Main peak (%) | LMW (%) | RT(min) |
| Ab | D 0 | 6.77 | 92.33 | 0.91 | 12.628 |
| | LowpH-2 h | 6.51 | 91.95 | 1.54 | 12.622 |
| | LowpH-4 h | 6.28 | 92.46 | 1.26 | 12.622 |
| VH1-VL1 | D 0 | 1.26 | 98.56 | 0.18 | 12.525 |
| | LowpH-2 h | 0.90 | 98.97 | 0.13 | 12.528 |
| | LowpH-4 h | 0.91 | 98.97 | 0.12 | 12.520 |
| VH1D55E-VL1 | D 0 | 6.07 | 93.84 | 0.09 | 12.467 |
| | LowpH-2 h | 5.42 | 94.47 | 0.11 | 12.457 |
| | LowpH-4 h | 5.44 | 94.46 | 0.09 | 12.451 |
| VHG56A-VL1 | D 0 | 2.91 | 96.83 | 0.27 | 12.518 |
| | LowpH-2 h | 2.69 | 97.18 | 0.13 | 12.513 |
| | LowpH-4 h | 2.78 | 97.13 | 0.10 | 12.508 |

40° C. stability of SEC-HPLC measurement. The 40° C. stability of SEC-HPLC measurement is summarized in Table 12, and the corresponding SEC-HPLC chromatograms are presented in FIG. 16-19. Sample D0 serves as a starting reference point. Certain changes were observed in terms of purity determined by SEC-HPLC for each molecule. These changes follow a similar trend: the main peak percentage decreased, low molecular weight species (LMW) increased, and high molecular weight species (HMW) had no obvious change. No obvious difference in change rate was observed among the four molecules. All humanized antibodies had less low molecular weight products (i.e., had less degradation products), and had less high molecular weight products (i.e., less aggregation).

TABLE 12

| 40° C. stability of SEC-HPLC test results. 40° C. stability of SEC-HPLC test results | | | | | |
|---|---|---|---|---|---|
| Sample name | Conditions | HMW (%) | Main peak (%) | LMW (%) | RT(min) |
| Ab | D 0 | 6.77 | 92.33 | 0.91 | 12.628 |
| | 40 C.-D 7 | 6.78 | 91.50 | 1.72 | 12.624 |
| | 40 C.-D 14 | 6.66 | 91.15 | 2.20 | 12.620 |
| | 40 C.-D 28 | 6.72 | 89.19 | 4.09 | 12.616 |
| VH1-VL1 | D 0 | 1.26 | 98.56 | 0.18 | 12.525 |
| | 40 C.-D 7 | 1.38 | 97.22 | 1.41 | 12.527 |
| | 40 C.-D 14 | 1.37 | 96.23 | 2.41 | 12.525 |
| | 40 C.-D 28 | 1.44 | 94.28 | 4.29 | 12.521 |
| VH1D55E-VL1 | D 0 | 6.07 | 93.84 | 0.09 | 12.467 |
| | 40 C.-D 7 | 5.80 | 92.49 | 1.71 | 12.464 |
| | 40 C.-D 14 | 5.87 | 91.00 | 3.13 | 12.464 |
| | 40 C.-D 28 | 5.85 | 89.10 | 5.06 | 12.458 |
| VHG56A-VL1 | D 0 | 2.91 | 96.83 | 0.27 | 12.518 |
| | 40 C.-D 7 | 3.00 | 95.34 | 1.66 | 12.518 |
| | 40 C.-D 14 | 3.08 | 94.02 | 2.90 | 12.515 |
| | 40 C.-D 28 | 3.14 | 91.95 | 4.93 | 12.512 |

Conclusions:

Based on the DLS tests, the Tonset/agg of Ab, VH1-VL1, VH1D55E-VL1, and VHG56A-VL1 are 66.36° C., 68.04° C., 65.76° C., and 70.84° C., respectively. These results demonstrate that the both VH1-VL1 and VHG56A-VL1 have higher melting temperatures than the parental chimeric antibody ("Ab"; the VH and VL of murine Ab clone 47 in human constant regions).

Based on the initial purity (D0) determination by SEC-HPLC, the main peak percentage of VH1-VL1 is the highest, followed by VHG56A-VL1, then VH1D55E-VL1, and Ab is the lowest. Thus, all humanized antibodies had higher purity and less degradation products and aggregated products than the parental chimeric antibody.

Based on the low pH 3.5 stability test, no obvious changes in purity were observed for each molecule. Based on the 40° C. stability test, certain changes were observed in the purity of each molecule. These changes followed a similar trend: the main peak percentage decreased, LMW increased, and HMW had no obvious change. The results demonstrate that all four forms of the antibody are relatively stable at low pH and high temperature. VH1-VL1 and VH1G56A-VL1 showed less HMW (%) than the chimeric antibody (Ab) and humanized VH1D55E-VL1.

Example 5: Affinity of Antibodies

In the following Example, the inventor measured the binding affinity of two mutant forms of a humanized anti-IL13Ra2 antibody described herein to human IL13Ra2 using a Biacore T200. One of these mutants comprises a single W100F mutation in VL domain ("Ab Vh1-VL1W100F"). The second mutant comprises the same W100F mutation in VL domain as well as a G56A mutation in the VH domain ("Ab Vh1G56A-VL1W100F").

Materials:

TABLE 13

| Samples | | |
|---|---|---|
| Samples | MW(KDa) | Concentration(mg/ml) |
| Ab Vh1-VL1W100F | 150 | 0.706 |
| Ab Vh1G56A/VL1W100F | 150 | 0.734 |
| Human IL13Ra2 | 44.18 | 0.5 |

TABLE 14

| Instrument and reagents | | | |
|---|---|---|---|
| Names | Cat. No. | Lot. No. | Vendor |
| Biacore T200: GR18010468 | N/A | N/A | GE Healthcare |
| HBS-EP + buffer | BR-1006-69 | 31644 | GE Healthcare |
| Series S Sensor Chip Protein A | 29-1275-55 | 10299112 | GE Healthcare |

TABLE 14-continued

| Instrument and reagents | | | |
|---|---|---|---|
| Names | Cat. No. | Lot. No. | Vendor |
| Regeneration buffer: 10 mM Glycine-HCl pH 1.7 | BR-1003-54 | 01/05/2021 | Genscript |

Methods:

The assay was performed at 25° C. and the running buffer was HBS-EP+. Diluted antibodies were captured on the sensor chip through Fc capture method. Human IL13Ra2 was used as the analyte. Running buffer was injected as the dissociation phase. The running configuration is detailed in Table 15 below.

TABLE 15

| Running configuration | |
|---|---|
| Capture | |
| Ligand | antibodies |
| Capture time(s) | 15 |
| Association & Dissociation | |
| Association contact time(s) | 180 |
| Dissociation contact time(s) | 600 |
| Flow rate(μl/min) | 30 |
| Sample concentrations(nM) | 80, 40, 20, 10, 5, 2.5, 1.25, 0.625 |
| Surface regeneration | |
| Regeneration buffer | 10 mM Glycine-HCl |
| Contact time(s) | 30 |
| Flow rate(μl/min) | 30 |

Figure 20:
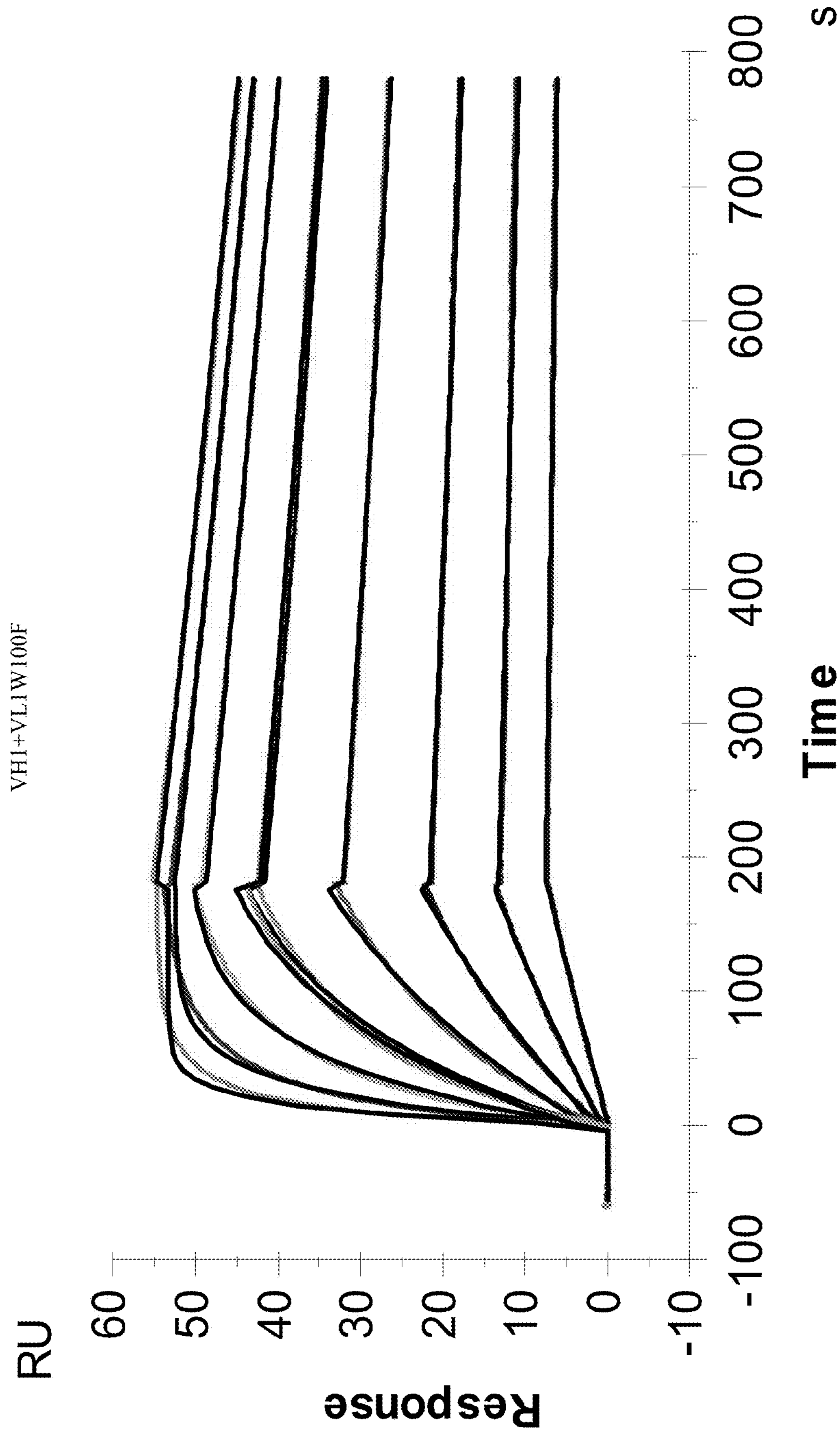
FIG. 20 shows the sensor-grams of antibodies to human IL13Rα2.
Figure 20:
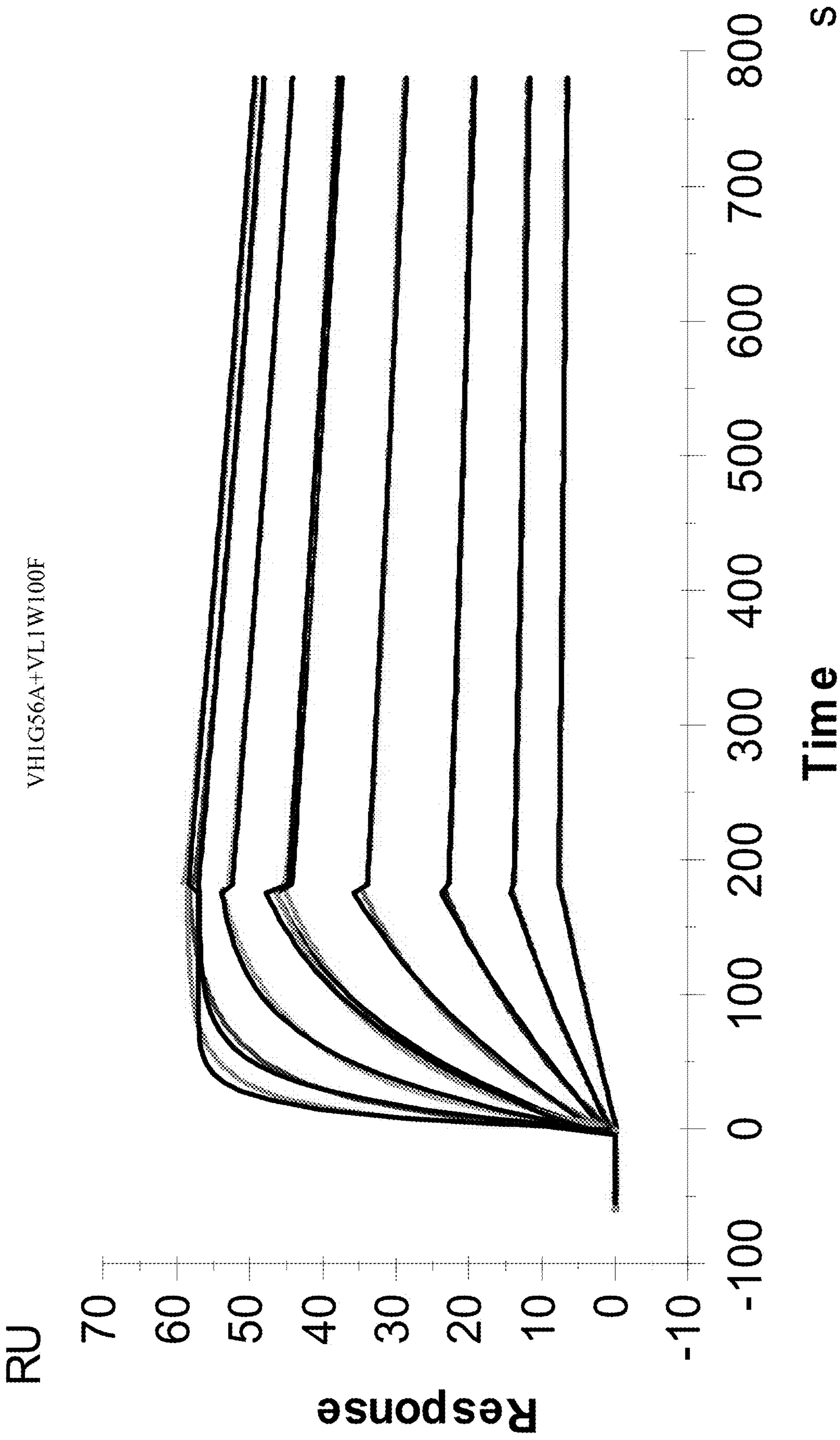

Results:

All the data were processed using the Biacore T200 Evaluation software version 3.1. Flow cell 1 and blank injection of buffer in each cycle were used as a double reference for response units subtraction. The binding kinetic data is shown in Table 16, and the binding sensor-grams are shown in FIG. 20.

TABLE 16

| Affinity ranking of antibodies to Human IL13Ra2 | | | | | | |
|---|---|---|---|---|---|---|
| Ligand | Analyte | ka (1/Ms) | kd (1/s) | KD (M) | Rmax (RU) | $Chi^2(RU^2)$ |
| Vh1G56A-VL1W100F | Human IL13Ra2 | 1.02E+06 | 2.84E−04 | 2.77E−10 | 58.66 | 0.207 |
| Vh1-VL1W100F | Human IL13Ra2 | 1.03E+06 | 3.34E−04 | 3.26E−10 | 55.02 | 0.169 |

Conclusions:

The affinity of the single and double mutant humanized antibodies have higher affinities than the parental humanized chimeric antibody and showed similar affinity to the humanized VH1-VL1 antibodies.

Example 6: Production of Antibody

In the following Example, the inventor assesses the binding affinity and production levels of several forms of a humanized anti-IL13Ra2 antibody described herein.

Antibodies were produced using the Expi293™ expression system (ThermoFisher) according to the manufacturer's protocol. Briefly, Expri293F TM cells were grown in Expri293F TM Expression medium in shaker flasks. Expri293F TM cells were seeded for transfection at $3\times10^6$ viable cells/ml. Plasmid DNA encoding the humanized antibodies was diluted in Opti-MEM TM I medium to achieve a final concentration of 1 μg/ml in cultured cells. ExpiFectamine TM 293 reagent was diluted in Opti-MEM TM I medium. In 5 minutes, diluted DNA was combined with diluted ExpiFectamine TM 293 reagent to form plasmid DNA/ExpiFectamine TM 293 complexes for 15 minutes. The complexes were then gently transferred to the cells, swirling the culture flask. The transfected cells were incubated in a 37° C. incubator with 8% CO2 and over 80% relative humidity on an orbital shaker. At 18-22 hours post-transfection, ExpiFectamine TM 293 transfection enhancer 1 and ExpiFectamine TM 293 transfection enhancer 2 were added to the transfection flask. The transfected cells were grown for 4-5 days until cells' viability decreased to approximately 50%. Cells were then collected and centrifuged at 400 g for 10 min. The supernatants containing antibodies were collected and filtered through 0.45 μm filters. All antibodies were purified using protein A-sepharose 4B TM (Invitrogen).

Figure 21:
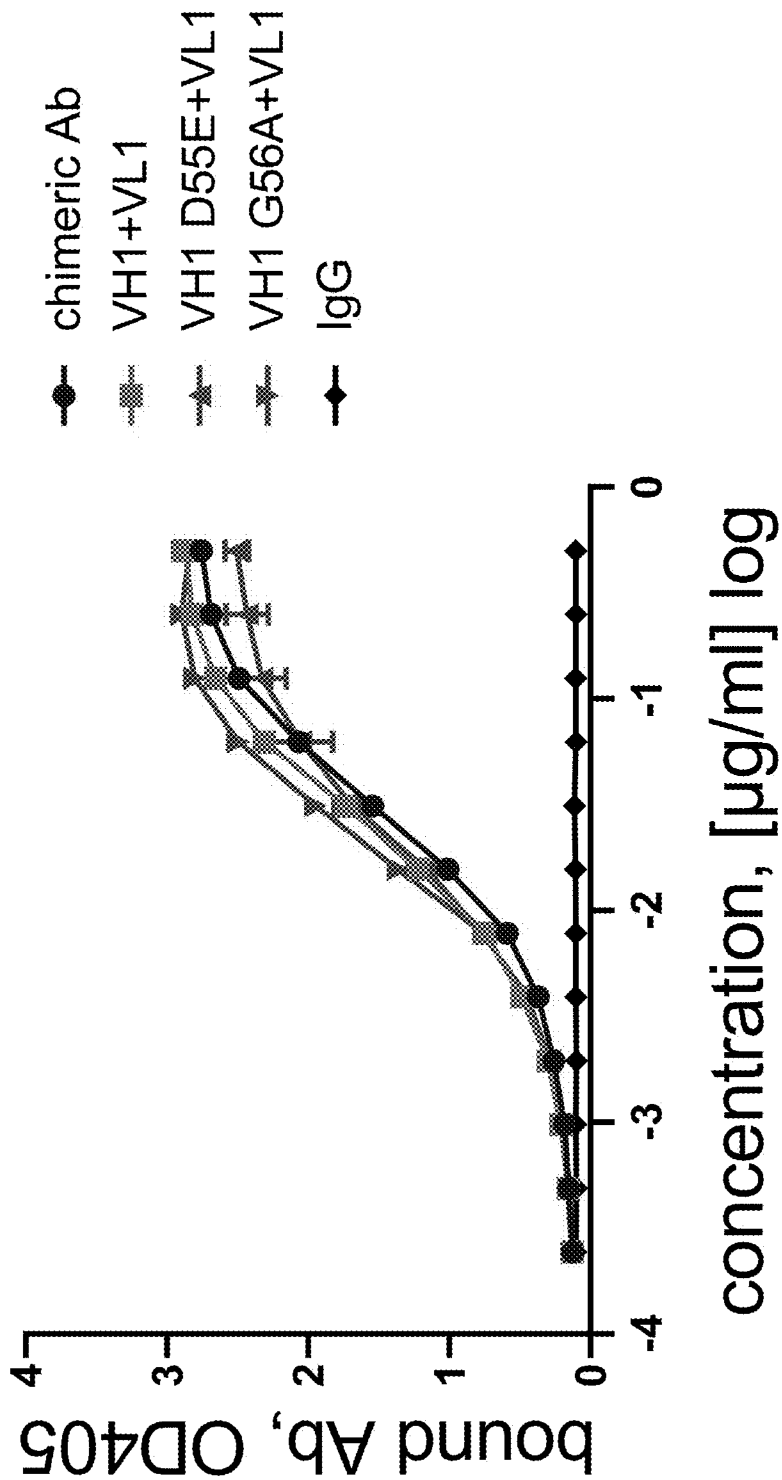
FIG. 21 shows binding of the chimeric murine antibody (Ab), humanized antibody (VH1-VL1) and variants of humanized antibody with mutations in the VH1 chain (D55E and G56A) to human recombinant IL13Rα2 in plate ELISA. N=3. Data are presented as mean f SEM.
Figure 22:
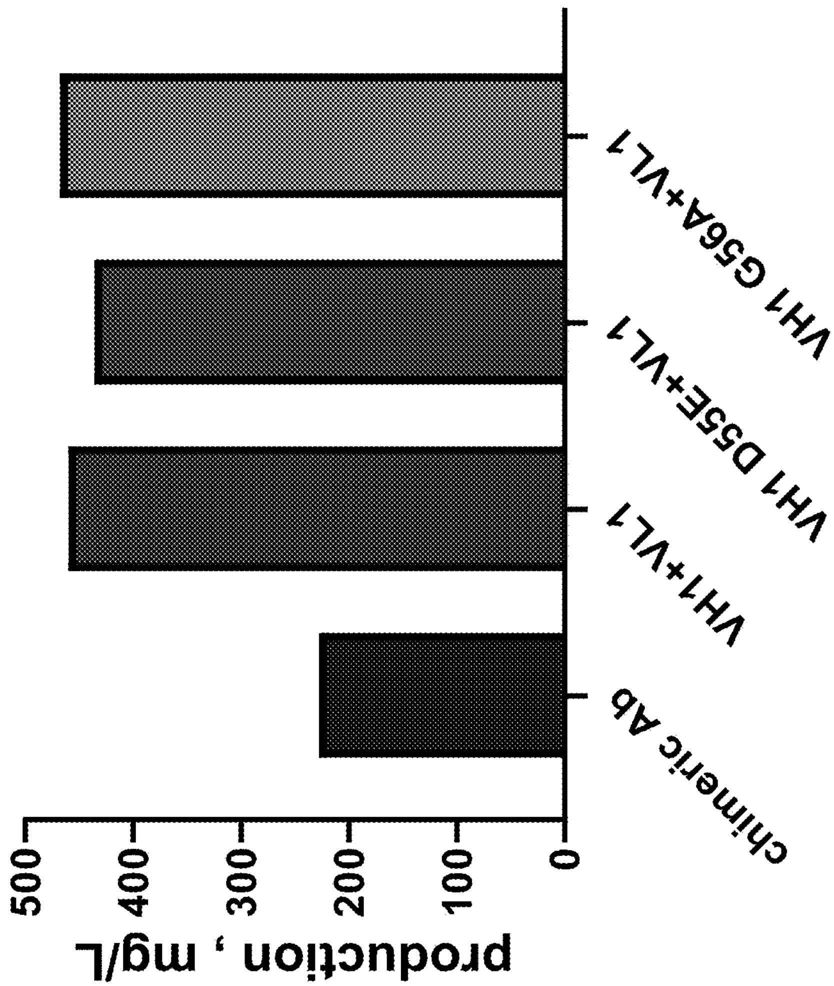
FIG. 22 shows a comparison of production of chimeric murine antibody (Ab), humanized antibody (VH1-VL1), and variants of humanized antibody with mutations in VH1 chain (D55E and G56A) in a single batch in the Expi293™ expression system.

The binding affinity of the chimeric murine antibody (Ab), humanized antibody (VH1-VL1) and variants of humanized antibody with mutations in the VH1 chain (D55E and G56A) to human recombinant IL13Rα2 was testing by plate ELISA. The results demonstrate that, while the D55E mutation affect the affinity of the antibody, the G56A mutation does not. Further, the results show that both the mutants and the non-mutant humanized antibody bind to IL13Rα2 with a greater affinity than the parental chimeric murine antibody (FIG. 21). Additionally, the production of these antibodies in a single batch was compared. The results demonstrate that all three humanized antibodies (i.e., the D55E mutant, the G56A mutant, and the non-mutated antibody) were produced at higher concentrations than the parental chimeric murine antibody (FIG. 22).

The affinity of additional humanized antibody variants with mutations in the VH1 chain (M34A, D52E) or VL1 chain (M37A, Q58E, Q94E, W100F) was measured. While several of these variants (i.e., VH1 M34A-VL1, VH1 MD52E-VL1, VH1-VL1 Q94E, and VH1-VL1 W100F) showed comparable affinity to the non-mutated humanized antibody (VH1-VL1), two of the tested mutilations (i.e., VH1-VL1 M37A and VH1-VL1 Q58E) drastically decreased binding affinity (FIG. 23) demonstrating that some changes within the humanized antibody drastically reduced the binding affinity of the humanized antibodies.

Figure 24:
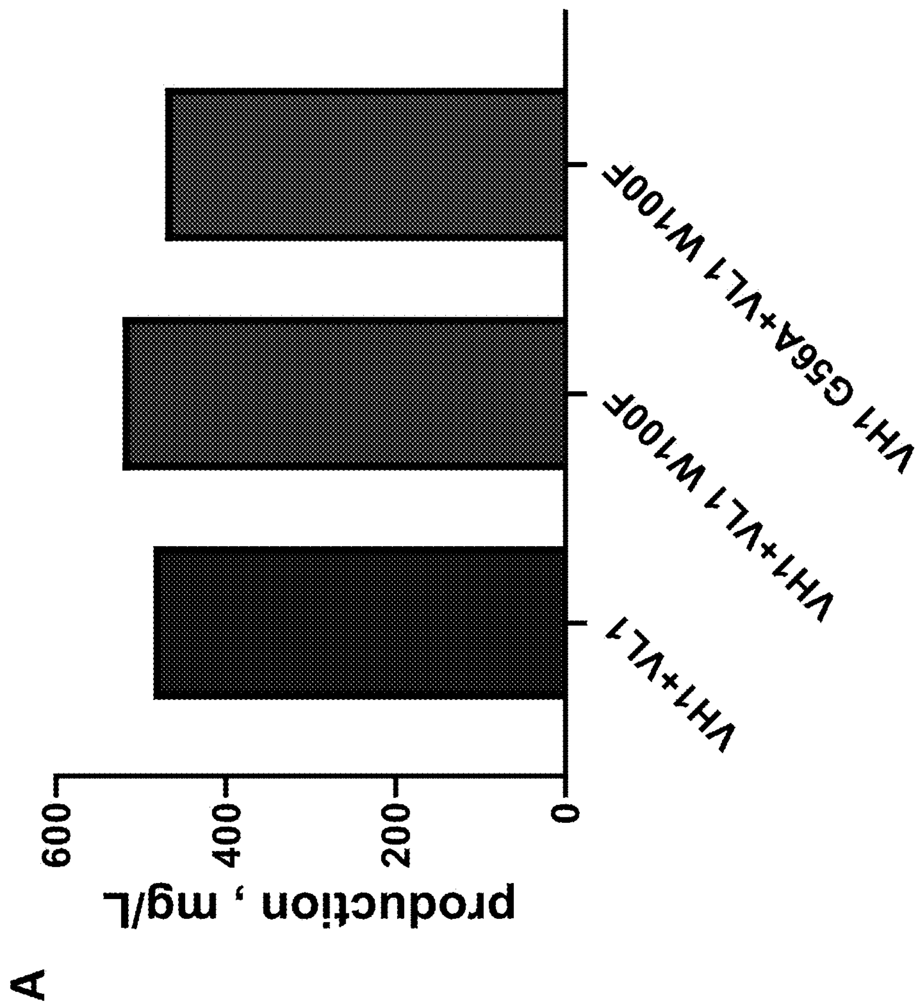
FIG. 24 shows the production and binding of two mutant versions of the humanized antibody, which comprise either a single mutation in VL1 chain (W100F) or a double mutation (VH1 G56A-VL1 W100F). (A) Comparison of production of a single batch of humanized antibody (VH1-VL1), and the W100F and VH1 G56A-VL1 W100F variants thereof in the Expi293™ expression system. (B) Binding of the mutant antibodies to human IL13Rα2 in plate ELISA. N=4. Data presented as mean±SEM.
Figure 24:
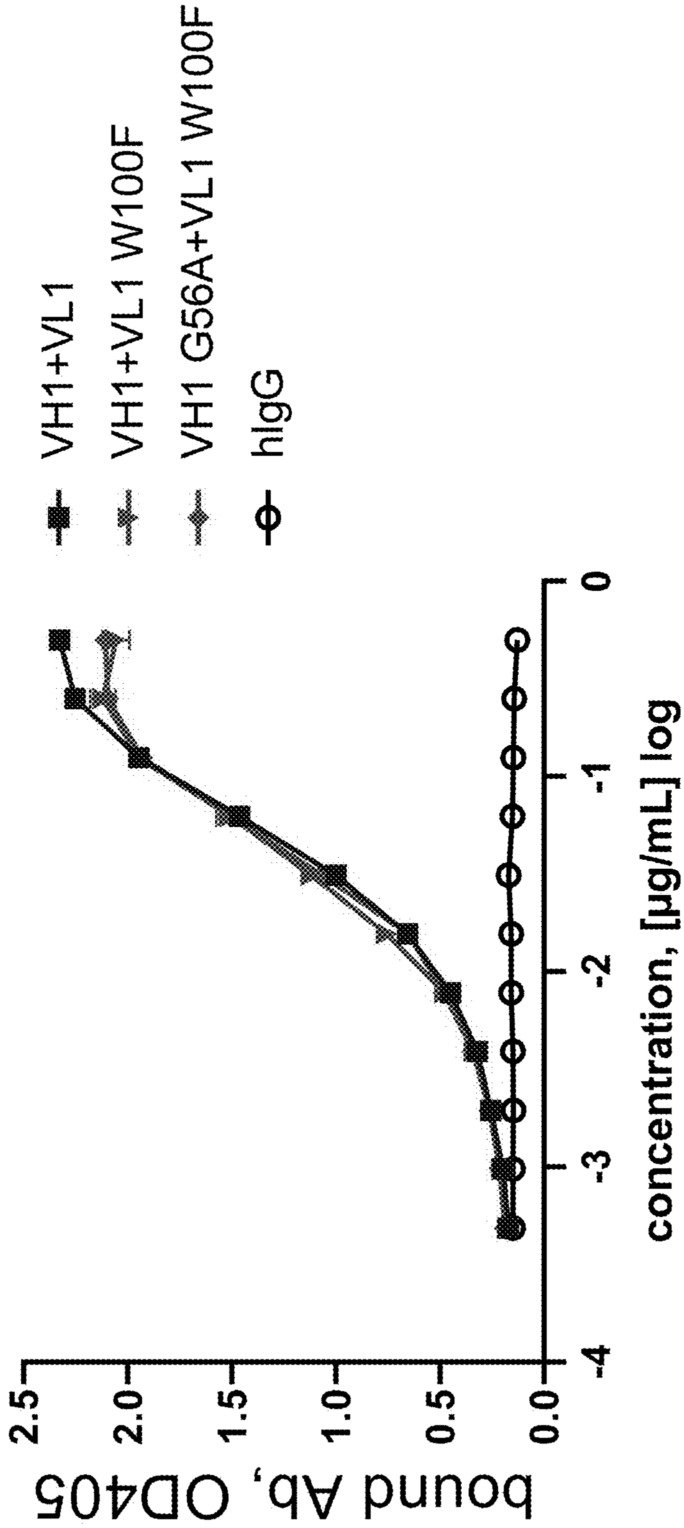

The production and binding affinity of the double mutant VH1 G56A-VL1 W100F was also tested. This double mutant was produced at comparable levels and bound to human recombinant IL13Rα2 with a similar affinity as both the single mutant VH1-VL1 W100F and the non-mutated humanized antibody (VH1-VL1) (FIG. 24). These mutations found in this double mutant each offer potential therapeutic advantages, as the G56A mutation disrupts an isomerization site and the W100F mutation removes an oxidation site. Thus, antibodies and BTEs produced with these mutations are predicted to be more stable in vivo and to provide stability for storage and processing that provide benefits for large scale production, storage and distribution in providing a more stable and less aggregation-prone antibody or BTE product but still maintaining a highly pure and sufficient binder to the target IL13Rα molecule.

Example 7: Humanized Bispecific T-Cell Engager Specific for IL13Rα (BTE) Antibody In the following Example, the inventor describes the generation of and assessment of a Bi-specific T-cell engager (BTE) that simultaneously targets the T cell protein CD3ε and the glioblastoma (GBM) protein interleukin 13 receptor alpha (L13Rα). This BTE is a bispecific fusion protein that comprises two single-chain variable fragments (scFvs) connected by flexible linker.

The first scFv is derived from the fully human anti-CD3 antibody 28F1 (amino acid sequences SEQ ID NO:51 and 52 and polynucleotide sequences SEQ ID NO:61 and 62 derived from the sequences described in U.S. Pat. No. 7,728,114 and Schaller et al. Pharmacokinetic Analysis of a Novel Human EGFRvIII:CD3 Bispecific Antibody in Plasma and Whole Blood Using a High-Resolution Targeted Mass Spectrometry Approach. J Proteome Res. 2019 Aug. 2; 18(8):3032-3041. doi: 10.1021/acs.jproteome.9b00145. Epub 2019 Jul. 19. PMID: 31267741; PMCID: PMC7325320, FIG. 1, the contents of which are incorporated by reference in their entireties). The second scFv is derived from the humanized anti-IL13Rα2 antibody described herein, including the point mutations that increased the stability of the anti-L13Rα antibody (see schematic in FIG. 25A and particularly including in some embodiments, the point mutations G56A and W100F). Specifically, the orientation of the VH and VL domains and linker between two scFvs is important for the design of the BTE. The suitable BTEs designed have the following orientation: α-CD3 VH-linker-αCD3 VL-linker-humanized VH scFvIL13Rα2-linker humanized scFvIL13Rα2 VL. Suitable polypeptides comprising the BTEs are found in SEQ ID NO:48, SEQ ID NO:49; SEQ ID NO:56-59.

This novel humanized CD3:IL13Ra2 bi-specific antibody specifically binds IL13Ra2, but not IL13Ra1, activates T cells as judged by the markers of T cells activation and specifically kill IL13Ra2 expressing GBM6 cells as demonstrated in this example.

Figure 25:
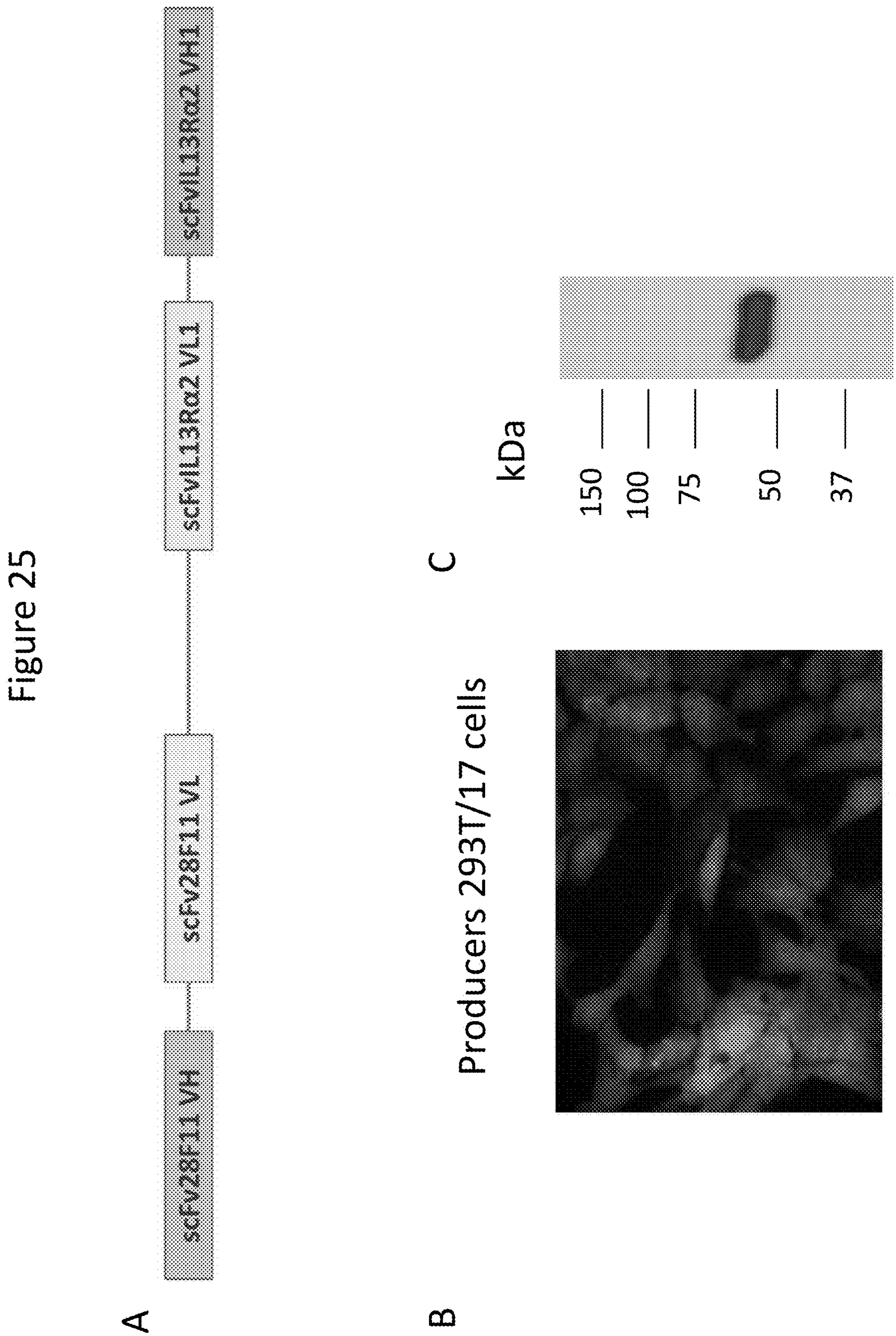
FIG. 25 depicts the generation of $BTE^{on}$. (A) Schematic of $BTE^{on}$, a bispecific fusion protein that comprises two single-chain variable fragments (scFvs) connected by flexible linker. The first scFv is derived from the fully human anti-CD3 antibody 28F1, and the second scFv is derived from the humanized anti-IL13Rα2 (clone 47) antibody described herein. (B) Image of the 293T/17 cells used to express $BTE^{on}$. (C) Protein gel showing purified $BTE^{on}$. (D) Binding of the humanized BTE to human IL13Rα2 in plate ELISA. Binding is compared to that of the murine version of the BTE, which comprises a first scFv derived from the anti-CD3 antibody Okt3 and a second scFv is derived from the murine anti-IL13Rα2 antibody.
Figure 25:
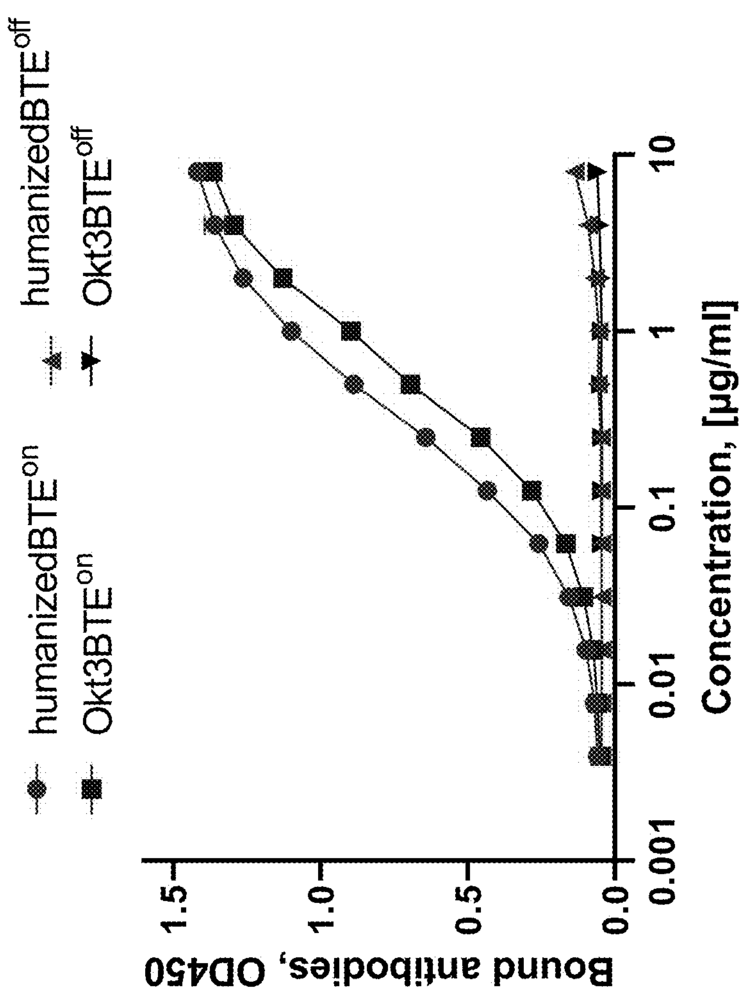

The BTEs were generated and expressed in 293T/17 cells (FIG. 25B-C). Bispecific T cell engager (BTE) targeting IL13Rα2 was generated using single-chain variable region (scFv) described herein and scFv of the mAb 28F11 directed towards CD 3. ScFvs were connected using a flexible glycine/serine linker in the following orientation displayed in FIG. 25. $BTE_{OFF}$ and $BTE_{ON}$ control molecules were generated by replacing the complementary determinant region 3 of the mAb47 light chain and heavy chain with the sequence of the mAb MOPC-21, which prevents IL13Rα2 binding. Polyhistidine (6His) tag was added at the C-terminus of BTE constructs for BTE purification and detection. An additional BTE construct using Okt3BTE was used as a control (comprising the chimeric mouse/human BTE using the mouse VH and VL in the BTE.

Lentiviral vectors (pLVX-IRES-ZsGreen1) encoding cDNA for each BTE were constructed, and the corresponding lentiviral particles were used to transduce HEK293T cells for the production of BTE proteins. Recombinant BTE proteins were purified from culture supernatants using His-Pure resin. Purified BTE integrity was verified by western blotting using anti-His antibodies (FIG. 25).

BTE cDNAs were codon-optimized for human cells' expression, synthesized, and cloned in pAmp vector by the Thermo Fisher Scientific (Waltham, MA). Alexafluo647 labeling kit was used to label generated BTEs for the binding studies. Using online ExPASy tools (www.expasy.org/tools/), amino acid length and molecular weight was calculated (("Quest Calculate™ IgG Concentration Calculator." AAT Bioquest, Inc, 17 Jan. 2020, www.aatbio.com/tools/calculate-IgG-concentration).

The pLVX-IRES-ZsGreen1 plasmid (Takara Bio USA, Inc., Mountain View, CA) was used to generate construct encoding BTE cDNA. Briefly, the plasmid was cut with EcoRI and BamHI restriction enzymes (NEB, Ipswich, MA), and BTE cDNA excised from the pAmp vector was directly ligated with T4DNA ligase. DH5α cells (NEB, Ipswich, MA) were transformed and grown overnight on ampicillin LB agar plates. Selected colonies were grown in LB broth in the presence of 100 μg/mL of ampicillin. Plasmid DNA was purified using reagents and QIAGEN Plasmid Midi Kits protocol (Germantown, MD). Purified DNA was subjected to Sangers sequencing (GENEWIZ, South Plainfield, NJ). Lentivirus plasmids encoding for BTEs cDNA and 4th generation Lenti-X™ Packaging Single Shots (Takara Bio USA, Inc., Mountain View, CA) were used to produce lentiviral particles in HEK 293/17 cells. Cell supernatants were collected at 24 and 48 h after transfection of HEK 293/17 cells and concentrated using a LentiX concentrator (Takara Bio USA, Inc., Mountain View, CA). HEK 293/17 cells or NSC cells were plated in 6 well plates at a density of $10^5$ per well, and next day transduced with viral concentrate in the presence of 4 and 1 μg/mL polybrene, respectively (Sigma, St. Louis, MO), and cultured overnight at 37° C./5% $CO_2$. The following day media was replaced, and the transduced cells were expanded. Transduced 293T or NSCs were subjected to fluorescence-activated cell sorting (Robert H. Lurie Comprehensive Cancer Center Flow Cytometry Core Facility (RHLCCC), Chicago, IL) to select for cells expressing a comparable level of ZsGreen1 protein among different BTE lines. Sorted cells were expanded in culture as specified. Before the collection of the supernatant containing the BTE proteins, 293T cells at 80% confluence were shifted to 32° C. and incubated for 3 days in the presence of the proteases inhibitors (Sigma, St. Louis, MO) to induced maximal protein production. NSC secreting BTE proteins were cultured at 37° C./5% $CO_2$.

Figure 29:
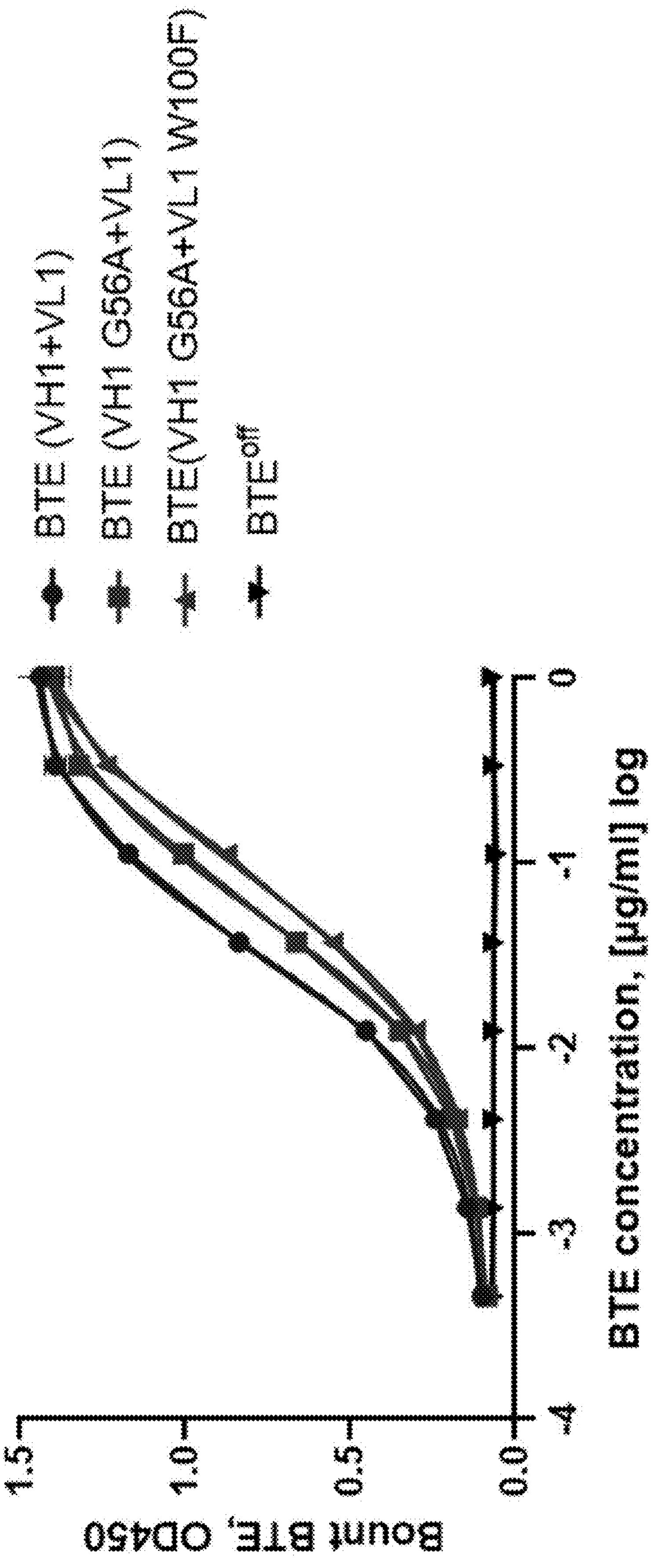
FIG. 29 is a representative graft depicting the affinity for L13Ra2 of a single and double mutant BTE (VH1G56-VL1 and VH1G56A-VL1W100F).

The binding affinity of the BTE to recombinant human IL13Ra2 was measured by plate ELISA and demonstrated better binding characteristics that the chimeric BTE using the mouse monoclonal Ab $V_H$ and $V_L$ domains. Enzyme-linked immunosorbent (ELISA) assay was performed to determine the binding of BTE proteins to human IL13Rα2. ELISA was performed in 96-well plates coated with 1 μg/mL of human recombinant IL13Rα2hFc (cat #7147-IR-100, R&D Systems, Minneapolis, MN). Following blocking with PBS/2% FBS and washes with TBS-Tween 20 buffer (Boston Bioproducts, Ashland, MA), purified BTE proteins or NSCs supernatants were incubated for 1 h room temperature (RT) at various concentrations or dilutions. Bound BTE proteins were detected with HRP-conjugated anti-6×HIS tag antibodies (ab1187, Abcam, Cambridge, MA) using 1-Step™ Slow TMB-ELISA (Thermo Scientific, Rockford, IL) and 2N HCl according to manufacturer's directions. Plates were read at 450 nm and 570 nm using a BioTek plate reader (BioTek, Winooski, VT), and data were plotted using the Microsoft Excel program prior to analysis. ELISA was also performed for the VH1G56-VL1 and VH1G56A-VL1W100F as shown in FIG. 29 showing the BTE with single and double mutations bind IL12Ra2. Additional experiments show they are fully functional.

Figure 26:
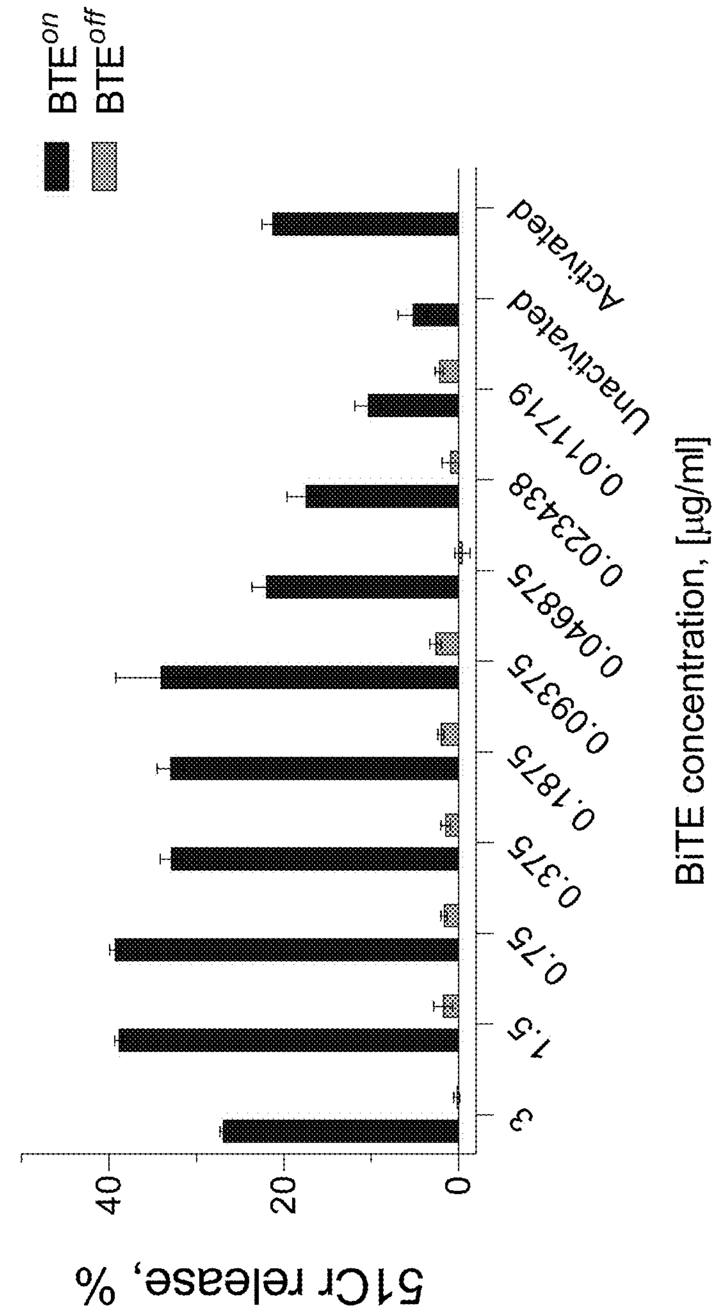
FIG. 26 shows the results of a Chromium-51 ($^{51}Cr$) release assay for $BTE^{on}$ and $BTE^{off}$. Panel A shows the results generated using GBM6 cells, while panel B shows the results generated using GBM12 cells.
Figure 26:
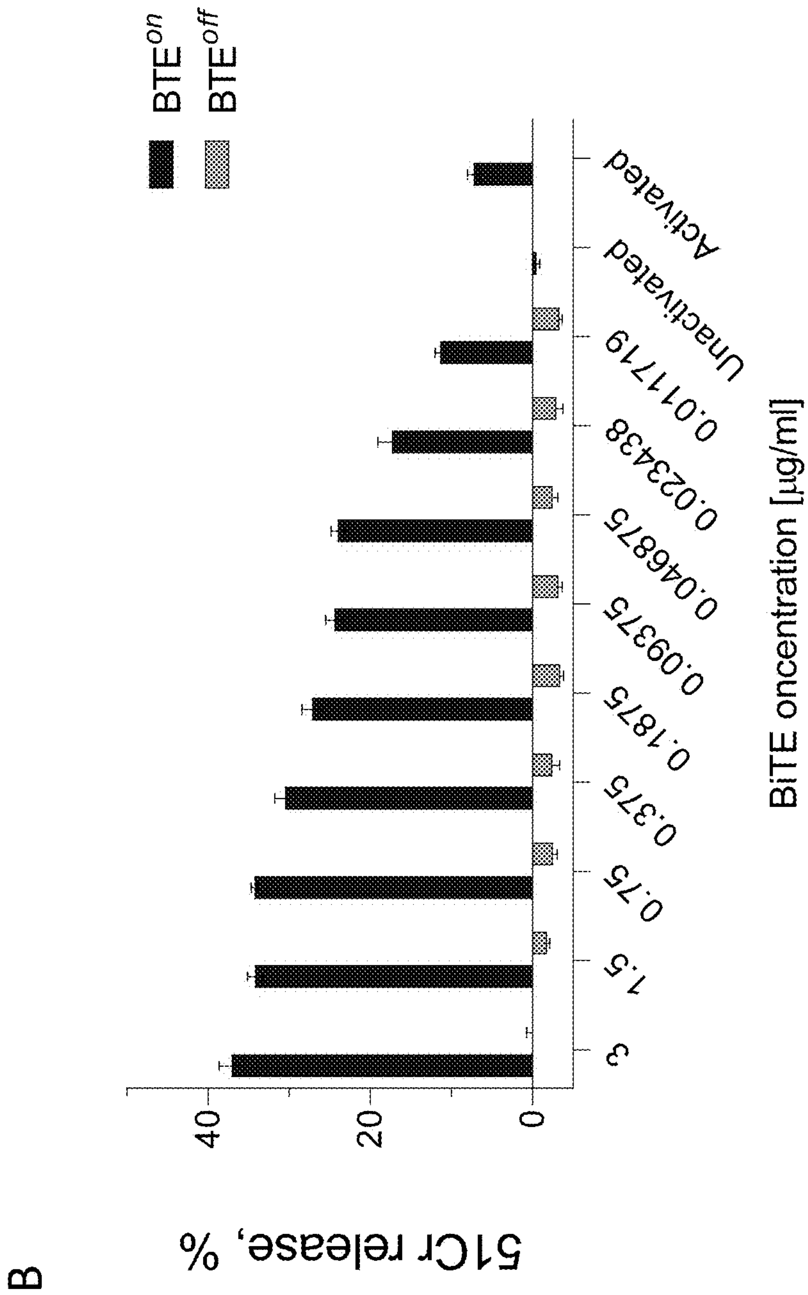

Next, a Chromium-51 ($^{51}$Cr) release assay was performed to assess the ability of the BTE to assess its cytotoxicity against glioblastoma (GBM) cells. The results of this assay demonstrate that the BTE activated donor T cells (peripheral blood mononuclear cells) and killed IL13Rα2-expressing GBM6 cells (FIG. 26).

Figure 27:
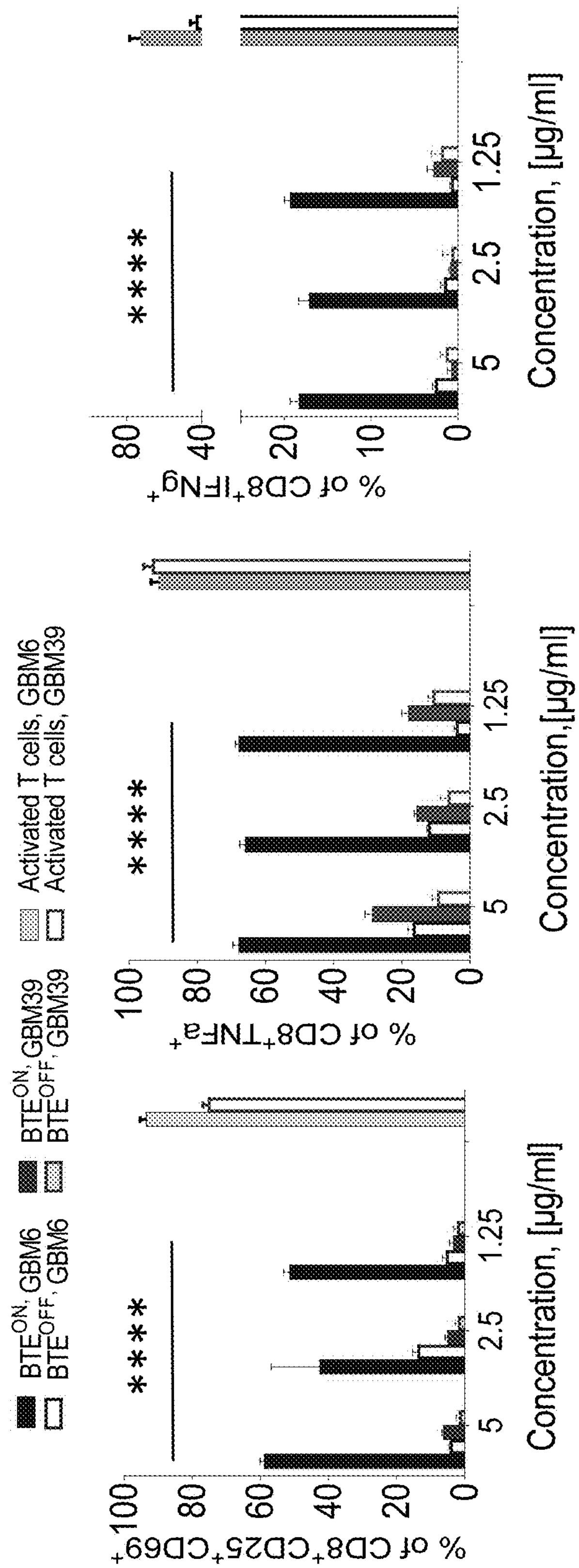
FIG. 27 demonstrates that $BTE^{on}$ activates donor' CD8+ T cells in co-culture with the IL13Rα2-expressing GBM6 patient-derived xenograft line, but not with IL13Rα2-negative GBM39 patient-derived xenograft line. Activation of T cells with CD3/CD28/CD2 beads ("Activated T cells) served as a positive control. N=4. Data presented as mean±SD FIG. 28 are representative amino acid sequences and a polynucleic acid sequence of the bispecific T cell engagers contemplated in some embodiments of the present invention.

Finally, the ability of the BTE to activate T cells was tested. The results demonstrate that the BTE activates donor CD8+ T cells in co-culture with the IL13Rα2-expressing GBM6 patient-derived xenograft line, but not with IL13Rα2-negative GBM39 patient-derived xenograft line (FIG. 27). PB CD3+ and CD8+ TILs were used for the co-culture in functional assays. Two types of controls were used in all experiments: activated cells co-cultured in the presence of CD3/CD28/CD2 activating bead (STEMCELL Technologies, Vancouver, Canada) and non-activated cells co-cultured in the presence of complete media without beads. IL13Rα2+ cells of hrIL13Rα2 were used for antigenic stimulation except when noted. GBM39, IL13Rα2-negative cells or GBM-free co-cultures were used as antigen specificity controls. The co-culture experiments were at the range of the target to effector cells (T:E) ratio 1:1-1:30 as specified, where the target is glioma cells, and effectors are T cells. In experiments with BTEs, dose-response concentrations of the recombinant protein were as specified.

The cytotoxic activity of T cells against glioma cells in the presence of the BTE proteins or NSCs secreting BTE proteins was determined using a standard $^{51}$Cr release assay. Released Cr51 readings were obtained at 18-24 h of the co-culture, as previously described.

What is claimed:

1. A humanized antibody that binds to IL13Rα2 comprising:

a variable light domain ($V_L$) comprising an amino acid sequence of SEQ ID NO:53; and a variable heavy domain ($V_H$) comprising an amino acid sequence of SEQ ID NO:54.

2. The humanized antibody of claim 1, wherein (a) $X_1$ in $V_L$ is F; (b) $X_2$ in $V_H$ is E, (c) $X_3$ in $V_H$ is A; or (d) combinations of (a), (b) and (c).

3. The humanized antibody of claim 1, further comprising:

an agent selected from a therapeutic agent and a detection agent.

4. The humanized antibody of claim 1, wherein the variable heavy domain ($V_H$) and the variable light domain ($V_L$) are linked by a flexible linker, wherein the linker is an amino acid sequence of about 4-25 amino acids in length and comprising glycine and serine.

5. The humanized antibody of claim 1, wherein the antibody is a single-chain variable fragment antibody.

6. The humanized antibody of claim 1, wherein the antibody comprises a signal sequence N-terminal to the variable heavy domain ($V_H$).

7. The humanized antibody of claim 6, wherein the signal sequence is SEQ ID NO:29.

8. A method of treating an IL13Rα2-expressing cancer in a subject, the method comprising: administering a therapeutically effective amount of the humanized antibody of claim 1 to treat the cancer.

9. A humanized antibody that binds to IL13Rα2, comprising:

(a) a heavy chain comprising SEQ ID NO:1, SEQ ID NO:2, SEQ ID NO:3, SEQ ID NO:4, SEQ ID NO:9, SEQ ID NO:10, SEQ ID NO:11, or SEQ ID NO:12; and (b) a light chain comprising SEQ ID NO:5, SEQ ID NO:6, SEQ ID NO: 7, SEQ ID NO:8, SEQ ID NO:13, SEQ ID NO:14, SEQ ID NO:15, or SEQ ID NO:16.

10. The humanized antibody of claim 9, wherein the heavy chain is selected from the group consisting of SEQ ID NO:9, SEQ ID NO:10,SEQ ID NO:11, and SEQ ID NO:12, and comprises one or more mutations selected from M34L, M34A, M34I, M34V, D52E, P53A, D55E, and G56A; and wherein the light chain is selected from the group consisting of SEQ ID NO:13, SEQ ID NO:14, SEQ ID NO:15, and SEQ ID NO:16, and comprises one or more mutations selected from M37L, M37I, M37V, Q58R, Q58A, Q94E, Q94R, Q94A, W100F, and W100Y.

11. The humanized antibody of claim 9, wherein the antibody cannot isomerize and comprises:

(i) a heavy chain selected from SEQ ID NO:9, SEQ ID NO:10, SEQ ID NO:11, or SEQ ID NO: 12, wherein the heavy chain comprises G56A, and a light chain selected from SEQ ID NO:5, SEQ ID NO:6, SEQ ID NO:7, SEQ ID NO:8, SEQ ID NO:13, SEQ ID NO:14, SEQ ID NO:15, or SEQ ID NO:16; or (ii) a heavy chain selected from SEQ ID NO:9, SEQ ID NO:10, SEQ ID NO:11, or SEQ ID NO:12, wherein the $V_H$ comprises D55E, and a light chain selected from SEQ ID NO:5, SEQ ID NO:6, SEQ ID NO:7, SEQ ID NO:8, SEQ ID NO:13, SEQ ID NO:14, SEQ ID NO:15, or SEQ ID NO:16.

12. The humanized antibody of claim 9, wherein the antibody comprises:

(i) SEQ ID NO:1 and SEQ ID NO:5;

(ii) SEQ ID NO:1 and SEQ ID NO:6;

(iii) SEQ ID NO:1 and SEQ ID NO:7;

(iv) SEQ ID NO:1 and SEQ ID NO:8;

(v) SEQ ID NO:2 and SEQ ID NO:5;

(vi) SEQ ID NO:2 and SEQ ID NO:6;

(vii) SEQ ID NO:2 and SEQ ID NO:7;

(viii) SEQ ID NO:2 and SEQ ID NO:8;

(ix) SEQ ID NO:3 and SEQ ID NO:5

(x) SEQ ID NO:3 and SEQ ID NO:6;

(xi) SEQ ID NO:3 and SEQ ID NO:7;

(xii) SEQ ID NO:3 and SEQ ID NO:8;

(xiii) SEQ ID NO:4 and SEQ ID NO:5;

(xiv) SEQ ID NO:4 and SEQ ID NO:6;

(xv) SEQ ID NO:4 and SEQ ID NO:7; or (xvi) SEQ ID NO:4 and SEQ ID NO:8.

13. An engineered bispecific antibody comprising a first single-chain variable fragment (scFv) that binds to CD3 and a second scFv that binds to IL13Rα2, wherein the first scFv comprises:

(a) a variable light domain ($V_H$) comprising an amino acid sequence of SEQ ID NO:51; a (b) a first flexible linker; and (c) a variable heavy domain ($V_L$) comprising an amino acid sequence of SEQ ID NO:52, and wherein the second scFv comprises:

(d) a variable light domain ($V_L$) comprising an amino acid sequence of SEQ ID NO:53;

(e) a second linker; and (f) a variable heavy domain ($V_H$) comprising an amino acid sequence of SEQ ID NO:54; and wherein the bispecific antibody comprises from N terminal to C terminal: the $V_H$ of the first scFv, the $V_L$ of the first scFv, the $V_L$ of the second scFv, and the $V_H$ of the second scFv.

14. The engineered bispecific antibody of claim 13, wherein the first single-chain variable fragment (scFv) that binds to CD3 and second scFv that binds to IL13Rα2 are linked via a third flexible linker.

15. The engineered bispecific antibody of claim 13, wherein (a) the first and second linker are an amino acid sequence of about 10-20 amino acids consisting of glycine and serine, (b) the third linker is an amino acid sequence of about 20-30 amino acids consisting of glycine and serine, or (c) both (a) and (b).

16. The engineered bispecific antibody of claim 15, wherein the first and second linker are SEQ ID NO:55, and the third linker is SEQ ID NO:56.

17. The engineered bispecific antibody of claim 13, wherein amino acid sequence further comprises a signal peptide comprising SEQ ID NO:50 on the N terminal end.

18. The engineered bispecific antibody of claim 13, wherein the $V_H$ of the second scFv comprises a mutation, wherein the mutation is at least one of $X_2$ is E and $X_3$ is A.

19. The engineered bispecific antibody of claim 13, wherein the engineered bispecific T cell engager comprises:

an amino acid sequence selected from the group consisting of SEQ ID NO:49, SEQ ID NO:57, SEQ ID NO:58, SEQ ID NO:59, SEQ ID NO:60.

20. A method of treating an IL13Rα2-expressing cancer in a subject, the method comprising: administering a therapeutically effective amount of the bispecific antibody of claim 13 to the subject to treat the cancer.

* * * * *